(12) United States Patent
Greve

(10) Patent No.: US 11,077,172 B2
(45) Date of Patent: Aug. 3, 2021

(54) IL-2 VARIANTS FOR THE TREATMENT OF PSORIASIS

(71) Applicant: Delinia, Inc., Emeryville, CA (US)

(72) Inventor: Jeffrey Greve, Berkeley, CA (US)

(73) Assignee: DELINIA, INC., Emeryville, CA (US)

( * ) Notice: Subject to any disclaimer, the term of this patent is extended or adjusted under 35 U.S.C. 154(b) by 0 days.

(21) Appl. No.: 15/806,787

(22) Filed: Nov. 8, 2017

(65) Prior Publication Data

US 2018/0125941 A1 May 10, 2018

Related U.S. Application Data

(60) Provisional application No. 62/419,118, filed on Nov. 8, 2016.

(51) Int. Cl.
| | | |
|---|---|---|
| A61K 38/20 | (2006.01) | |
| C07K 14/47 | (2006.01) | |
| C07K 14/55 | (2006.01) | |
| A61K 39/00 | (2006.01) | |

(52) U.S. Cl.
CPC ...... *A61K 38/2013* (2013.01); *C07K 14/4713* (2013.01); *C07K 14/55* (2013.01); *A61K 2039/505* (2013.01); *C07K 2319/30* (2013.01)

(58) Field of Classification Search
CPC .................................................. A61K 38/2013
See application file for complete search history.

(56) References Cited

U.S. PATENT DOCUMENTS

| | | |
|---|---|---|
| 4,853,332 A | 8/1989 | Mark et al. |
| 4,902,502 A | 2/1990 | Nitecki et al. |
| 5,089,261 A | 2/1992 | Nitecki et al. |
| 5,206,344 A | 4/1993 | Katre et al. |
| 5,466,447 A | 11/1995 | Abels et al. |
| 5,650,150 A | 7/1997 | Gillies |
| 6,348,192 B1 | 2/2002 | Chan et al. |
| 6,541,610 B1 | 4/2003 | Smith |
| 6,689,353 B1 | 2/2004 | Wang et al. |
| 6,927,043 B2 | 8/2005 | Chan et al. |
| 6,955,807 B1 | 10/2005 | Shanafelt et al. |
| 7,105,653 B2 | 9/2006 | Shanafelt et al. |
| 7,148,321 B2 | 12/2006 | Gillies et al. |
| 7,186,804 B2 | 3/2007 | Gillies et al. |
| 7,371,371 B2 | 5/2008 | Epstein et al. |
| 7,452,966 B2 | 11/2008 | Glaesner et al. |
| 7,462,350 B2 | 12/2008 | Gillies et al. |
| 7,569,215 B2 | 8/2009 | Wittrup et al. |
| 7,579,439 B2 | 8/2009 | Strom et al. |
| 7,888,071 B2 | 2/2011 | Gillies et al. |
| 7,951,360 B2 | 5/2011 | Wittrup et al. |
| 8,012,465 B2 | 9/2011 | Elias et al. |
| 8,043,608 B2 | 10/2011 | Gillies et al. |
| 8,066,994 B2 | 11/2011 | Gillies et al. |
| 8,124,066 B2 | 2/2012 | Epstein et al. |
| 8,349,311 B2 | 1/2013 | Wittrup et al. |
| 8,993,524 B2 | 3/2015 | Bedi et al. |
| 9,206,243 B2 | 12/2015 | León Monzón et al. |
| 9,289,493 B2 | 3/2016 | Ko |
| 10,294,287 B2 | 5/2019 | Greve |
| 10,774,126 B2 * | 9/2020 | Greve ..................... A61P 37/06 |
| 2004/0171154 A1 | 9/2004 | Storici et al. |
| 2006/0160187 A1 | 7/2006 | Denis-Mize et al. |
| 2007/0036752 A1 | 2/2007 | Gillies et al. |
| 2011/0020266 A1 | 1/2011 | Nissen et al. |
| 2011/0091412 A1 | 4/2011 | Wittrup et al. |
| 2011/0150826 A1 | 6/2011 | Paulsen et al. |
| 2011/0274650 A1 | 11/2011 | Gavin et al. |
| 2012/0276125 A1 | 11/2012 | Ast et al. |
| 2013/0195795 A1 | 8/2013 | Gavin et al. |
| 2014/0004080 A1 | 1/2014 | Klatzmann et al. |
| 2014/0044675 A1 | 2/2014 | Hosse et al. |
| 2014/0046026 A1 | 2/2014 | Garcia et al. |
| 2014/0285898 A1 | 9/2014 | Moliton |
| 2014/0286898 A1 | 9/2014 | Gavin et al. |
| 2014/0328791 A1 | 11/2014 | Bossard et al. |
| 2014/0343252 A1 | 11/2014 | Gavin et al. |
| 2015/0017120 A1 | 1/2015 | Wittrup et al. |
| 2015/0132254 A1 | 5/2015 | Wittrup et al. |
| 2015/0218260 A1 | 8/2015 | Klein et al. |
| 2015/0374788 A1 | 12/2015 | Paulsen et al. |
| 2016/0090407 A1 | 3/2016 | Hosse et al. |

(Continued)

FOREIGN PATENT DOCUMENTS

| | | |
|---|---|---|
| CN | 102174111 | 9/2011 |
| CN | 103193887 | 7/2013 |

(Continued)

OTHER PUBLICATIONS

Mikayama et al. Proc. Natl. Acad. Sci. USA (1993) vol. 90, pp. 10056-10060.*

Voetetal. Biochemistry John Wiley & Sons, Inc., (1990), pp. 126-128 and 228-234.*

Altschul, Stephen F., et al., "Basic Local Alignment Search Tool", Journal of Molecular Biology, 1990, vol. 215, pp. 403-410.

Altschul, Stephen F., et al., "Gapped Blast and PSI-BLAST: a new generation of protein database search programs", Nucleic Acids Research, 1997, vol. 25, No. 17, pp. 3389-3402.

Argos, Patrick, "An Investigation of Oligopeptides Linking Domains in Protein Tertiary Structures and Possible Candidates for General Gene Fusion", Journal of Molecular Biology, 1990, vol. 211, pp. 943-958.

(Continued)

*Primary Examiner* — Prema M Mertz
(74) *Attorney, Agent, or Firm* — McCarter & English, LLP

(57) ABSTRACT

This disclosure provides for a method for treating a condition by administering to a subject in need thereof a therapeutically-effective amount of a compound that comprises an IL-2 receptor-binding moiety. The methods described in the present disclosure provide enhanced pharmacokinetic profiles. The disclosure also provides methods for treating autoimmune disease comprising administering a therapeutically-effective amount of a fusion protein comprising an IL-2 variant protein.

13 Claims, 25 Drawing Sheets

Specification includes a Sequence Listing.

(56) References Cited

U.S. PATENT DOCUMENTS

| | | |
|---|---|---|
| 2016/0208017 A1 | 7/2016 | Ast et al. |
| 2016/0263240 A1 | 9/2016 | Ast et al. |
| 2017/0037102 A1 | 2/2017 | Greve |
| 2019/0153058 A1 | 5/2019 | Greve |
| 2019/0202881 A1 | 7/2019 | Greve |
| 2019/0202882 A1 | 7/2019 | Greve |

FOREIGN PATENT DOCUMENTS

| | | |
|---|---|---|
| EP | 1076704 | 2/2001 |
| EP | 1370280 | 12/2003 |
| EP | 1454138 | 9/2004 |
| EP | 1688146 | 8/2006 |
| EP | 2288372 | 3/2011 |
| JP | 2007-500132 | 1/2007 |
| JP | 2010-504755 | 2/2010 |
| JP | 2012-521196 | 9/2012 |
| JP | 2014-94898 | 5/2014 |
| JP | 2016-518823 | 6/2016 |
| WO | WO-90/00565 | 1/1990 |
| WO | WO-95/08340 | 3/1995 |
| WO | WO-99/43713 | 9/1999 |
| WO | WO-99/60128 | 11/1999 |
| WO | WO-03/048334 | 6/2003 |
| WO | 2005/012530 | 2/2005 |
| WO | WO-2005/014642 | 2/2005 |
| WO | WO-2008/003473 | 1/2008 |
| WO | 2008/042236 | 4/2008 |
| WO | 2010/085495 | 7/2010 |
| WO | WO-2010/085495 | 7/2010 |
| WO | 2010/108127 | 9/2010 |
| WO | WO-2011/109789 | 9/2011 |
| WO | WO-2012/107417 | 8/2012 |
| WO | 2012/146628 | 11/2012 |
| WO | WO-2012/146628 | 11/2012 |
| WO | WO-2014/023752 | 2/2014 |
| WO | 2014/153111 | 9/2014 |
| WO | WO-2014/145907 | 9/2014 |
| WO | WO-2014/201378 | 12/2014 |
| WO | 2015/118016 | 8/2015 |
| WO | WO-2015/164815 | 10/2015 |
| WO | WO-2016/014428 | 1/2016 |
| WO | WO-2016/025385 | 2/2016 |
| WO | WO-2016/025645 | 2/2016 |
| WO | WO-2016/025647 | 2/2016 |
| WO | WO-2016/057651 | 4/2016 |
| WO | WO-2016/164937 | 10/2016 |
| WO | 2017/127514 | 7/2017 |

OTHER PUBLICATIONS

Atkins, Michael B., et al., "Hypothyroidism After Treatment with Interleukin-2 and Lymphokine-Activated Killer Cells", The New England Journal of Medicine, Jun. 16, 1988, vol. 318, No. 24, pp. 1557-1563.

Batzer, Mark A., "Enhanced evolutionary PCR using oligonucleotides with inosine at the 3'-terminus", Nucleic Acids Research, Jul. 12, 1991, vol. 19, No. 18, p. 5081.

Bell, Charles J.M., et al., "Sustained in vivo signaling by long-lived IL-2 induces prolonged increases of regulatory T cells", Journal of Autoimmunity, 2015, vol. 56, pp. 66-80.

Bensinger, Steven J., et al., "Distinct IL-2 Receptor Signaling Pattern in CD4+CD25+ Regulatory T Cells", May 1, 2004, The Journal of Immunology, vol. 172, No. 9, pp. 5287-5296.

Calissano, Mattia, et al., "In Vivo site-directed Mutagenesis of Neurospora crassa beta-tubulin gene by spheroplasts transformation with oligonucleotides", Jul. 1996, No. 43, pp. 15-16.

Cantrell, Doreen A., et al., "The Interleukin-2 T-Cell System: A New Cell Growth Model", Science, Jun. 22, 1984, vol. 224, pp. 1312-1316.

Cassell, Delanie J., et al., "Therapeutic Enhancement of IL-2 Through Molecular Design", Current Pharmaceutical Design, 2002, vol. 8, No. 24, pp. 2171-2183.

Chen, Xiaoying, et al., "Fusion protein linkers: Property, design and functionality", Advanced Drug Delivery Reviews, 2013, vol. 65, pp. 1357-1369.

Chen, Qian, et al., "IL-2 Controls the Stability of Foxp3 Expression in TGF-β-Induced Foxp3+ T Cells in Vivo", The Journal of Immunology, Apr. 27, 2011, vol. 186, pp. 6329-6337.

Chianese-Bullock, Kimberly A., et al., "Autoimmune Toxicities Associated with the Administration of Antitumor Vaccines and Low-Dose Interleukin-2", Journal of Immunotherapy, Jul./Aug. 2005, vol. 28, No. 4, pp. 412-419.

Czajkowsky, Daniel M., et al., "Fc-fusion proteins: new developments and future perspectives", EMBO Molecular Medicine, 2012, vol. 4, pp. 1015-1028.

Dauphinee, M.J., et al., "Interleukin 2 deficiency is a common feature of autoimmune mice", The Journal of Immunology, Dec. 1981, vol. 127, No. 6, pp. 2483-2487.

Davey, Richard T., et al., "Safety, Tolerability, Pharmacokinetics, and Efficacy of an Interleukin-2 Agonist Among HIV-Infected Patients Receiving Highly Active Antiretroviral Therapy", Journal of Interferon & Cytokine Research, 2008, vol. 28, pp. 89-100.

Dumont, Jennifer A., et al., "Monomeric Fc Fusions: Impact on Pharmacokinetic and Biological Activity of Protein Therapeutics", Biodrugs, 2006, vol. 20, No. 3, pp. 151-160.

Furtado, Glaucia C., et al., "Interleukin 2 Signaling Is Required for CD4+ Regulatory T Cell Function", The Journal of Experimental Medicine, Sep. 16, 2002, vol. 196, No. 6, pp. 851-857.

Gilles, Stephen D., et al., "Antibody-targeted interleukin 2 stimulates T-cell killing of autologous tumor cells", Proceedings of the National Academy of Sciences of the United States of America, Feb. 1992, vol. 89, pp. 1428-1432.

Gilles, Stephen D., et al., "Improved Circulating Half-Life and Efficacy of an Antibody-Interleukin 2 Immunocytokine Based on Reduced Intracellular Proteolysis", Clinical Cancer Research, 2002, vol. 8, pp. 210-216.

Hecht, Randy, et al., "Rationale-Based Engineering of a Potent Long-Acting FGF21 Analog for the Treatment of Type 2 Diabetes", PLOS One, Nov. 2012, vol. 7, Issue 11, pp. 1-14.

Hoffmann, Petra, et al., "Donor-type CD4+CD25+ Regulatory T Cells Suppress Lethal Acute Graft-Versus-Host Disease after Allogeneic Bone Marrow Transplantation", The Journal of Experimental Medicine, Aug. 5, 2002, vol. 196, No. 3, pp. 389-399.

Huang, Fang-Ping, et al., "Restoration of an Early, Progressive Defect in Responsiveness to T-Cell Activation in Lupus Mice by Exogenous IL-2", Autoimmunity, 1993, vol. 15, pp. 19-29.

Jailwala, Parthav, et al., "Apoptosis of CD4+CD25high T Cells in Type 1 Diabetes May Be Partially Mediated by IL-2 Deprivation", PLOS One, Aug. 2009, vol. 4, Issue 8, pp. 1-13.

Karlin, Samuel, et al., "Methods for assessing the statistical significance of molecular sequence features by using general scoring schemes", Proceedings of the National Academy of Sciences of the United States of America, Mar. 1990, vol. 87, pp. 2264-2268.

King, David M., et al., "Phase I Clinical Trial of the Immunocytokine EMD 273063 in Melanoma Patients", Journal of Clinical Oncology, Nov. 15, 2004, vol. 22, No. 22, pp. 4463-4473.

Kirchner, G.I., et al., "Pharmacokinetics of recombinant human interleukin-2 in advanced renal cell carcinoma patients following subcutaneous application", British Journal of Clinical Pharmacology, 1998, vol. 46, pp. 5-10.

Kitas, G.D., et al., "Deficient Interleukin 2 Production in Rheumatoid Arthritis: Association with Active Disease and Systemic Complications", Clinical & Experimental Immunology, 1988, vol. 73, pp. 242-249.

Klatzmann, David, et al., "The promise of low-dose interleukin-2 therapy for autoimmune and inflammatory diseases", Nature Reviews Immunology, Apr. 17, 2015, vol. 15, pp. 1-12.

Koreth, John, et al., "Interleukin-2 and Regulatory T Cells in Graft-versus-Host Disease", The New England Journal of Medicine, Dec. 1, 2011, vol. 365, No. 22, pp. 2055-2066.

Kren, Betsy T., et al., "In Vivo site-directed mutagenesis of the factor IX gene by chimeric RNA/DNA oligonucleotides", Nature Medicine, Mar. 1998, vol. 4, No. 3, pp. 285-290.

Kroemer, Guido, et al., "The role of interleukin 2 in autoimmunity", Immunology Today, 1989, vol. 10, No. 7, pp. 246-251.

(56) References Cited

OTHER PUBLICATIONS

Liston, Adrian, "Tracing the action of IL-2 in tolerance to islet-specific antigen", Immunology and Cell Biology, 2007, vol. 85, pp. 338-342.
Liu, Zhi, et al., "A Novel Antibody Engineering Strategy for Making Monovalent Bispecific Heterodimeric IgG Antibodies by Electrostatic Steering Mechanism", The Journal of Biological Chemistry, Mar. 20, 2015, vol. 290, No. 12, pp. 7535-7562.
Long, S. Alice, et al., "Defects in IL-2R Signaling Contribute to Diminished Maintenance of FoxP3 Expression in CD4+CD25+ Regulatory T-Cells of Type 1 Diabetic Subjects", Diabetes, Feb. 2010, vol. 59, pp. 407-415.
Mahmud, Shawn A., et al., "Interleukin-2 and STAT5 in Regulatory T Cell Development and Function", JAK-STAT, Dec. 27, 2016, vol. 2, Issue 1, pp. 1-6.
Malek, Thomas R., et al., "CD4 Regulatory T Cells Prevent Lethal Autoimmunity in IL-2Rβ-Implications for the Nonredundant Function of IL-2", Immunity, Aug. 2002, vol. 17, pp. 167-178.
Malek, Thomas R., et al., "Interleukin-2 Receptor Signaling: At the Interface between Tolerance and immunity", Immunity 33, Aug. 27, 2010, pp. 153-165.
Malek, Thomas R., et al., "Tolerance, Not Immunity, Crucially Depends on IL-2", Nature Reviews, Immunology, Sep. 2004, vol. 4, pp. 665-674.
Margolin, Kim, et al., "Phase I Trial of Bay 50-4798, an Interleukin-2-Specific Agonist in Advanced Melanoma and Renal Cancer", Clinical Cancer Research, Jun. 1, 2007, vol. 12, No. 11, pp. 3312-3319.
Moschos, Stergios J., et al., "Focus on Focis: Interleukin 2 Treatment Associated Autoimmunity", Clinical Immunology, 2009, vol. 127, pp. 123-129.
Myszka, David G., et al., "Kinetic Analysis of Ligand Binding to Interleukin-2 Receptor Complexes Created on an Optical Biosensor Surface", Protein Science, 1996, vol. 5, pp. 2648-2478.
Oganesyan, Vaheh, et al., "Structural characterization of a human Fc fragment engineered for lack of effector functions", Acta Crystallographica Section D, Biological Crystallography, 2008, D64, pp. 700-704.
Ohtsuka, Eiko, et al., "An Alternative Approach to Deoxyoligonucleotides as Hybridization Probes by Insertion of Deoxyinosine at Ambiguous Codon Positions", The Journal of Biological Chemistry, Mar. 10, 1985, vol. 260, No. 5, pp. 2605-2608.
Penichet, Manuel L., et al., "Antibody-IL-2 fusion proteins: A novel strategy for immune potentiation", Human Antibodies, 1997, vol. 8, No. 3, pp. 106-118.
Poli, Aurelie, et al., "CD56bright natural killer (NK) cells: an important NK cell subset", British Society for Immunology, 2009, vol. 126, pp. 458-465.
Promethe Laboratories, Inc. PROLEUKIN® (aldesleukin) for injection, for intravenous infusion. Available at http://proleukin.com/assets/pdf/proleukin.pdf. Accessed on Oct. 11, 2016. pp. 1-19.
Rabinovitch, Alex, et al., "Combination Therapy with Sirolimus and Interleukin-2 Prevents Spontaneous and Recurrent Autoimmune Diabetes in NOD Mice", Diabetes, Mar. 2002, vol. 51, pp. 638-645.
Ribas, Antoni, et al., "Phase I/II open-label study of the biologic effects of the interleukin-2 immunocytokine EMD 273063 (hu I 4. I 8-IL2) in patients with metastatic malignant melanoma", Journal of Translational Medicine, Jul. 29, 2009, vol. 7, No. 68, pp. 1-11.
Ring, Aaron M., et al., "Mechanistic and structural insight into the functional dichotomy between interleukin-2 and interleukin-15", National Institute of Health, Nat. Immunology, Dec. 2012, vol. 13, No. 12, pp. 1-24.
Rossolini, Gian Maria, et al., "Use of deoxyinosine-containing primers vs degenerate primers for polymerase chain reaction based on ambiguous sequence information", Molecular and Cellular Probes, 1994, vol. 8, pp. 91-98.
Saadoun, David, et al., "Regulatory T-Cell Responses to Low-Dose Interleukin-2 in HCV-Induced Vasculitis", The New England Journal of Medicine, Dec. 1, 2011, vol. 365, No. 22, pp. 2067-2077.

Sadlack, Benjamin, et al., "Generalized autoimmune disease in interleukin-2-deficient mice is triggered by an uncontrolled activation and proliferation of CD4+ T cells", European Journal of Immunology, 1995, vol. 25, pp. 3053-3059.
Salfeld, Jochen G., "Isotype selection in antibody engineering", Nature Biotechnology, Dec. 2007, vol. 25, No. 12, pp. 1369-1372.
Schellenberger, Volker, et al., "A recombinant polypeptide extends the in vivo half-life of peptides and proteins in a tunable manner", Nature Biotechnology, Dec. 2009, vol. 27, No. 12, pp. 1186-1190.
Schlapschy, Martin, et al., "Fusion of a recombinant antibody fragment with a homo-amino-acid polymer: effects on biophysical properties and prolonged plasma half-life", Protein Engineering, Design & Selection, 2007, vol. 20, No. 6, pp. 273-284.
Serreze, David V., et al., "Immunostimulation Circumvents Diabetes in NOD/Lt Mice", Journal of Autoimmunity, 1989, vol. 2, pp. 759-776.
Shanafelt, Armen B., et al., "A T-cell-selective interleukin 2 mutein exhibits potent antitumor activity and is well tolerated in vivo", Nature Biotechnology, Nov. 2000, vol. 18, pp. 1197-1202.
Sleep, Darrell, et al., "Albumin as a versatile platform for drug half-life extension", Biochimica et Biophysica Acta 1830, 2013, pp. 5526-5534.
Sondel, Paul M., et al., "Current and Potential Uses of Immunocytokines as Cancer Immunotherapy", Antibodies, 2012, vol. 1, pp. 149-171.
Steppan, Sonja, et al., Genome Wide Expression Profiling of Human Peripheral Blood Mononuclear Cells Stimulated with Bay 50-4798, a Novel T Cell Selective Interleukin-2 Analog, Journal of Immunotherapy, Feb./Mar. 2007, vol. 30, No. 2, pp. 150-168.
Steppan, Sonja, et al., "Reduced Secondary Cytokine Induction by BAY 50-4798, a High Affinity Receptor-Specific Interleukin-2 Analog", Journal of Interferon & Cytokine Research, 2006, vol. 26, pp. 171-178.
Storici, Francesca, et al., "In vivo site-directed mutagenesis using oligonucleotides", Nature Biotechnology, Aug. 2001, vol. 19, pp. 773-776.
Suzuki, Haruhiko, et al., "Deregulated T Cell Activation and Autoimmunity in Mice Lacking Interleukin-2 Receptor β", Science, Jun. 9, 1995, vol. 268, pp. 1472-1476.
Sykes, Megan, et al., "In Vivo Administration of Interleukin 2 Plus T Cell-Depleted Syngeneic Marrow Prevents Graft-Versus-Host Disease Mortality and Permits Alloengraftment", The Journal of Experimental Medicine, Mar. 1990, vol. 171, pp. 645-658.
Sykes, Megan, et al., "Interleukin 2 prevents graft-versus-host disease while preserving the graft-versus-leukemia effect of allogeneic T cells", Proceedings of the National Academy of Sciences, USA, Aug. 1990, vol. 87, pp. 5633-5637.
Tang, Qizhi, et al., "Regulatory T-Cell Therapy in Transplantation: Moving to the Clinic", Cold Spring Harbor Perspectives in Medicine, 2013, vol. 3, pp. 1-15.
Tang, Qizhi, et al., "Central Role of Defective Interleukin-2 Production in the Triggering of Islet Autoimmune Destruction", Immunity, May 2008, vol. 28, pp. 687-697.
Tang, Qizhi, et al., "In Vitro-expanded Antigen-specific Regulatory T Cells Suppress Autoimmune Diabetes", The Journal of Experimental Medicine, Jun. 7, 2004, vol. 199, No. 11, pp. 1455-1465.
Tao, M.H., et al., "Studies of aglycosylated chimeric mouse-human IgG. Role of carbohydrate in the structure and effector functions mediated by the human IgG constant region", The Journal of Immunology, Oct. 15, 1989, vol. 143, pp. 2595-2601.
Tian, Jingdong, et al., "Accurate Multiplex Gene Synthesis from Programmable DNA Microchips" Nature, Dec. 2004, vol. 432, pp. 1050-1054.
Vazquez-Lombardi, Rodrigo, et al., "Potent antitumour activity of interleukin-2-Fc fusion proteins requires Fc-mediated depletion of regulatory T-cells", Nature Communications, May 12, 2017, vol. 8, pp. 1-12.
Wang, Xinquan, et al., "Structure of the Quaternary Complex of Interleukin-2 with Its α, β, and $y_c$ Receptors", Science, Nov. 18, 2005, vol. 310, pp. 1159-1163.
Weishaupt, Andreas, et al., "The T cell-selective IL-2 mutant AIC284 mediates protection in a rat model of Multiple Sclerosis", Journal of Neuroimmunology, 2015, vol. 282, pp. 63-72.

(56) References Cited

OTHER PUBLICATIONS

Willerford, Dennis M, et al., "Interleukin-2 Receptor a Chain Regulates the Size and Content of the Peripheral Lymphoid Compartment", Immunity, Oct. 1995, vol. 3, pp. 521-530.

You, Sylvaine, et al., "Adaptive TGF-β-dependent regulatory T cells control autoimmune diabetes and are a privileged target of anti-CD3 antibody treatment", PNAS, Apr. 10, 2007, vol. 104, No. 15, pp. 6335-6340.

Zheng, Xin Xiao, et al., "Favorably Tipping the Balance between Cytopathic and Regulatory T Cells to Create Transplantation Tolerance", Immunity, Oct. 2003, vol. 19, pp. 503-514.

Zheng, Xin Xiao, et al., "IL-2 Receptor-Targeted Cytolytic IL-2/Fc Fusion Protein Treatment Blocks Diabetogenic Autoimmunity in Nonobese Diabetic Mice", The Journal of immunology, 1999, vol. 163, pp. 4041-4048.

Zhu, Zhenping, et al., "Remodeling domain interfaces to enhance heterodimer formation", Protein Science, 1997, vol. 6, pp. 781-788.

Zhu, Eric F., et al., "Synergistic Innate and Adaptive Immune Response to Combination Immunotherapy with Anti-Tumor Antigen Antibodies and Extended Serum Half-Life IL-2", Cancer Cell, Apr. 13, 2015, vol. 27, pp. 489-501.

Zorn, Emmanuel, et al., "IL-2 regulates FOXP3 expression in human CD4+CD25+ regulatory T cells through a STAT-dependent mechanism and induces the expansion of these cells in vivo", Blood, Sep. 2006, vol. 108, No. 5, pp. 1571-1579.

Zorn, Emmanuel, et al., "Combined CD4+ Donor Lymphocyte Infusion and Low-Dose Recombinant IL-2 Expand FOXP3+ Regulatory T Cells following Allogeneic Hematopoietic Stem Cell Transplantation", National Institute of Health, Biology of Blood and Marrow Transplantation, Mar. 2009, vol. 15, No. 3, pp. 382-388.

Supplementary European Search Report dated Nov. 16, 2017, based on co-pending European Patent Application No. 15824955.7,—9 Pages.

International Search Report dated Mar. 26, 2018, based on co-pending PCT International Application No. PCT/US2017/060534—7 Pages.

Written Opinion dated Mar. 26, 2018, based on co-pending PCT International Application No. PCT/US2017/060534—8 Pages.

Sugiyama, Hideaki, et al., "Dysfunctional Blood and Target Tissue CD4+CD25high Regulatory T Cells in Psoriasis: Mechanism Underlying Unrestrained Pathogenic Effector T Cell Proliferation", The Journal of Immunology, Jan. 1, 2005, vol. 174, No. 1, pp. 164-173.

Chen, Xiaoying, et al., "Fusion Protein Linkers: Property, design and functionality", Advanced Drug Delivery Reviews, 2013, vol. 65, No. 10, pp. 1357-1369.

Mikayama, Toshifumi, et al., "Molecular Cloning and Functional Expression of a cDNA Encoding Glycosylation-Inhibiting Factor", Nov. 1993, Proceedings of the National Academy of Sciences of the U.S., vol. 90, pp. 10056-10060.

Yamada, Akiko, et al., "Role of Regulatory T Cell in the Pathogenesis of Inflammatory Bowel Disease", World Journal of Gastroenterology, Feb. 21, 2016, vol. 22, No. 7, pp. 2195-2206.

European Supplementary Search Report based on co-pending European Patent Application No. 17869254, dated Apr. 17, 2020—16 Pages.

* cited by examiner

Fc fusion proteins

IL-2(C125S)

N = 3 animals/group

IL-2 VARIANTS FOR THE TREATMENT OF PSORIASIS

RELATED APPLICATIONS

This application claims priority to U.S. Provisional Patent Application No. 62/419,118 filed on Nov. 8, 2016, the contents of which are incorporated herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 127754_00402_Revised Sequence_Listing. The size of the text file is 13 KB, and the text file was created on Jan. 10, 2020.

BACKGROUND

Autoimmune diseases are characterized by an excessive reaction of the immune system against endogenous tissue. Immune response mechanisms include an activation of specialized cells and an acquisition of effector functions. Regulatory T cells (Tregs), previously also described as suppressor T cells, are a specialized subgroup of T cells. Tregs suppress activation of the immune system and thereby regulate the self-tolerance of the immune system. Thus, Tregs play an important role in preventing the onset of autoimmune diseases, and therapies that can enhance Treg activity may be useful in the treatment of autoimmune diseases.

SUMMARY OF THE INVENTION

In certain aspects, the invention relates to a method for treating an autoimmune disease, the method comprising administering to a subject in need thereof at least two doses of a pharmaceutical composition comprising a therapeutically effective amount of a fusion protein comprising: a human IL-2 variant protein domain comprising a substitution selected from the group consisting of D20H, N88I, N88G, N88R, Q126L, and Q126F relative to the amino acid sequence of SEQ ID NO: 2; a peptide linker domain; and an IgG Fc protein domain, wherein each domain has an amino-terminus (N-terminus) and a carboxy terminus (C-terminus); and wherein the fusion protein is configured so that the C-terminus of the human IL-2 variant protein domain is fused through a peptide bond to the N-terminus of the peptide linker domain, and the N-terminus of the IgG Fc protein domain is fused through a peptide bond to the C-terminus of the peptide linker domain, wherein the composition is administered to the subject at a dosing frequency from once every week to once every month. In certain embodiments, administration of the pharmaceutical composition to the subject increases the ratio of regulatory T cells (Treg) to conventional T cells (Tconv) to at least 0.2. In certain embodiments, five days after the pharmaceutical composition is administered to the subject the Treg/Tconv ratio is at least 0.2.

In certain aspects, the invention relates to a method for increasing proliferation and/or activity of regulatory T cells in a subject in need thereof, the method comprising administering to the subject at least two doses of a pharmaceutical composition comprising a therapeutically effective amount of a fusion protein comprising: a human IL-2 variant protein domain comprising a substitution selected from the group consisting of D20H, N88I, N88G, N88R, Q126L, and Q126F relative to the amino acid sequence of SEQ ID NO: 2; a peptide linker domain; and an IgG Fc protein domain, wherein each domain has an amino-terminus (N-terminus) and a carboxy terminus (C-terminus); and wherein the fusion protein is configured so that the C-terminus of the human IL-2 variant protein domain is fused through a peptide bond to the N-terminus of the peptide linker domain, and the N-terminus of the IgG Fc protein domain is fused through a peptide bond to the C-terminus of the peptide linker domain, wherein the composition is administered to the subject at a dosing frequency from once every week to once every month.

In certain embodiments of the methods described herein, administration of the pharmaceutical composition to the subject results in a greater increase in the proliferation and/or activity of regulatory T cells relative to a composition comprising an equimolar amount of aldesleukin. In certain embodiments, administration of the pharmaceutical composition to the subject increases the level of regulatory T cells by at least 2-fold relative to the level of regulatory T cells in the subject before treatment with the pharmaceutical composition. In certain embodiments, administration of the pharmaceutical composition to the subject does not increase the proliferation of conventional T cells or CD8+ T cells. In certain embodiments, administration of the pharmaceutical composition to the subject increases the level of a biomarker selected from the group consisting of CD25, FOXP3, CTLA-4, ICOS, and CD39 in the regulatory T cells.

In certain aspects, the invention relates to a method for maintaining the ratio of regulatory T cells (Treg) to conventional T cells (Tconv) at a level that is sufficient for treatment of an autoimmune disease in a subject in need of treatment for the autoimmune disease, the method comprising administering to the subject at least two doses of a pharmaceutical composition comprising a therapeutically effective amount of a fusion protein comprising: a human IL-2 variant protein domain comprising a substitution selected from the group consisting of D20H, N88I, N88G, N88R, Q126L, and Q126F relative to the amino acid sequence of SEQ ID NO: 2; a peptide linker domain; and an IgG Fc protein domain, wherein each domain has an amino-terminus (N-terminus) and a carboxy terminus (C-terminus); and wherein the fusion protein is configured so that the C-terminus of the human IL-2 variant protein domain is fused through a peptide bond to the N-terminus of the peptide linker domain, and the N-terminus of the IgG Fc protein domain is fused through a peptide bond to the C-terminus of the peptide linker domain, wherein the composition is administered to the subject at a dosing frequency from once every week to once every month. In certain embodiments, five days after the pharmaceutical composition is administered to the subject the Treg/Tconv ratio is at least 0.2.

In certain aspects, the invention relates to a method for treating an autoimmune disease, the method comprising: (i) administering to a subject in need thereof a first dose of a therapeutically-effective amount of a pharmaceutical composition comprising a fusion protein comprising: a human IL-2 variant protein domain comprising a substitution selected from the group consisting of D20H, N88I, N88G, N88R, Q126L, and Q126F relative to the amino acid sequence of SEQ ID NO: 2; a peptide linker domain; and an IgG Fc protein domain, wherein each domain has an amino-terminus (N-terminus) and a carboxy terminus (C-terminus); and wherein the fusion protein is configured so that the C-terminus of the human IL-2 variant protein domain is fused through a peptide bond to the N-terminus of the peptide linker domain, and the N-terminus of the IgG Fc protein domain is fused through a peptide bond to the C-terminus of the peptide linker domain; (ii) measuring expression of a biomarker in a sample obtained from the subject after the first dose has been administered to the subject to determine a peak level of the biomarker, wherein the biomarker is selected from the group consisting of CD25, FOXP3, CTLA-4, ICOS, and CD39; (iii) administering a second dose of a therapeutically-effective amount of the pharmaceutical composition to the subject when the level of the at least one biomarker is reduced by at least 10% relative to the peak level of the biomarker. In certain embodiments, the biomarker is CD25.

In certain embodiments of the methods described herein, the dosing frequency ranges from once every week to once every 2 weeks. In certain embodiments, administration of the pharmaceutical composition to the subject does not cause diarrhea in the subject. In certain embodiments, the human IL-2 variant protein domain comprises the N88R substitution relative to the amino acid sequence of SEQ ID NO: 2. In certain embodiments, the human IL-2 variant protein domain comprises a T3A substitution relative to the amino acid sequence of SEQ ID NO: 2. In certain embodiments, the human IL-2 variant protein domain comprises a C125S substitution relative to the amino acid sequence of SEQ ID NO: 2. In certain embodiments, the human IL-2 variant protein domain comprises an amino acid sequence having at least 95% sequence identity to SEQ ID NO: 2. In certain embodiments, the human IL-2 variant protein domain comprises the amino acid sequence SEQ ID NO: 1 or SEQ ID NO: 3. In certain embodiments, the peptide linker domain is a sequence of amino acid residues that are each independently serine or glycine. In certain embodiments, the peptide linker domain is 15 amino acid residues. In certain embodiments, the peptide linker domain comprises the amino acid sequence of SEQ ID NO: 6. In certain embodiments, the IgG Fc protein domain is an IgG1 Fc protein domain. In certain embodiments, the IgG Fc protein domain comprises the amino acid sequence of SEQ ID NO: 7. In certain embodiments, the fusion protein comprises the amino acid sequence of SEQ ID NO: 4 or SEQ ID NO: 5.

In certain embodiments of the methods described herein, the therapeutically-effective amount is from about 5 µg/kg to about 250 µg/kg. In certain embodiments, the autoimmune disease is selected from the group consisting of Pemphigus Vulgaris, Type 1 Diabetes, Systemic Lupus Erythematosus, Graft-versus-Host Disease, Autoimmune Vasculitis, Ulcerative Colitis, Crohn's Disease, Psoriasis, Multiple Sclerosis, Amytrophic Lateral Sclerosis, Alopecia Areata, Uveitis, Duchenne Muscular Dystrophy, Scleroderma, Neuromyelitis Optica. In certain embodiments, the subject is human. In certain embodiments, the pharmaceutical composition is administered to the subject by subcutaneous administration.

In some embodiments, the present disclosure provides a method for treating a condition, the method comprising administering to a subject in need thereof a therapeutically-effective amount of a compound, wherein the compound comprises a moiety that binds an IL-2 receptor in the subject, wherein administration of the compound to the subject at 50 µg/kg provides in the subject an $AUC_{0-\infty}$ of about 2000 ng-h/mL to about 10,000 ng-h/mL.

In some embodiments, the present disclosure provides a method for treating a condition, the method comprising administering to a subject in need thereof a therapeutically-effective amount of a compound, wherein the compound comprises a moiety that binds an IL-2 receptor in the subject, wherein administration of the compound to the subject at 50 µg/kg provides in the subject a clearance of about 4 mL/h-kg to about 20 mL/h-kg.

In some embodiments, the present disclosure provides a method for treating a condition, the method comprising administering to a subject in need thereof a therapeutically-effective amount of a compound, wherein the compound comprises a moiety that binds an IL-2 receptor in the subject, wherein administration of the compound to the subject at 50 µg/kg provides in the subject a half-life of about 10 h to about 30 h.

In some embodiments, the present disclosure provides a method for treating a condition, the method comprising administering to a subject in need thereof a therapeutically-effective amount of a compound, wherein the compound comprises a moiety that binds an IL-2 receptor in the subject, wherein administration of the compound to the subject at 50 µg/kg provides in the subject a half-life of about 6 h to about 15 h.

In some embodiments, the present disclosure provides a method for treating a condition, the method comprising administering to a subject in need thereof a therapeutically-effective amount of a compound, wherein the compound comprises a moiety that binds an IL-2 receptor in the subject, wherein administration of the compound to the subject at 50 µg/kg provides in the subject a Cmax of about 500 ng/mL to about 3,000 ng/mL.

In certain embodiments of the aforementioned methods, the administration increases a regulatory T cell count in the subject more than does administration of an equivalent amount (e.g. an equimolar amount) of a wild-type IL-2 polypeptide or a C125S IL-2 (e.g. aldesleukin) to the subject. In certain embodiments, the administration provides in the subject a half-life that is greater than a half-life obtained by administering an equivalent amount of wild-type IL-2 or a C125S IL-2 (e.g. aldesleukin) to the subject. In certain embodiments, the administration increases a regulatory T cell count in the subject relative to a T effector cell count in the subject. In certain embodiments, the administration selectively activates regulatory T cells in the subject relative to conventional T cells in the subject. In certain embodiments, the administration selectively activates an IL2Rαβγ receptor complex in the subject over an IL2Rβγ receptor complex in the subject. In certain embodiments, the therapeutically-effective amount is from about 5 µg/kg to about 250 µg/kg. In certain embodiments, the therapeutically-effective amount is about 25 µg/kg.

In certain embodiments of the aforementioned methods, the condition is an autoimmune disease. In certain embodiments, the condition is Pemphigus Vulgaris. In certain embodiments, the condition is Type 1 Diabetes. In certain embodiments, the condition is Systemic Lupus Erythematosus. In certain embodiments, the condition is Graft-versus-Host Disease. In certain embodiments, the condition is Autoimmune Vasculitis. In certain embodiments, the condition is Ulcerative Colitis. In certain embodiments, the condition is Crohn's Disease. In certain embodiments, the condition is Psoriasis. In certain embodiments, the condition is Multiple Sclerosis. In certain embodiments, the condition is Amytrophic Lateral Sclerosis. In certain embodiments, the condition is Alopecia Areata. In certain embodiments, the condition is Uveitis. In certain embodiments, the condition is Duchenne Muscular Dystrophy. In certain embodiments, the autoimmune disease is Scleroderma. In certain embodiments, the autoimmune disease is Neuromyelitis Optica.

In certain embodiments of the aforementioned methods, the subject is human. In certain embodiments, the administration is intravenous. In certain embodiments, the administration is subcutaneous. In certain embodiments, the pharmaceutical composition comprises an IL-2 polypeptide. In certain embodiments, the moiety that binds the IL-2 receptor in the subject is a peptide sequence that has at least 90% identity to wild-type IL-2. In certain embodiments, the moiety that binds the IL-2 receptor in the subject differs from wild-type IL-2 in a substitution that is N88R with respect to the wild-type IL-2. In certain embodiments, the moiety that binds the IL-2 receptor in the subject comprises a mutation with respect to wild-type IL-2 that increases stability with respect to wild-type IL-2 of the moiety that binds the IL-2 receptor in the subject. In certain embodiments, the mutation that increases stability with respect to wild-type IL-2 of the moiety that binds the IL-2 receptor in the subject is a substitution that is C125S with respect to the wild-type IL-2. In certain embodiments, the moiety that binds the IL-2 receptor in the subject differs from wild-type IL-2 in a substitution that is T3A with respect to the wild-type IL-2. In certain embodiments, the moiety that binds the IL-2 receptor in the subject has at least 90% identity to SEQ ID NO: 1. In certain embodiments, the moiety that binds the IL-2 receptor in the subject comprises SEQ ID NO: 1. In certain embodiments, the moiety that binds the IL-2 receptor in the subject is SEQ ID NO: 1.

In certain embodiments of the aforementioned methods, the compound comprises an immunoglobulin Fc domain. In certain embodiments, the immunoglobulin Fc domain is deficient in effector functions relative to a corresponding wild-type immunoglobulin Fc domain. In certain embodiments, the immunoglobulin Fc domain is C-terminal to the moiety that binds the IL-2 receptor in the subject. In certain embodiments, the immunoglobulin Fc domain is an IgG1 immunoglobulin Fc domain. In certain embodiments, the IgG1 immunoglobulin Fc domain differs from a wild-type IgG1 immunoglobulin Fc domain in a substitution that is N297A with respect to the wild-type IgG1 immunoglobulin Fc domain. In certain embodiments, the immunoglobulin Fc domain comprises SEQ ID NO: 7. In certain embodiments, the immunoglobulin Fc domain is SEQ ID NO: 7.

In certain embodiments of the aforementioned methods, the compound comprises a linker peptide covalently linked to the moiety that binds the IL-2 receptor in the subject and covalently linked to the immunoglobulin Fc domain. In certain embodiments, the moiety that binds the IL-2 receptor is N-terminal to the linker peptide, and the immunoglobulin Fc domain is C-terminal to the linker peptide, In certain embodiments, the linker peptide is from 6 to 20 amino acid residues. In certain embodiments, the linker peptide is from 12 to 17 amino acid residues. In certain embodiments, the linker peptide is a sequence of amino acid residues that are each independently serine or glycine. In certain embodiments, the linker peptide is 15 amino acid residues. In certain embodiments, the linker peptide is GGGGSGGGGSGGGGS (SEQ ID NO: 6). In certain embodiments, the compound comprises SEQ ID NO: 4. In certain embodiments, the compound is SEQ ID NO: 4.

DETAILED DESCRIPTION OF THE INVENTION

Figure 1:
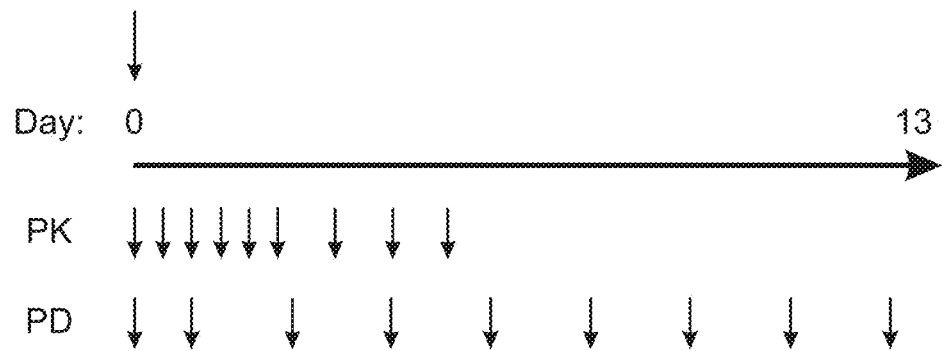
FIG. 1 shows an experimental timeline for dosing cynomolgus monkeys with Compound 1, Compound 2, and IL-2 and subsequently collecting blood samples.
Figure 1:
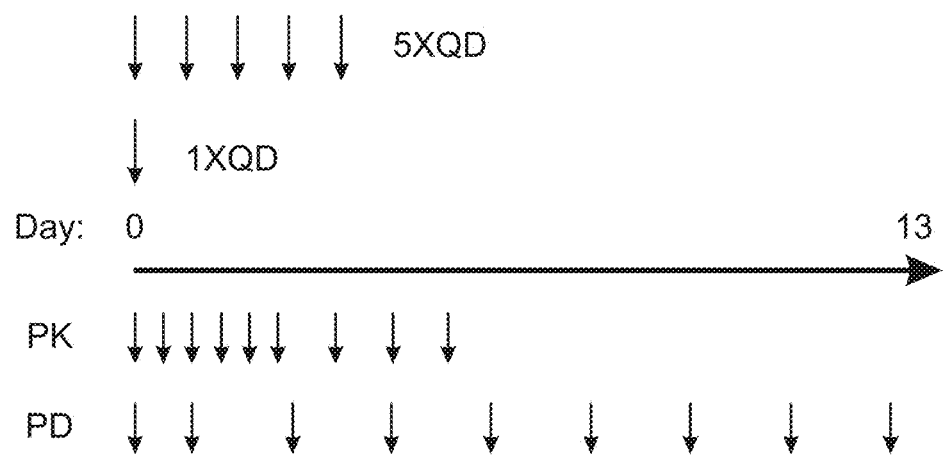

The immune system must be able to discriminate between self and non-self. When self/non-self discrimination fails, the immune system destroys the cells and tissues of the body and as a result causes autoimmune diseases. Regulatory T cells (Tregs) are a class of CD4+CD25+ T cells that suppress the activity of other immune cells, such as conventional T cells (Tconv) and CD8 cells. Tregs are central to immune system homeostasis, and maintain tolerance to self-antigens and in modulating the immune response to foreign antigens. Multiple autoimmune and inflammatory diseases, including Type 1 Diabetes (T1D), Systemic Lupus Erythematosus (SLE), and Graft-versus-Host Disease (GVHD) are associated with a deficiency of Treg cell numbers or Treg function. Regulatory T cells can be activated by Interleukin 2 (IL-2), but IL-2 also activates many other T cell types.

IL-2 binds the IL-2 receptor (IL-2R or IL2R). IL-2R is a heterotrimeric protein expressed on a variety of different immune cell types, including T cells, NK cells, eosinophils, and monocytes. This broad expression pattern provides a pleiotropic effect on the immune system and a high systemic toxicity of IL-2 treatments.

IL2-R has three forms, generated by different combinations of three different IL-2R proteins: α (alpha), β (beta), and γ (gamma). These receptor chains assemble to generate the three different receptor forms: (1) the low affinity receptor, IL2RA, which does not signal; (2) the intermediate affinity receptor (IL2Rβγ), composed of IL2Rβ and IL2Rγ, which is broadly expressed on conventional T cells (Tconv), NK cells, eosinophils, and monocytes; and (3) the high affinity receptor (IL2Rαβγ), composed of IL2Rα, IL2Rβ, and IL2Rγ, which is expressed transiently on activated T cells and constitutively on Treg cells. Conventional T cells are those which are activated by antigens and participate in the immune attack. Conventional T cells include helper T cells, cytotoxic T cells, and memory T cells. Effector T cells (Teff) include various T types that mount a specific immune response to a stimulus. Mutations in IL-2 can change the binding affinity of IL-2 to different IL-2R receptor forms.

Methods and compositions of the present disclosure relate to a molecule comprising a moiety that binds to the IL-2 receptor (e.g. IL-2 or an IL-2 variant) and an immunoglobulin Fc domain. In some embodiments, the molecule also comprises a linker joining the IL-2 receptor-binding moiety and the immunoglobulin Fc domain. The moiety that binds to the IL-2 receptor regulates the activities of white blood cells (leukocytes, often lymphocytes) that are responsible for immunity. The immunoglobulin Fc domain increases the in vivo stability of the molecule, and the linker covalently joins the domains.

Moieties that Bind the IL-2 Receptor

A moiety that binds an IL-2 receptor can be the full length of wild-type IL-2, shorter, or longer. The IL-2 receptor-binding moiety can have a wild-type IL-2 sequence, as shown in SEQ ID NO: 2: (APTSSSTKKTQLQLEHLLLDLQMILNGINNYKNPKL-TRMLTFKFYMPKKATELKHLQCL EEELKPLEEVLN-LAQSKNFHLRPRDLISNINVIVLELKGSETTFMCEYA-DETATIVEFLNR WITFXQSIISTLT) or it may be a variant of IL-2. IL-2 variants can contain one or more substitutions, deletions, or insertions that deviate from the wild-type IL-2 amino acid sequence. Residues are designated herein by the one letter amino acid code followed by the IL-2 amino acid position, e.g., K35 is the lysine residue at position 35 of the wild-type IL-2 sequence. Substitutions are designated herein by the one letter amino acid code followed by the IL-2 amino acid position followed by the substituting one letter amino acid code, e.g., K35A is a substitution of the lysine residue at position 35 of SEQ ID NO: 2 with an alanine residue.

Compounds herein can exhibit specificity for different IL-2 receptor classes that is similar or dissimilar to the specificity of wild-type IL-2. Compounds herein can exhibit increased stability or biological effect in comparison to wild-type IL-2. For example, a mutation can provide a compound with increased specificity for certain IL-2 receptors in comparison to wild-type IL-2. For example, IL-2 N88R is selective for binding to the IL2Rαβγ receptor over the IL2Rβγ receptor. IL-2 can stimulate the proliferation of IL2Rαβγ-expressing PHA-activated T cells as effectively as wildtype IL-2, while exhibiting a 3,000 fold reduced stimulation of the proliferation of IL2Rβγ-expressing NK cells. Other mutations that exhibit increased selectivity for IL2Rαβγ include the substitutions D20H, N88I, N88G, Q126L, and Q126F.

In some embodiments, an IL-2 receptor-binding moiety comprises a mutation that enhances the stability of a compound of the present disclosure. For example, an IL-2 C125S mutation promotes stability by eliminating an unpaired cysteine residue, thereby preventing misfolding of the IL-2 polypeptide. Misfolding can lead to protein aggregation and increase clearance of the polypeptide in vivo. In some embodiments, an IL-2 polypeptide comprises a mutation that creates or removes a glycosylation site. For example the IL-2 mutation T3A removes an O-linked glycosylation site. In some embodiments, an IL-2 variant with the T3A mutation also comprises an N88R mutation and/or a C125S mutation. In some embodiments, an IL-2 variant comprises T3A, N88R, and C125S mutations, as in SEQ ID NO: 3.

In some embodiments, substitutions occur at one or more of positions 3, 20, 88, 125, and 126. In some embodiments, substitutions occur at one, two, three, four, or five of the positions. In some embodiments, an IL-2 variant comprises mutations at positions 88 and 125, for example, N88R and C125S. In some embodiments, an IL-2 receptor-binding moiety comprises the amino acid sequence set forth in SEQ ID NO: 1:
APTSSSTKKTQLQLEHLLLDLQMILNGINNYKNPKL-TRMLTFKFYMPKKATELKHLQCL EEELKPLEEVLN-LAQSKNFHLRPRDLISRINVIVLELKGSETTFMCEYA-DETATIVEFLNR WITFSQSIISTLT. In some embodiments, an IL-2 variant comprises mutations at positions 3, 88 and 125, for example, T3A, N88R and C125S, as in SEQ ID NO: 3:
APASSSTKKTQLQLEHLLLDLQMILNGINNYKNPKL-TRMLTFKFYMPKKATELKHLQCL EEELKPLEEVLN-LAQSKNFHLRPRDLISRINVIVLELKGSETTFMCEYA-DETATIVEFLNR WITFSQSIISTLT. In some embodiments, an IL-2 variant comprises 1, 2, 3, 4, 5, 6, 7, 8, 9, 10, 11, 12, 13, 14, 15, 16, 17, 18, 19, or 20 mutations (e.g., substitutions) in comparison to a wild-type IL-2 sequence.

Compounds herein include IL-2 variants of the present disclosure comprising an amino acid sequence that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the wild-type IL-2 amino acid sequence (SEQ ID NO: 2). Compounds herein include IL-2 variants that comprise an amino acid sequence having an N88R mutation that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the wild-type IL-2 amino acid sequence (i.e. SEQ ID NO: 2). Embodiments also include IL-2 variants that preferentially stimulate Treg cells and comprise an amino acid sequence having N88R and C125S mutations that has at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, or at least 98% sequence identity to the wild-type IL-2 amino acid sequence (SEQ ID NO: 2). Embodiments also include IL-2 variants that preferentially stimulate Treg cells and comprise an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the wild-type IL-2 amino acid sequence (SEQ ID NO: 2).

Various methods and software programs can be used to determine the homology between two or more peptides or nucleic acids, such as NCBI BLAST, Clustal W, MAFFT, Clustal Omega, AlignMe, Praline, or another suitable method or algorithm. In some embodiments, percent identity is calculated by FastDB based upon the following parameters: mismatch penalty of 1; gap penalty of 1; gap size penalty of 0.33; and joining penalty of 30.

An example of a useful algorithm is PILEUP. PILEUP creates a multiple sequence alignment from a group of related sequences using progressive, pairwise alignments. It can also plot a tree showing the clustering relationships used to create the alignment. Useful PILEUP parameters including a default gap weight of 3.00, a default gap length weight of 0.10, and weighted end gaps.

Another example of a useful algorithm is the BLAST algorithm. A useful example of a BLAST program is the WU-BLAST-2 program. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

An additional useful tool is Clustal, a series of commonly used computer programs for multiple sequence alignment. Recent versions of Clustal include ClustalW, ClustalX and Clustal Omega. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

Mutations can be installed at chosen sites or at random. For example, random mutagenesis at a target codon or region can provide mutants to be screened for an activity. Techniques for making substitution mutations at predetermined sites in DNA having a known sequence include, for example, M13 primer mutagenesis and PCR mutagenesis. Screening of the mutants can be accomplished, for example, using assays described herein.

Amino acid substitutions can be of single or multiple residues. Insertions can be, for example, from about 1 to about 20 amino acid residues, or more. Deletions can be, for example, from about 1 to about 20 amino acid residues, or more. Substitutions, deletions, insertions, or any combination thereof can occur in the sample compound.

The Immunoglobulin Fc Domain

Immunoglobulin Fc domains have a number of therapeutic benefits when incorporated into fusion proteins. For example, immunoglobulin Fc domains can (1) endow the fusion partner protein with immunoglobulin Fc effector functions; and/or (2) increase the circulating half-life of the fusion partner protein. The primary effector functions of IgG proteins are Complement-Dependent Cytotoxicity (CDC) and Antibody-Dependent Cellular Cytotoxicity (ADCC), functions mediated by Fc binding to complement protein Clq and to IgG-Fc receptors (FcyR), respectively. These effector functions are important when the therapeutic protein is used to direct or enhance the immune response to a particular antigen target or cell. Effector functions are not needed and can even be toxic, and in some embodiments are not present. For example, an IL-2 receptor-binding moiety with an effector function-competent Fc could kill, rather than activate, Treg cells.

As described above, the fusion proteins described herein can increase the circulating half-life as compared to IL-2 polypeptides without an Fc domain. In some embodiments, the increased circulating half-life is due to the Fc domain preventing aggregation of the fusion protein, thereby increasing its stability and slowing clearance.

The four human IgG subclasses differ in effector functions (CDC, ADCC), circulating half-life, and stability. IgG1 possesses Fc effector functions, and is the most abundant IgG subclass. IgG2 is deficient in Fc effector functions, but is subject to both dimerization with other IgG2 molecules, and instability due to scrambling of disulfide bonds in the hinge region. IgG3 possesses Fc effector functions, and has a long, rigid hinge region. IgG4 is deficient in Fc effector functions, and has a shorter circulating half-life than the other subclasses. The IgG4 dimer is biochemically unstable due to having only a single disulfide bond in the hinge region leading to the exchange of H chains between different IgG4 molecules. Fc sequence modifications can be made to the hinge region of an IgG2 Fc to prevent aggregation, or to the hinge region of an IgG4 Fc to stabilize dimers.

Effector function-deficient variants of IgG1 can be generated. For example, an amino acid substitution can be made at position N297, the location of an N-linked glycosylation site. In some embodiments, the substitution is N297A. Substitution of this asparagine residue removes the glycosylation site and significantly reduces antibody-dependent cell-mediated cytotoxicity (ADCC) and complement-dependent cytotoxicity (CDC) activity, thereby preventing unwanted cell lysis.

Various other effector function-deficient IgG1 variants can also be appreciated by the skilled worker. One non-limiting example of such a variant is IgG1 (L234F/L235E/P331S), which mutates amino acids in the Clq and FcyR binding sites. These (or similar) Fc variants can be used to generate effector-deficient and stable IL-2 selective agonist—Fc fusion proteins(IL2SA-Fc). Forms of Fc protein moieties also can be engineered to create stable monomers rather than dimers. These modified Fc protein moieties also can be combined with an IL-2 compound of the present disclosure. Additionally, a functionally monomeric heterodimer comprising an IL-2-Fc H chain polypeptide can be combined with an Fc H chain polypeptide and assembled using bispecific antibody technology with an IL-2 selective agonist. IL-2 Fc fusion proteins also can be made with intact IgG antibody molecules, either with or without antigen specificity in the IgG moiety. Moreover, Fc variants that lack some or all of the hinge region can be used with the compounds and methods described herein.

In some embodiments, the sequence of an immunoglobulin Fc moiety is DKTHTCPPCPA-PELLGGPSVFLFPPKPKDTLMISRTPE-VTCVVVDVSHEDPEVKFNWYV DGVEVHNAKTKPRE-EQYASTYRVVSVLTVLHQDWLNGKEYKCKVSNKA-LPAPIEKTIS KAKGQPREPQVYTLPPSRDELT-KNQVSLTCLVKGFYPSDIAVEWESNGQPENNYKTTPP VLDSDGSFFLYSK-LTVDKSRWQQGNVFSCSVMHEALHNHYTQKSLSL-SPG (SEQ ID NO: 7). In some embodiments, the immunoglobulin Fc moiety comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 7.

Linker

The linkage at the junction between the Fc and the fusion partner protein can be: (1) a direct fusion of the two protein sequences; (2) a fusion with an intervening linker peptide; or (3) a fusion by a non-peptide moiety. Linker peptides can be included as spacers between two protein moieties. Linker peptides can promote proper protein folding, stability, expression, and bioactivity of the component protein moieties. Long flexible linker peptides can be composed of glycine, serine, threonine, with multiple glycine residues providing a highly flexible conformation. Serine or threonine residues provide polar surface area to limit hydrophobic interaction within the peptide or with the component fusion protein moieties. In some embodiments, peptide linkers are rich in glycine and serine, such as repeats of the sequence GGGGS (SEQ ID NO: 8). In some embodiments, a peptide linker has a sequence of (GGGGS)(SEQ ID NO: 8), wherein n is 1, 2, 3, 4, 5, 6, 7, 8, 9, or 10. In some embodiments, n is 3; i.e., a peptide linker has a sequence of GGGGSGGGGSGGGGS (SEQ ID NO: 6). In some embodiments the peptide linker comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 6.

In some embodiments, the IL-2 receptor-binding moiety is N-terminal to the linker peptide, and the immunoglobulin Fc domain is C-terminal to the linker peptide. In some embodiments, the IL-2 receptor-binding moiety is C-terminal to the linker peptide, and the immunoglobulin Fc domain is N-terminal to the linker peptide.

In a particular embodiment, the compound of the present disclosure is a human IL-2 variant protein domain comprising a substitution selected from the group consisting of D20H, N88I, N88G, N88R, Q126L, and Q126F relative to the amino acid sequence of SEQ ID NO: 2; a peptide linker domain; and an IgG Fc protein domain, wherein each domain has an amino-terminus (N-terminus) and a carboxy terminus (C-terminus); and wherein the fusion protein is configured so that the C-terminus of the human IL-2 variant protein domain is fused through a peptide bond to the N-terminus of the peptide linker domain, and the N-terminus of the IgG Fc protein domain is fused through a peptide bond to the C-terminus of the peptide linker domain.

An example of a compound of the present disclosure is Compound 1, comprising an IL-2 variant with N88R and C125S substitutions, a linker peptide C-terminal to the IL-2 polypeptide, and an IgG1 (N297A) Fc domain C-terminal to the linker peptide. Compound 1 has the sequence of SEQ ID NO: 4: APTSSSTKKTQLQLEHLLLDLQMILNGIN-NYKNPKLTRMLTFKFYMPKKATELKHLQCL EEELKPLEEVLNLAQSKNFHLRPRDLISRIN-VIVLELKGSETTFMCEYADETATIVEFLNR WITFSQSI-ISTLTGGGGSGGGGSGGGGSDKTHTCPPCPA-PELLGGPSVFLFPPKPKDTLMI SRTPEVTCVVVDVSHEDPE-VKFNWYVDGVEVHNAKTKPRE-EQYASTYRVVSVLTVLH QDWLNGKEYKCKVSNKA-LPAPIEKTISKAKGQPREPQVYTLPPSRDELTKNQVS LTCLV KGFYPSDIAVEWESNGQPEN-NYKTTPPVLDSDGSFFLYSK-LTVDKSRWQQGNVFSCSV MHEALHNHYTQKSLSL-SPG. In some embodiments, a compound of the present disclosure comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 4.

A further example of a compound of the present disclosure is Compound 2, comprising an IL-2 variant with T3A, N88R and C125S substitutions, a linker peptide C-terminal to the IL-2 variant, and an IgG Fc domain C-terminal to the linker peptide. Compound 2 has the sequence of SEQ ID NO: 5: APASSSTKKTQLQLEHLLLDLQMILNGIN-NYKNPKLTRMLTFKFYMPKKATELKHLQCL EEELKPLEEVLNLAQSKNFHLRPRDLISRIN-VIVLELKGSETTFMCEYADETATIVEFLNR WITFSQSI-ISTLTGGGGSGGGGSGGGGSDKTHTCPPCPA-PELLGGPSVFLFPPKPKDTLMI SRTPEVTCVVVDVSHEDPE-VKFNWYVDGVEVHNAKTKPRE-EQYASTYRVVSVLTVLH QDWLNGKEYKCKVSNKA-LPAPIEKTISKAKGQPREPQVYTLPPSRDELTKNQVS LTCLV KGFYPSDIAVEWESNGQPEN-NYKTTPPVLDSDGSFFLYSK-LTVDKSRWQQGNVFSCSV MHEALHNHYTQKSLSL-SPG. In certain embodiment, a compound of the present disclosure comprises an amino acid sequence having at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 5.

Regulatory T Cell Proliferation and Activity

In some embodiments, the molecules of the present disclosure increase the regulatory T cell (Treg) count (i.e. proliferation) when administered to a subject. For example, the molecules of the present disclosure can increase the regulatory T cell count in a subject after administration to the subject relative to the subject's regulatory T cell count before administration. For example, administration of a pharmaceutical composition comprising the molecules of the present disclosure to a subject may increase the levels of regulatory T cells in the subject by at least 1-fold, 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold or 60-fold relative to the subject's regulatory T cell count before administration.

In some embodiments, the molecules of the present disclosure can increase the regulatory T cell count in a subject after administration to the subject relative to administration of IL-2 (C125S) (e.g. aldesleukin), e.g., an equimolar amount of IL-2 (C125S) (e.g. aldesleukin). Aldesleukin is an IL-2 variant comprising a C125S substitution relative to human wildtype IL-2 (SEQ ID NO: 2) in which the N-terminal alanine has been removed. Administration of a pharmaceutical composition comprising the molecules of the present disclosure to a subject may increase the levels of regulatory T cells in the subject by at least 10%, 20%, 30%, 40%, 50%, 100%, 150%, 200%, 250%, 300%, 350%, 400%, 450% or 500% relative to an equimolar amount of IL-2 (C125S) (e.g. aldesleukin).

In some embodiments, the molecules of the present disclosure can increase the ratio of regulatory T cells (Treg) to conventional T cells (Tconv) in a subject. In humans, daily low dose IL-2 therapy has been used to treat patients with chronic GVHD by augmenting the levels of Tregs (See Koreth J, et al., Blood. 2016 Jul. 7; 128(1):130-7; and Koreth, J. N Engl J Med. 2011 Dec. 1; 365(22):2055-66). In the latter trial, IL-2 (aldesleukin) was administered by daily subcutaneous injection for 12 weeks. Overall, patients in these trials attained a greater than 5 fold increase of Tregs over baseline (Treg levels prior to treatment), a greater than 5 fold increase in their Treg/Tconv ratios, and a 61% clinical response rate. Clinical responses were strongly associated with a Treg/Tconv ratio ≥0.2 at the end of the first week of treatment, which was an approximately 2.9 fold increase over the baseline Treg/Tconv ratios. Accordingly, in some embodiments administration of a pharmaceutical composition comprising the molecules of the present disclosure to a subject may increase the Treg/Tconv ratio to at least 0.2, 0.3, 0.4, 0.5, 0.6. 0.7, 0.8, 0.9, 1.0, 1.1, 1.2, 1.3, 1.4 or 1.5. The Treg/Tconv ratio may be maintained at the levels described above over several doses of the molecules of the present disclosure, for example over at least 2, 3, 4, 5, 6, 7, 8, 9, 10, 11, 12, 13, 14, 15, 16, 17, 18, 19 or 20 doses.

Figure 3A:
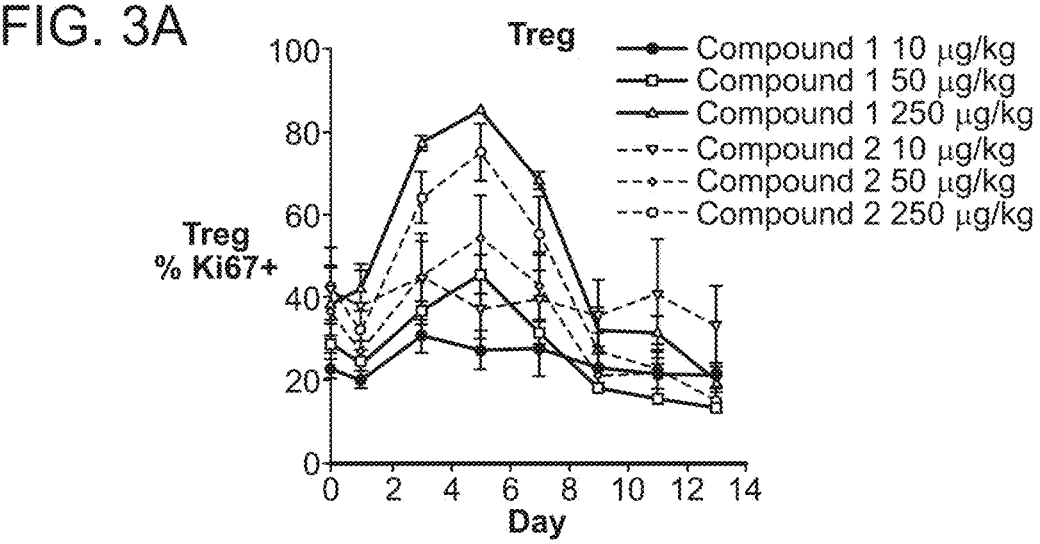
FIG. 3A shows activation of regulatory T cells by Compound 1 and Compound 2 as determined by FACS measurements of the percent of Treg cells expressing Ki67.
Figure 3B:
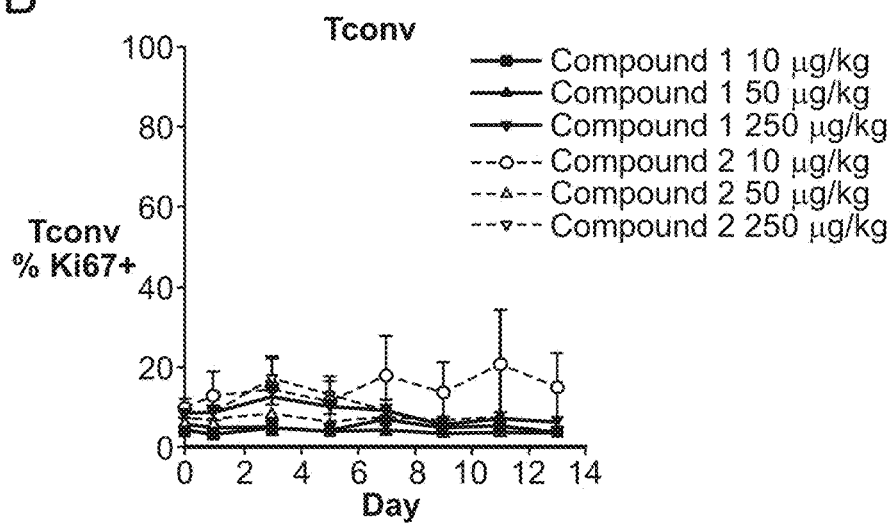
FIG. 3B shows activation of conventional T cells by Compound 1 and Compound 2 as determined by FACS measurements of the percent of Treg cells expressing Ki67.
Figure 3C:
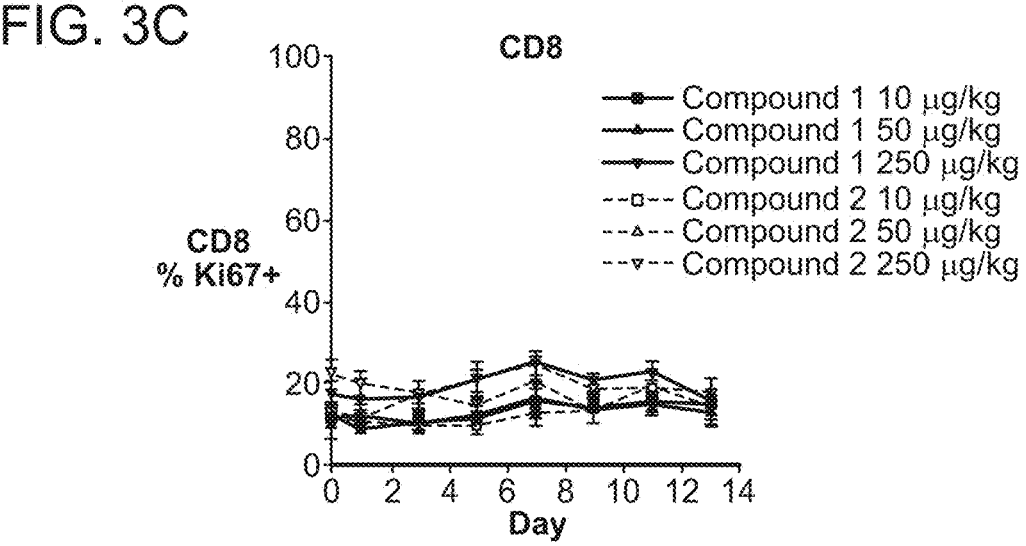
FIG. 3C shows activation of CD8 cells by Compound 1 and Compound 2 as determined by FACS measurements of the percent of Treg cells expressing Ki67.
Figure 4A:
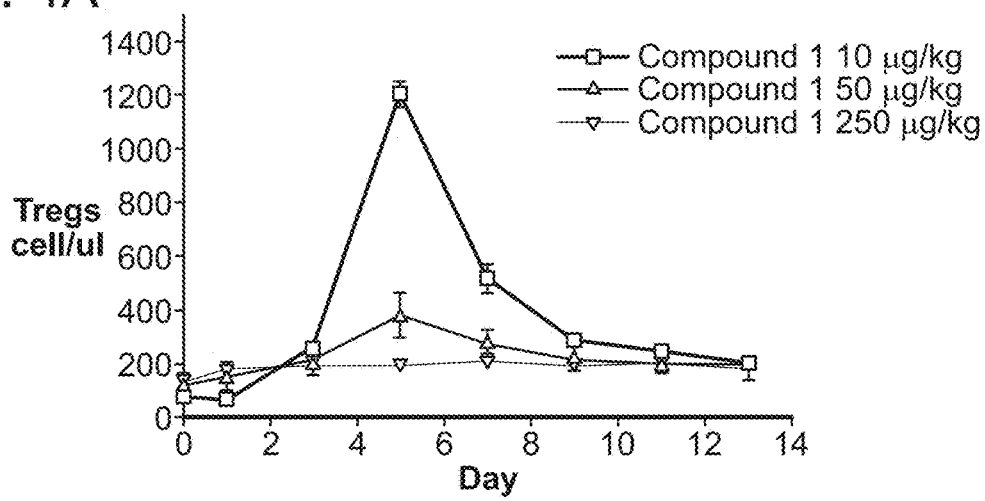
FIG. 4A shows Compound 1's effect on the number of regulatory T cells per μL plasma as determined by flow cytometry.
Figure 4B:
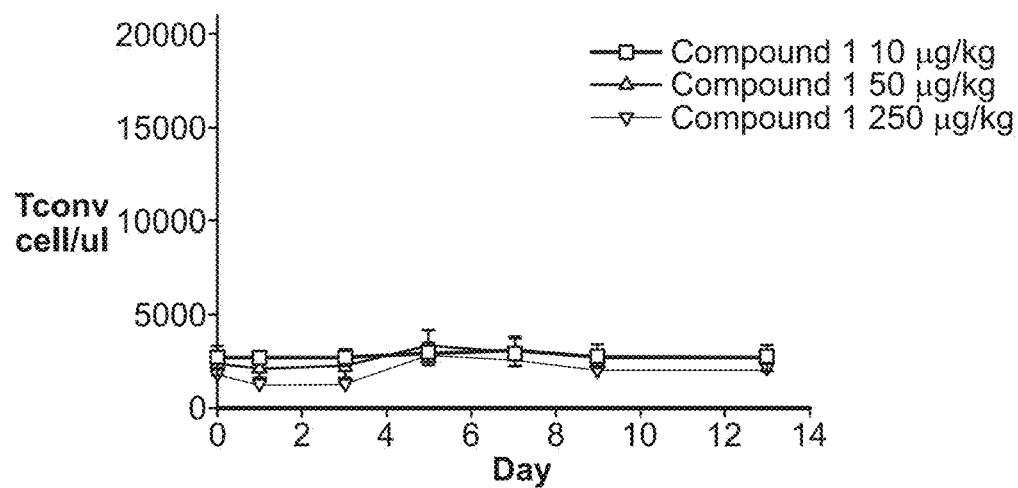
FIG. 4B shows Compound 1's effect on the number of conventional T cells per μL plasma as determined by flow cytometry.
Figure 4C:
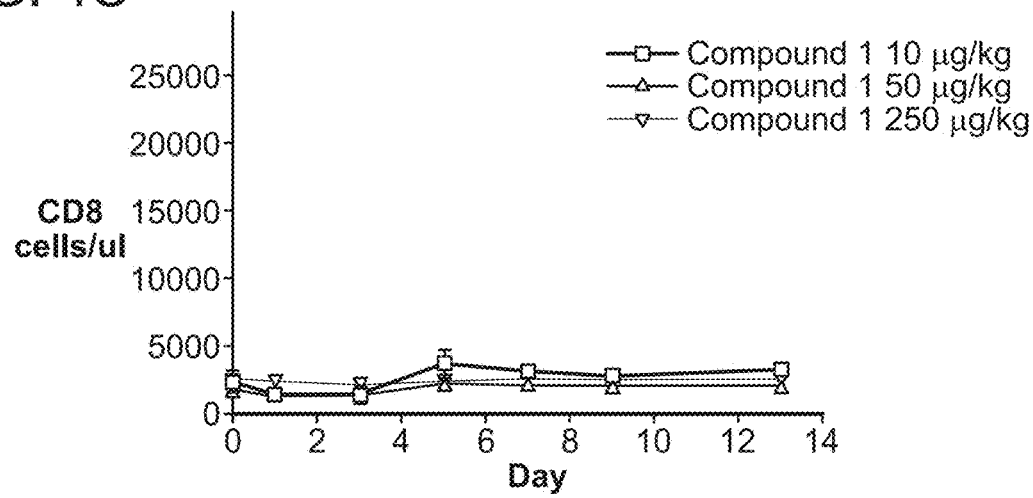
FIG. 4C shows Compound 1's effect on the number of CD8 cells per μL of plasma as determined by flow cytometry.

The molecules of the present disclosure can be highly selective for Tregs and can cause little increase in the count of other immune cells. Immune cells which may not be activated by the molecules of the present disclosure include conventional T cells such as helper T cells and killer T cells, as well as CD8+ T cells, also known as cytotoxic T cells. As shown in FIGS. 3A, 3B, and 3C, treatment of Cynomolgus monkeys with Compound 1 and Compound 2 resulted in a robust and selective induction of proliferation in Treg cells but not in CD4 conventional T cells (Tconv) or CD8+ T cells (CD8). A single intravenous administration of 250 µg/kg of Compound 1 in cynomolgus monkeys caused a more than two fold induction of proliferation in Treg cells. Moreover, Compound 1 and Compound 2 both stimulated a dose-dependent increase in Tregs, with activation of proliferation still above baseline 7 days after administration of a single IV dose in cynomolgus monkeys. A clearer view of the effects of Compound 1 on Treg, Tconv and CD8 cells can be seen in FIGS. 3D, 3E and 3F. As shown in FIGS. 4A, 4B, and 4C, administering Compound 1 to cynomolgus monkeys resulted in a 14.9 fold increase in total circulating Treg cells without increasing the number of circulating Tconv cells or CD8+ cells.

Figure 5A:
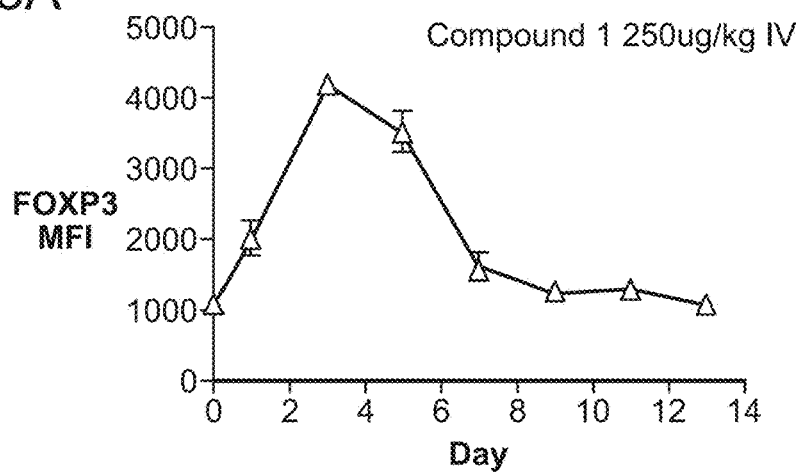
FIG. 5A shows the stimulation of FOXP3 by Compound 1 as determined by flow cytometry (MFI=mean fluorescent intensity).
Figure 5B:
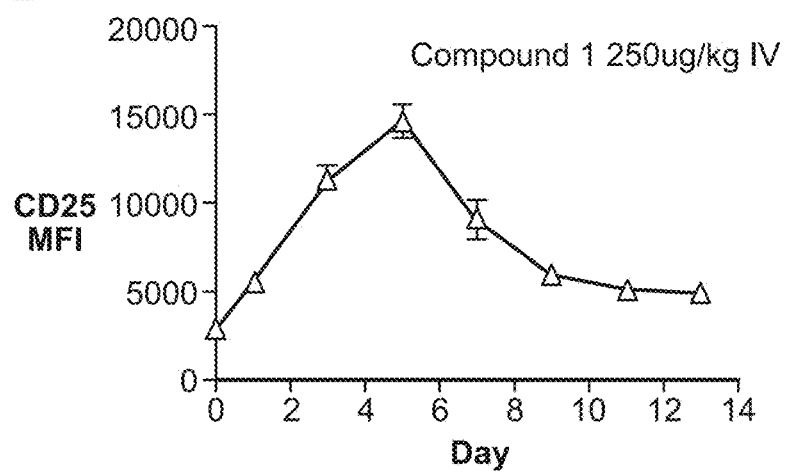
FIG. 5B shows the stimulation of CD25 by Compound 1 (MFI=mean fluorescent intensity) as determined by flow cytometry.
Figure 5C:
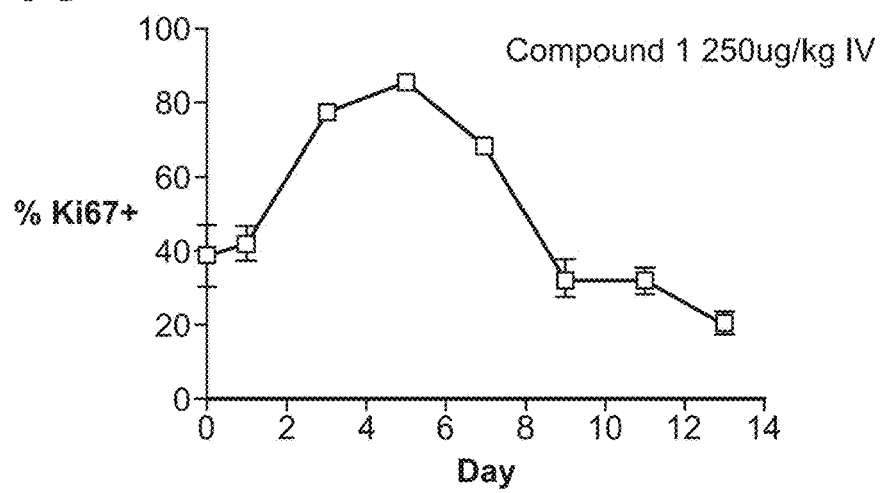
FIG. 5C shows the percentage of cells expressing Ki67 during a course of Compound 1 administration as determined by flow cytometry.
Figure 6:
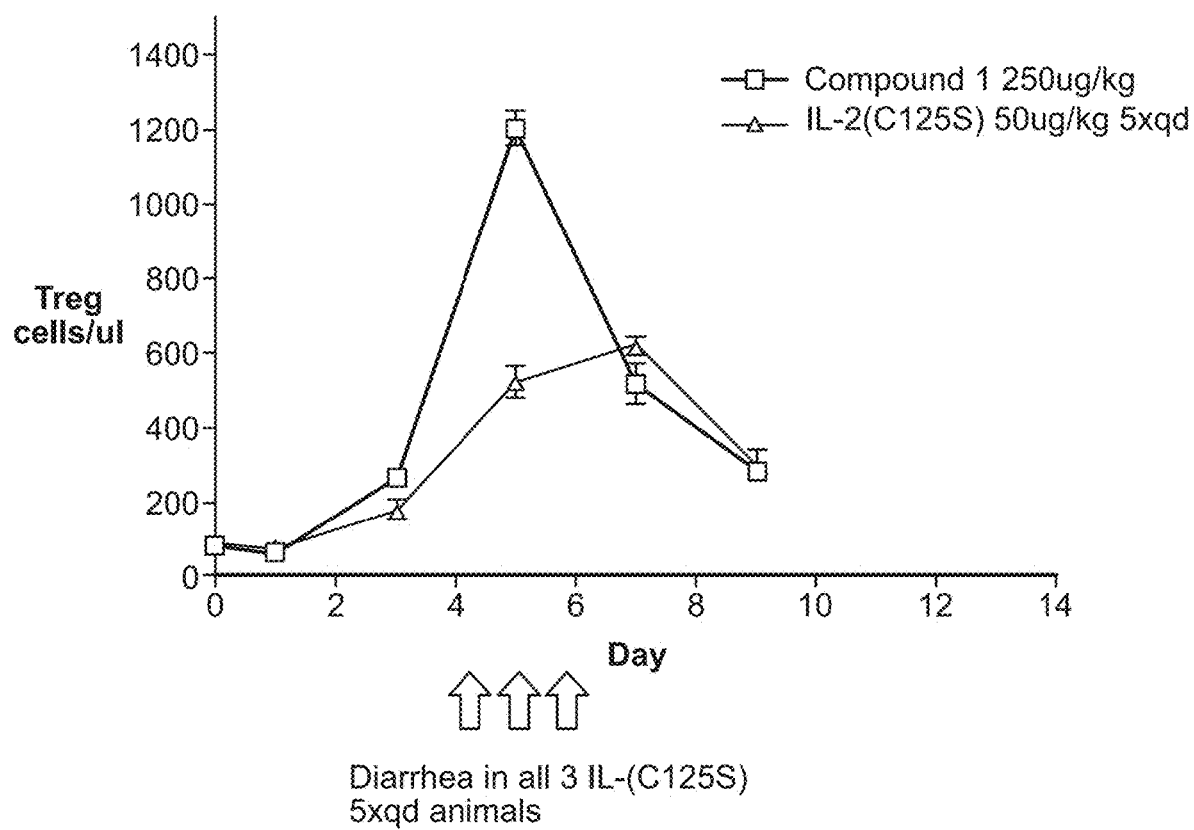
FIG. 6 shows regulatory T cells per μL after treatment with Compound 1 or IL2(C125S) as determined by flow cytometry.
Figure 7:
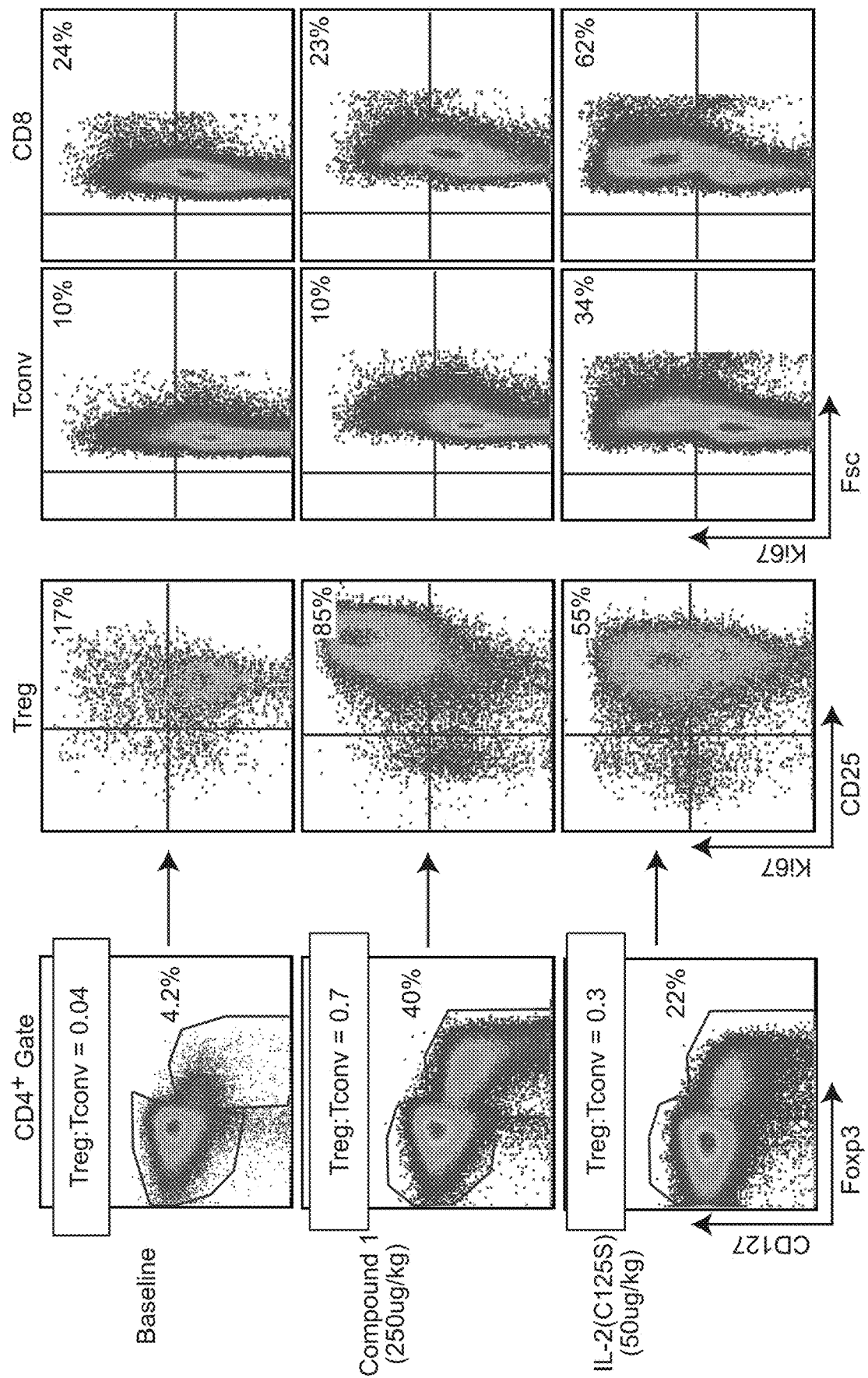
FIG. 7 shows ratios of regulatory T cells to conventional T cells, and expression of markers within those populations from representative animals, on Day 5 of a treatment regimen with Compound 1 or IL2(C125S), as determined by flow cytometry.
Figure 8A:
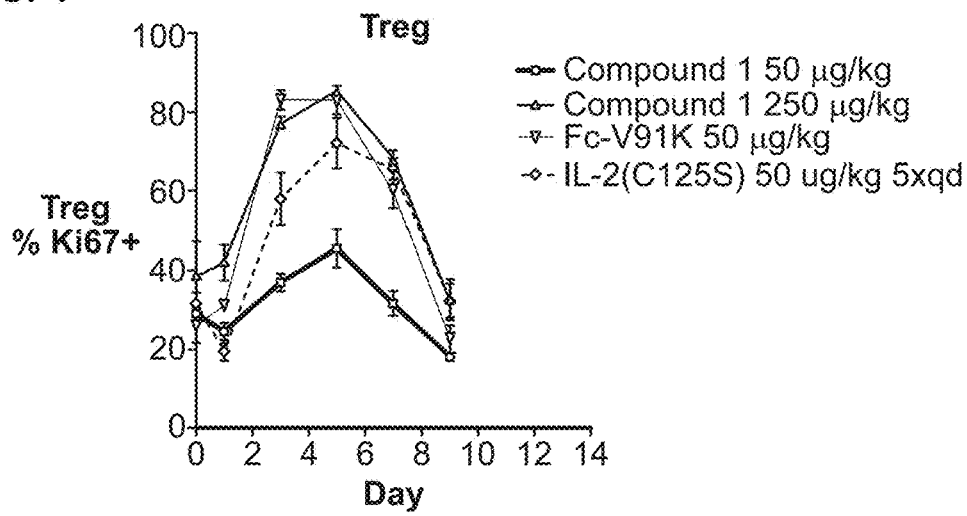
FIG. 8A shows the percentage of regulatory T cells expressing Ki67 during treatment with Compound 1, IL2 (C125S), or Fc-V91K as determined by FACS measurements of the percent of Treg cells expressing Ki67.
Figure 8B:
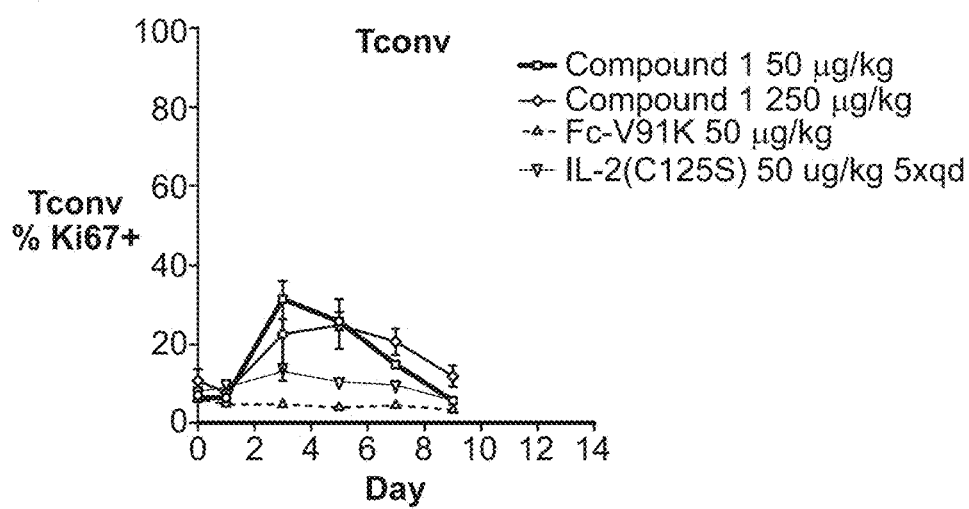
FIG. 8B shows the percentage of conventional T cells expressing Ki67 during treatment with Compound 1, IL2 (C125S), or Fc-V91K as determined by flow cytometry measurements of the percent of Tconv cells expressing Ki67.
Figure 8C:
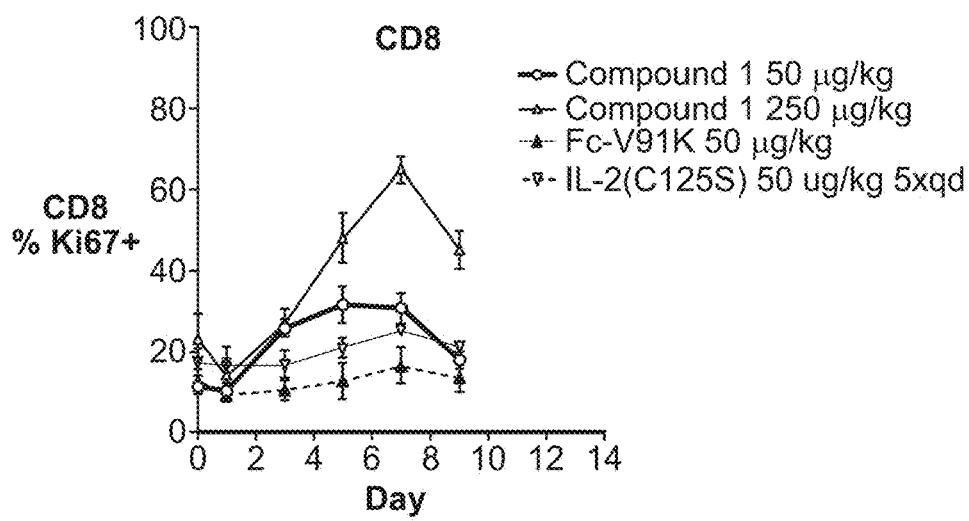
FIG. 8C shows the percentage of CD8 cells expressing Ki67 during treatment with Compound 1, IL2(C125S), or Fc-V91K as determined by FACS measurements of the percent of CD8+ cells expressing Ki67.

The molecules of the present disclosure may also increase regulatory T cell activity (e.g. immunosuppressive activity). Regulatory T cell function may be determined by measuring the expression of one or more biomarkers, including but not limited to, CD25, FOXP3, CTLA-4, ICOS and CD39. For example, treatment of cynomolgus monkeys with 250 µg/kg of Compound 1 resulted in increased expression (as measured by Mean Fluorescence Intensity, or MFI) of FOXP3 and CD25 as shown in FIGS. 5A and 5B. The level of FOXP3, a protein that is necessary for Treg function, is correlated with highly suppressive Tregs (Miyara M, et al., Immunity. 2009 Jun. 19; 30(6):899-911). The level of CD25 (IL2RA protein) has been associated with increased IL-2 consumption, a major immunosuppressive mechanism of Tregs (Chinen T, et al., Nat Immunol. 2016 November; 17(11):1322-1333). Thus, treatment with Compound 1 and Compound 2 stimulated immunosuppressive function in Tregs. The percentage of cells expressing the cell division marker Ki67 was also increased, as seen in FIG. 5C. Treatment of cynomolgus monkeys with Compound 1 resulted in a greater induction of Treg cells than treatment with IL2(C125S), as seen in FIG. 6. Furthermore, all the cynomolgus monkeys treated with IL2(C125S) exhibited diarrhea, while no diarrhea was seen in the cynomolgus monkeys treated with Compound 1. The improved induction of Treg cells was also seen when blood from cynomolgus monkeys treated with Compound 1 and IL2(C125S) was analyzed by Flow Cytometry. Blood cells were gated on CD4 expression and separated by CD127 and FOXP3 expression. In baseline untreated blood, the ratio of Treg:Tconv cells was 0.04, as shown in FIG. 7. In blood from animals treated with Compound 1, the ratio of Treg:Tconv cells was 0.7. In blood from animals treated with IL2 (C125S), the ratio of Treg:Tconv cells was 0.3—less than half of the ratio as seen in blood from cynomolgus monkeys treated with Compound 1. Blood from these cynomolgus monkeys was further separated by Ki67 expression and CD25 expression to determine Treg activation, and separated by forward side scatter (Fsc) to determine Tconv and CD8 activation, as shown in FIG. 7. Compound 1 resulted in activation of 85% of Tregs, compared with 17% in untreated blood or 55% activation induced by IL2(C125S). By contrast, Compound 1 did not activate Tconv cells (10% compared to 10% in the untreated blood) or CD8 cells (23% compared to 24% in the untreated blood). However, IL2 (C125S) activated Tconv cells by about three-fold (34% compared to 10% baseline) and CD8 cells by almost three fold (62% compared to 24% baseline). Compound 1 also shows improved selectivity for Treg cells over Tconv and CD8 cells compared to Fc-V91K, a control compound with an Fc domain, a five amino acid peptide linker and IL2 (V91K), as shown in FIGS. 8A-8C.

Treatment of Autoimmune Diseases

The methods of this invention can be applied to various autoimmune or immune-related diseases or conditions, for example to treat such diseases or conditions. Autoimmune diseases include diseases that affect organs such as the heart, kidney, liver, lung, reproductive organs, digestive system, or skin. Autoimmune diseases include diseases that affect glands, including the endocrine, adrenal, thyroid, salivary and exocrine glands, and the pancreas. Autoimmune diseases can also be multi-glandular. Autoimmune diseases can target one or more tissues, for example connective tissue, muscle, or blood. Autoimmune diseases can target the nervous system or eyes, ears or vascular system. Autoimmune diseases can also be systemic, affecting multiple organs, tissues and/or systems. In some embodiments, an autoimmune disease or condition is an inflammatory disease or condition.

Non-limiting examples of autoimmune or immune-related diseases or conditions include inflammation, antiphospholipid syndrome, systemic lupus erythematosus, rheumatoid arthritis, autoimmune vasculitis, celiac disease, autoimmune thyroiditis, post-transfusion immunization, maternal-fetal incompatibility, transfusion reactions, immunological deficiency such IgA deficiency, common variable immunodeficiency, drug-induced lupus, diabetes mellitus, Type I diabetes, Type II diabetes, juvenile onset diabetes, juvenile rheumatoid arthritis, psoriatic arthritis, multiple sclerosis, immunodeficiency, allergies, asthma, psoriasis, atopic dermatitis, allergic contact dermatitis, chronic skin diseases, amyotrophic lateral sclerosis, chemotherapy-induced injury, graft-vs-host diseases, bone marrow transplant rejection, Ankylosing spondylitis, atopic eczema, Pemphigus, Behcet's disease, chronic fatigue syndrome fibromyalgia, chemotherapy-induced injury, myasthenia gravis, glomerulonephritis, allergic retinitis, systemic sclerosis, subacute cutaneous lupus erythematosus, cutaneous lupus erythematosus including chilblain lupus erythematosus, Sjogren's syndrome, autoimmune nephritis, autoimmune vasculitis, autoimmune hepatitis, autoimmune carditis, autoimmune encephalitis, autoimmune mediated hematological diseases, lc-SSc (limited cutaneous form of scleroderma), dc-SSc (diffused cutaneous form of scleroderma), autoimmune thyroiditis (AT), Grave's disease (GD), myasthenia gravis, multiple sclerosis (MS), ankylosing spondylitis, transplant rejection, immune aging, rheumatic/autoimmune diseases, mixed connective tissue disease, spondyloarthropathy, psoriasis, psoriatic arthritis, myositis, scleroderma, dermatomyositis, autoimmune vasculitis, mixed connective tissue disease, idiopathic thrombocytopenic purpura, Crohn's disease, human adjuvant disease, osteoarthritis, juvenile chronic arthritis, a spondyloarthropathy, an idiopathic inflammatory myopathy, systemic vasculitis, sarcoidosis, autoimmune hemolytic anemia, autoimmune thrombocytopenia, thyroiditis, immune-mediated renal disease, a demyelinating disease of the central or peripheral nervous system, idiopathic demyelinating polyneuropathy, Guillain-Barre syndrome, a chronic inflammatory demyelinating polyneuropathy, a hepatobiliary disease, infectious or autoimmune chronic active hepatitis, primary biliary cirrhosis, granulomatous hepatitis, sclerosing cholangitis, inflammatory bowel disease, gluten-sensitive enteropathy, Whipple's disease, an autoimmune or immune-mediated skin disease, a bullous skin disease, erythema multiforme, allergic rhinitis, atopic dermatitis, food hypersensitivity, urticaria, an immunologic disease of the lung, eosinophilic pneumonias, idiopathic pulmonary fibrosis, hypersensitivity pneumonitis, a transplantation associated disease, graft rejection or graft-versus-host-disease, psoriatic arthritis, psoriasis, dermatitis, polymyositis/dermatomyositis, toxic epidermal necrolysis, systemic scleroderma and sclerosis, responses associated with inflammatory bowel disease, ulcerative colitis, respiratory distress syndrome, adult respiratory distress syndrome (ARDS), meningitis, encephalitis, uveitis, colitis, glomerulonephritis, allergic conditions, eczema, conditions involving infiltration of T cells and chronic inflammatory responses, atherosclerosis, autoimmune myocarditis, leukocyte adhesion deficiency, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, mysathenia gravis, antigen-antibody complex mediated diseases, anti-glomerular basement membrane disease, anti-phospholipid antibody syndrome, allergic neuritis, Bechet disease, Castleman's syndrome, Goodpasture's syndrome, Lambert-Eaton Myasthenic Syndrome, Reynaud's syndrome, Stevens-Johnson syndrome, pemphigoid bullous, pemphigus, autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimmune orchitis and oophoritis, primary hypothyroidism, autoimmune endocrine diseases including autoimmune thyroiditis, chronic thyroiditis (Hashimoto's Thyroiditis), subacute thyroiditis, idiopathic hypothyroidism, Addison's disease, autoimmune polyglandular syndromes (or polyglandular endocrinopathy syndromes), Sheehan's syndrome, autoimmune hepatitis, lymphoid interstitial pneumonitis (HIV), bronchiolitis obliterans (non-transplant) vs NSIP, large vessel vasculitis (including polymyalgia rheumatica and giant cell (Takayasu's) arteritis), medium vessel vasculitis (including Kawasaki's disease and polyarteritis nodosa), ankylosing spondylitis, Berger's disease (IgA nephropathy), rapidly progressive glomerulonephritis, primary biliary cirrhosis, Celiac sprue (gluten enteropathy), cryoglobulinemia, and amyotrophic lateral sclerosis (ALS).

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N, N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after an antibiotic. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Subjects

Subjects can be, for example, elderly adults, adults, adolescents, pre-adolescents, children, toddlers, infants, and non-human animals. In some embodiments, a subject is a patient. Non-human animal subjects can be, for example, a mouse, rat, a chicken, a rabbit, a dog, a cat, or a cow.

Dosing

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi dose containers with a preservative.

A compound described herein can be present in a composition in an amount of about 0.5 µg, about 1 µg, about 2 µg, about 3 µg, about 4 µg, about 5 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 125 µg, about 150 µg, about 175 µg, about 200 µg, about 250 µg, about 300 µg, about 350 µg, about 400 µg, about 450 µg, about 500 µg, about 550 µg, about 600 µg, about 650 µg, about 700 µg, about 750 µg, about 800 µg, about 850 µg, about 900 µg, about 950 µg, about 1000 µg (1 mg), about 1050 µg, about 1100 µg, about 1150 µg, about 1200 µg, about 1250 µg, about 1300 µg, about 1350 µg, about 1400 µg, about 1450 µg, about 1500 µg, about 1550 µg, about 1600 µg, about 1650 µg, about 1700 µg, about 1750 µg, about 1800 µg, about 1850 µg, about 1900 µg, about 1950 µg, about 2000 µg (2 mg), about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 30 mg, about 40 mg, about 50 mg, about 60 mg about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg per dose. Any of these values may be used to define a range for the amount of the compound present in composition. For example, a compound described herein can be present in a composition in a range of from about 0.5 µg to about 750 µg, from about 1 µg to about 500 µg, from about 1 µg to about 250 µg, from about 1 µg to about 25 µg, from about 5 µg to about 50 µg, from about 0.5 µg to about 15 µg, from about 0.5 µg to about 10 µg, from about 1 mg to about 7 mg, or from about 1 mg to about 100 mg per dose.

In some embodiments, a dose can be expressed in terms of an amount of the drug divided by the mass of the subject, for example, micrograms or milligrams of drug per kilograms of subject body mass. In some embodiments, a compound is administered in an amount ranging from about 0.5 µg/kg to about 250 µg/kg, 1 µg/kg to about 200 µg/kg, 5 µg/kg to about 150 µg/kg, about 10 µg/kg to about 100 µg/kg, or about 50 µg/kg to about 100 µg/kg.

The disclosed compounds can be administered at any interval desired. In certain embodiments, the compound is administered once per day. The interval between daily dosing can be any hourly interval, for example, every hour, every 2 hours, every 3 hours, every 4 hours, every 5 hours, every 6 hours, every 7 hours, every 8 hours, every 9 hours, every 10 hours, every 11 hours, or every 12 hours. The administration of the compound can have irregular dosing schedules to accommodate either the person administering the compound or the subject receiving the compound. As such, the compound can be administered, for example, once a day, twice a day, or three times a day.

In some embodiment, the compound is administered less frequently than once per day, for example, once every 2 days, once every 3 days, once every 4 days, once every 5 days, once every 6 days or once every 7 days. In some embodiments, the compound can be administered once a week, 2 times a week, 3 times a week, 4 times a week, 5 times a week, 6 times a week, 7 times a week, 8 times a week, 9 times a week, or 10 times a week.

In certain embodiments, the compound is administered once per week or less frequently than once per week. For example, the compound can be administered once every week, once every 8 days, once every 9 days, once every 10 days, once every 11 days, once every 12 days, once every 13 days, once every 2 weeks, once every 15 days, once every 16 days, once every 17 days, once every 18 days, once every 19 days, once every 20 days, once every 3 weeks, once every 22 days, once every 23 days, once every 24 days, once every 25 days, once every 26 days, once every 27 days, once every 4 weeks, once every 5 weeks, once every 6 weeks, once every 7 weeks, or once every 8 weeks. In some embodiments, the interval between dosing of the IL2 compound is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 days.

1 or Compound 2) are evaluated in cynomolgus monkeys. For example, Compound 2 (IL2 T3A/N88R/C125S—15 amino acid peptide linker—Fc) or aldesleukin (IL-2 C125S) may be administered to cynomolgus monkeys to compare the effects on immune cell populations. The compounds may be administered by subcutaneous injection (SC) at the doses described below in Table 1A.

TABLE 1A

Treatment groups and doses

| Group | No. of Animals | Day(s) of Dosing | Test Article | Dose (µg/kg) | Route |
|---|---|---|---|---|---|
| 1 | 6 | 1 and 8 | CC92252 | 200 | SC |
| 2 | 6 | 1 and 15 | CC92252 | 200 | |
| 3 | 3 | 1 and 8 | aldesleukin | 36.9 | |

Whole blood samples may be collected at the following time points for immune cell analysis:
Groups 1 and 3: Days 1 (Predose), 4, 6, 8 (Predose), 10, 11, 12, 13, 15, 17 and 19;
Group 2: Days 1 (Predose), 4, 6, 8 (Predose), 10, 12, 15 (Predose), 18, 20, 22, 24, and 26.
The samples may be analyzed by flow cytometry to determine the levels of immune cells using the flow cytometry panels shown below in Table 1B. The flow cytometry antigens and immune cell populations that may be identified are shown in Table 1C.

TABLE 1B

Flow cytometry panel

| Fluor. | BV421 | BV510 | FITC | PE | perCP Cy5.5 | PE-Cy7 | APC | APC-Cy7 |
|---|---|---|---|---|---|---|---|---|
| Panel 1 | CD20 | CD8 | CD127 | FoxP3 | CD3 | Ki67 | CD25 | CD4 |
| Panel 2 | CTLA-4 | CD39 | CD127 | FoxP3 | CD3 | ICOS | CD25 | CD4 |

TABLE 1C

Flow Cytometry Antigens and Cell Populations

| Antigen Marker(s) | Cell Population Identified |
|---|---|
| CD3+/CD4+/FOXP3+/CD127lo | Treg |
| CD3+/CD4+/CD25hi (set at top 1% of baseline) | CD4/CD25hi |
| CD3+/CD4+/FOXP3−/CD127+ | Tconv |
| CD3+/CD8+ | CD8 |
| CD3−/CD20−/CD8+ | NK |
| CD3+/CD4+/FOXP3+/CD127lo/CD39 MFI | Activated Treg CD39 |
| CD3+/CD4+/FOXP3+/CD127lo./CTLA4 MFI | Activated Treg CTLA-4 |
| CD3+/CD4+/FOXP3+/CD127lo/ICOS MFI | Activated Treg ICOS |
| CD3+/CD4+//FOXP3+/CD127lo/CD25 MFI | Activated Treg CD25 MFI |
| CD3+/CD4+/FOXP3+/CD127lo/Ki67+ | Proliferating Treg |
| CD3+/CD4+/FOXP3−/CD127+/Ki67+ | Proliferating Tconv |
| CD3+/CD8+/Ki67+ | Proliferating CD8 |
| CD3−/CD20−/CD8+/Ki67+ | Proliferating NK |

In certain embodiments, multiple doses of a compound of the invention may be administered to a subject. For example, in certain embodiments, at least 2, 3, 4, 5, 6, 7, 8, 9, 10, 11, 12, 13, 14, 15, 16, 17, 18, 19 or 20 doses of a compound of the invention, or a pharmaceutical composition comprising the compound, are administered to a subject.

Figure 22:
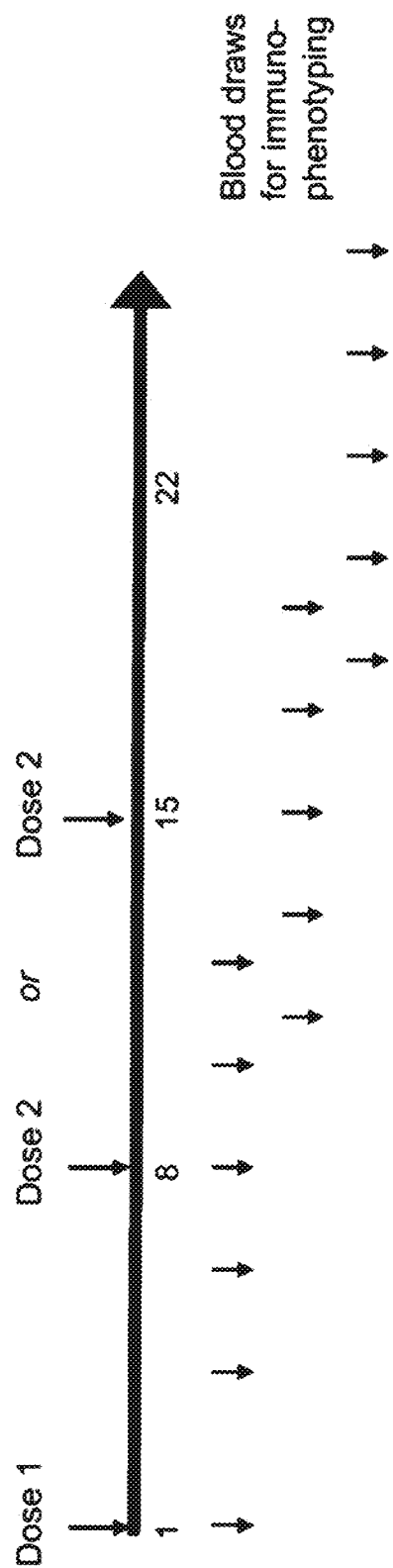
FIG. 22 shows a dosing regimen for an exemplary study comparing once weekly or once every two week dosing of Compound 1 or Compound 2 to aldesleukin (C125S IL-2).
Figure 23:
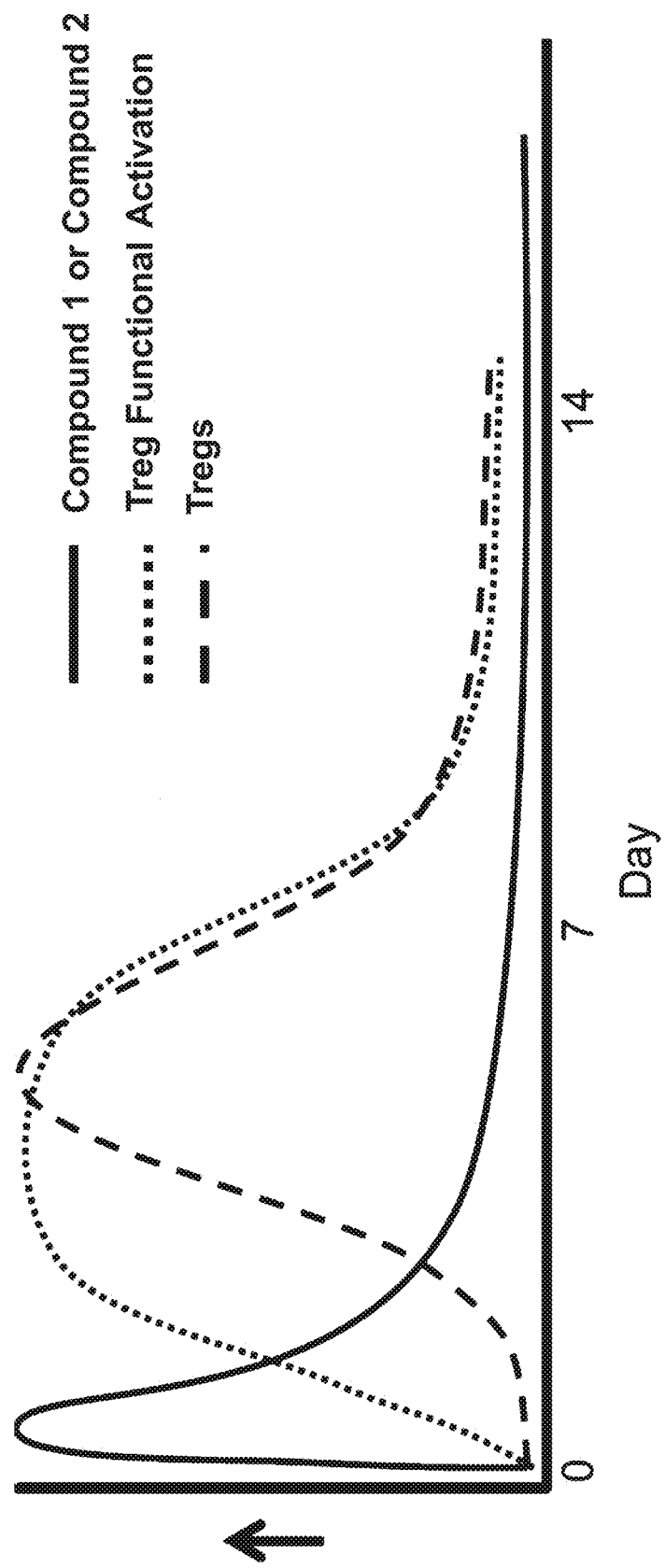
FIG. 23 shows a model to describe the Pharmacokinetic/Pharmacodynamic relationships for Compound 1 and Compound 2. The solid line indicates the levels of Compound 1 or Compound 2. The small dashes indicate regulatory T cell (Treg) functional activation. Large dashes indicate Treg levels.

In a particular embodiment, the effects of infrequent dosing (e.g. once per week or once every 2 weeks) of an IL2 compound comprising the N88R mutation (e.g. Compound An exemplary dosing and sampling schedule for evaluation of Compound 1 or Compound 2 is provided in FIG. 22.

It is expected that when Compound 1 or Compound 2 are administered as subcutaneous doses on day 8, this second dose is near the peak of Treg proliferation, augmentation of Treg numbers, and augmentation of Treg functional activation. When Compound 1 or Compound 2 are administered on day 15, it is expected that augmentation of Treg proliferation numbers, and functional activation have declined close to baseline levels. Exemplary expected results for levels of Compound 1 or Compound 2, regulatory T cell levels, and regulatory T cell activation are provided in Example 23.

In some embodiments, the frequency of dosing may be determined by measuring the levels (e.g. protein or mRNA levels) of biomarkers in the regulatory T cells after administration of a first dose of a compound of the invention. The biomarkers may include, but are not limited to, CD25, FOXP3, CTLA-4 (cytotoxic T-lymphocyte-associated protein 4), ICOS (Inducible T-cell COStimulator), and CD39 (NTPDase1, or Ectonucleoside triphosphate diphosphohydrolase-1). In a particular embodiment, the biomarker is CD25. Biomarker levels may also be determined after subsequent doses of the compound of the invention, for example after a second, third, fourth, fifth, sixth, seventh, eighth, ninth or tenth dose. The biomarker levels may be determined at several time points (e.g. once per day) after administration of the compound of the invention to identify a peak level of the biomarker, i.e. the highest level of the biomarker achieved after administration of a dose of the compound of the invention to the subject, but before administration of a subsequent dose. For example, in some embodiments, biomarker levels are determined at least once, or at least 2, 3, 4, 5, 6, 7, 8, 9 or 10 times after administration of a dose of a compound of the invention to the subject. Biomarker levels may be determined at any interval sufficient to identify the peak level of the biomarker, for example, at least once every 8 hours, at least once every 12 hours, at least once per day, at least once every two days, at least once every 3 days, at least once every 4 days, at least once every 5 days, at least once every 6 days, or at least once per week.

It is expected that levels of the biomarkers will increase after administration of a compound of the invention, reach a peak level, and then decrease from the peak level over time. The subsequent dose may be administered once the level of the biomarker is reduced from the peak level. In some embodiments, the subsequent dose is administered to the subject once the level of the biomarker is reduced by about 5%, 10%, 15%, 20%, 25%, 30%, 35%, 40%, 45%, 50%, 55%, 60%, 65%, 70%, 75%, 80%, 85%, 90%, or 95% relative to the peak level of the biomarker. In some embodiments, the subsequent dose is administered to the subject once the level of the biomarker is reduced by at least about 5%, 10%, 15%, 20%, 25%, 30%, 35%, 40%, 45%, 50%, 55%, 60%, 65%, 70%, 75%, 80%, 85%, 90%, or 95% relative to the peak level of the biomarker. Any of these values may be used to define a range for the percent reduction of the biomarker from peak levels, for example, 5% to 15%, 5% to 25%, or 10% to 50%.

In a particular embodiment, the invention relates to a method for treating an autoimmune disease, the method comprising administering to a subject in need thereof a first dose of a therapeutically-effective amount of a pharmaceutical composition of the invention; measuring expression of a biomarker in a sample obtained from the subject after the first dose has been administered to the subject to determine a peak level of the biomarker; and administering a second dose of a therapeutically-effective amount of the pharmaceutical composition to the subject when the level of the at least one biomarker is reduced by at least 10% relative to the peak level of the biomarker. In some embodiments, the method further comprises collecting a sample from the subject. In certain embodiments, the sample obtained from the subject is a blood sample or a tissue sample (e.g. a skin sample).

The level of the biomarker in the regulatory T cells may be determined by measuring nucleic acid levels (e.g. mRNA levels) or protein levels of the biomarkers. For detecting levels of nucleic acids (e.g. mRNA) encoding the biomarkers, any suitable method can be used, including, but not limited to, Northern blot analysis, polymerase chain reaction (PCR) (see, for example, U.S. Pat. Nos. 4,683,195; 4,683,202, and 6,040,166; "PCR Protocols: A Guide to Methods and Applications", Innis et al. (Eds), 1990, Academic Press: New York), reverse transcriptase PCR (RT-PCR), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320 308), one-sided PCR (Ohara et al., Proc. Natl. Acad. Sci., 1989, 86: 5673-5677), in situ hybridization, quantitative real-time PCR, e.g. Taqman-based assays (Holland et al., Proc. Natl. Acad. Sci., 1991, 88: 7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan®, etc.

In some embodiments, gene expression levels of the biomarkers may be determined by amplifying complementary DNA (cDNA) or complementary RNA (cRNA) produced from mRNA and analyzing it using a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state mRNA level of a large number of genes simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; J. J. Chen et al., Genomics, 1998, 51: 313-324; U.S. Pat. Nos. 5,143,854; 5,445,934; 5,807,522; 5,837,832; 6,040,138; 6,045,996; 6,284,460; and 6,607,885).

Protein levels of the biomarkers in the regulatory T cells may be determined by any suitable method for detecting polypeptides. In certain embodiments, the detection method is an immunodetection method involving an antibody that specifically binds to the biomarker. The steps of various useful immunodetection methods have been described in the scientific literature, such as, e.g., Nakamura et al. (1987). In general, the immunobinding methods include obtaining a sample from the subject containing regulatory T cells, and contacting the sample with an antibody specific for the biomarker to form an immunocomplex. In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241. Methods for detecting protein levels of the biomarkers include but are not limited to flow cytometry, enzyme linked immunosorbent assays (ELISAs), radioimmunoassays (RIA), Western blotting, dot blotting, and protein mass spectrometry.

The amount of the compound of the invention administered to the subject can be the same amount in each dose or the dosage can vary. For example, a first amount can be dosed in the morning and a second amount can be administered in the evening. A subject could receive a high first dose and lower subsequent doses. The dose can be adjusted up or down depending on improvement in symptoms or markers of the disease, or development of adverse reactions.

Pharmaceutical compositions comprising a compound of the invention may further comprise a pharmaceutically-acceptable carrier. Non-limiting examples of pharmaceutically-acceptable carriers include saline, Ringer's solution and dextrose solution. Liquid carriers can be used in preparing solutions, suspensions, and emulsions. A compound described herein can be dissolved or suspended in a pharmaceutically-acceptable liquid carrier such as water, an organic solvent, or a mixture of both, or pharmaceutically-acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for parenteral administration include water, alcohols (including monohydric alcohols and polyhydric alcohols, e.g., glycols) and derivatives thereof, and oils (e.g., fractionated coconut oil and *arachis* oil). For parenteral administration, the carrier can be an oily ester such as ethyl oleate or isopropyl myristate. Sterile liquid carriers are used in sterile liquid form compositions for parenteral administration. In certain embodiments the pH of the solution is about 5.0, 5.5, 6.0, 6.5, 7.0, 7.5 or 8.0. Any of these values may be used to define a range for the pH of the solution. For example, the pH of the solution can be from about 5 to about 8, from about 5 to about 7, from about 5.5 to about 6.5, or from about 7 to about 7.5.

Figure 2A:
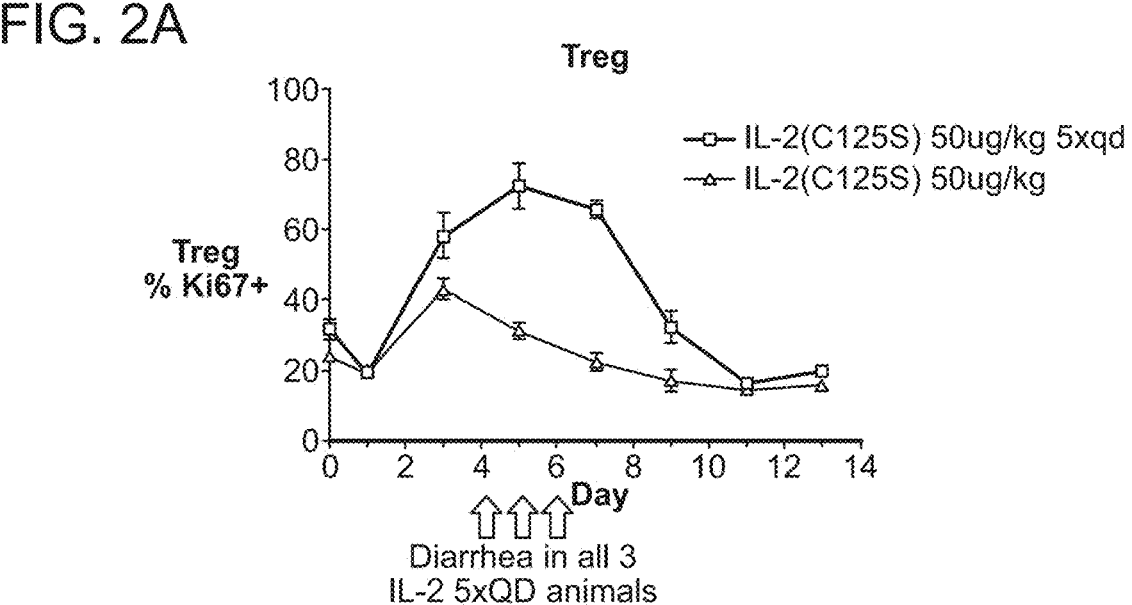
FIG. 2A shows IL2(C125S)'s effect on regulatory T cells as determined by FACS measurements of the percent of Treg cells expressing Ki67.

In some embodiments, treatment with a molecule of the present disclosure is better tolerated than treatment with a wildtype IL-2 polypeptide or a IL-2 (C125S) polypeptide (e.g. aldesleukin). In some embodiments, treatment with a therapeutically-effective dose of a molecule of the present disclosure causes fewer incidents of diarrhea relative to treatment with IL2(C125S) (e.g. aldesleukin). As shown in FIG. 2A, a single dose of IL-2 (IL2(C125S)) was insufficient to induce significant Treg proliferation, but repeated doses caused diarrhea in all animals in the study. By contrast, no adverse reactions were seen in subjects treated with Compound 1 (see FIG. 3A). In some embodiments, treatment with a therapeutically-effective amount of a molecule of the present disclosure does not cause capillary leak syndrome. In some embodiments, treatment with a therapeutically-effective amount of a molecule of the present disclosure does not cause decreased neutrophil activity or increased risk of infection.

Pharmacokinetics

A dose can be modulated to achieve a desired pharmacokinetic (PK) or pharmacodynamics profile, such as a desired or effective blood profile, as described herein.

Pharmacokinetic and pharmacodynamic data can be obtained by various experimental techniques. Appropriate pharmacokinetic and pharmacodynamic profile components describing a particular composition can vary due to variations in drug metabolism in human subjects. Pharmacokinetic and pharmacodynamic profiles can be based on the determination of the mean parameters of a group of subjects. The group of subjects includes any reasonable number of subjects suitable for determining a representative mean, for example, 5 subjects, 10 subjects, 15 subjects, 20 subjects, 25 subjects, 30 subjects, 35 subjects, or more. The mean is determined, for example, by calculating the average of all subject's measurements for each parameter measured. A dose can be modulated to achieve a desired pharmacokinetic or pharmacodynamics profile, such as a desired or effective blood profile, as described herein.

The pharmacodynamic parameters can be any parameters suitable for describing compositions of the invention. For example, the pharmacodynamic profile can be obtained at a time after dosing of, for example, about zero minutes, about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about zero hours, about 0.5 hours, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, about 19.5 hours, about 20 hours, about 20.5 hours, about 21 hours, about 21.5 hours, about 22 hours, about 22.5 hours, about 23 hours, about 23.5 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 60 hours, about 72 hours, about 84 hours, about 96 hours, about 108 hours, about 120 hours, about 132 hours, about 144 hours (7 days), about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, or about 31 days.

The pharmacokinetic parameters can be any parameters suitable for describing a compound. The $C_{max}$ can be, for example, not less than about 1 ng/mL; not less than about 5 ng/mL; not less than about 10 ng/mL; not less than about 15 ng/mL; not less than about 20 ng/mL; not less than about 25 ng/mL; not less than about 50 ng/mL; not less than about 75 ng/mL; not less than about 100 ng/mL; not less than about 200 ng/mL; not less than about 300 ng/mL; not less than about 400 ng/mL; not less than about 500 ng/mL; not less than about 600 ng/mL; not less than about 700 ng/mL; not less than about 800 ng/mL; not less than about 900 ng/mL; not less than about 1000 ng/mL; not less than about 1250 ng/mL; not less than about 1500 ng/mL; not less than about 1750 ng/mL; not less than about 2000 ng/mL; not less than about 2500 ng/mL; or any other $C_{max}$ appropriate for describing a pharmacokinetic profile of a compound described herein. The $C_{max}$ can be, for example, about 5 to about 10,000 ng/mL, about 50 to about 10,000 ng/mL, about 500 to about 10,000 ng/mL, about 5000 to about 10,000 ng/mL, about 1000 to about 5,000 ng/mL, about 1000 to about 3,000 ng/mL, about 5,000 to about 8,000 ng/mL or about 500 to about 1000 ng/mL in blood when administered by intravenous injection, for example, at 50 µg/kg. The $C_{max}$ can be, for example, about 5 to about 50 ng/mL, about 50 to about 500 ng/mL, about 100 to about 250 ng/mL, about 1000 to about 5000 ng/mL, about 1000 to about 2000 ng/mL, about 2000 to about 5000 ng/mL, about 5000 to about 10000 ng/mL or about 5000 to about 7000 ng/mL in blood when administered by subcutaneous injection, for example, at 50 µg/kg. The Cmax may depend on the dose of compound received. The dose received may be 1 µg/kg, 5 µg/kg, 10 µg/kg, 20 µg/kg, 30 µg/kg, 40 µg/kg, 50 µg/kg, 100 µg/kg, 200 µg/kg, 250 µg/kg, 300 µg/kg, 400 µg/kg, 500 µg/kg, 600 µg/kg, 700 µg/kg, 800 µg/kg, 900 µg/kg, 1000 µg/kg, 1500 µg/kg, 2000 µg/kg, 2500 µg/kg or 3000 µg/kg.

The $T_{max}$ of a compound described herein can be, for example, not greater than about 0.5 hours, not greater than about 1 hours, not greater than about 1.5 hours, not greater than about 2 hours, not greater than about 2.5 hours, not greater than about 3 hours, not greater than about 3.5 hours, not greater than about 4 hours, not greater than about 4.5 hours, not greater than about 5 hours, not greater than about 5.5 hours, not greater than about 6 hours, not greater than about 6.5 hours, not greater than about 7 hours, not greater than about 7.5 hours, not greater than about 8 hours, not greater than about 8.5 hours, not greater than about 9 hours, not greater than about 9.5 hours, not greater than about 10 hours, not greater than about 10.5 hours, not greater than about 11 hours, not greater than about 11.5 hours, not greater than about 12 hours, not greater than about 12.5 hours, not greater than about 13 hours, not greater than about 13.5 hours, not greater than about 14 hours, not greater than about 14.5 hours, not greater than about 15 hours, not greater than about 15.5 hours, not greater than about 16 hours, not greater than about 16.5 hours, not greater than about 17 hours, not greater than about 17.5 hours, not greater than about 18 hours, not greater than about 18.5 hours, not greater than about 19 hours, not greater than about 19.5 hours, not greater than about 20 hours, or any other $T_{max}$ appropriate for describing a pharmacokinetic profile of a compound described herein. The $T_{max}$ can be, for example, about 0.1 hours to about 24 hours; about 0.1 hours to about 0.5 hours; about 0.5 hours to about 1 hour; about 1 hour to about 1.5 hours; about 1.5 hours to about 2 hour; about 2 hours to about 2.5 hours; about 2.5 hours to about 3 hours; about 3 hours to about 3.5 hours; about 3.5 hours to about 4 hours; about 4 hours to about 4.5 hours; about 4.5 hours to about 5 hours; about 5 hours to about 5.5 hours; about 5.5 hours to about 6 hours; about 6 hours to about 6.5 hours; about 6.5 hours to about 7 hours; about 7 hours to about 7.5 hours; about 7.5 hours to about 8 hours; about 8 hours to about 8.5 hours; about 8.5 hours to about 9 hours; about 9 hours to about 9.5 hours; about 9.5 hours to about 10 hours; about 10 hours to about 10.5 hours; about 10.5 hours to about 11 hours; about 11 hours to about 11.5 hours; about 11.5 hours to about 12 hours; about 12 hours to about 12.5 hours; about 12.5 hours to about 13 hours; about 13 hours to about 13.5 hours; about 13.5 hours to about 14 hours; about 14 hours to about 14.5 hours; about 14.5 hours to about 15 hours; about 15 hours to about 15.5 hours; about 15.5 hours to about 16 hours; about 16 hours to about 16.5 hours; about 16.5 hours to about 17 hours; about 17 hours to about 17.5 hours; about 17.5 hours to about 18 hours; about 18 hours to about 18.5 hours; about 18.5 hours to about 19 hours; about 19 hours to about 19.5 hours; about 19.5 hours to about 20 hours; about 20 hours to about 20.5 hours; about 20.5 hours to about 21 hours; about 21 hours to about 21.5 hours; about 21.5 hours to about 22 hours; about 22 hours to about 22.5 hours; about 22.5 hours to about 23 hours; about 23 hours to about 23.5 hours; or about 23.5 hours to about 24 hours.

The $AUC_{(0-inf)}$ (also called $AUC_{(0-\infty)}$) or $AUC_{(last)}$ of a compound described herein can be, for example, not less than about 1 ng·hr/mL, not less than about 5 ng·hr/mL, not less than about 10 ng·hr/mL, not less than about 20 ng·hr/mL, not less than about 30 ng·hr/mL, not less than about 40 ng·hr/mL, not less than about 50 ng·hr/mL, not less than about 100 ng·hr/mL, not less than about 150 ng·hr/mL, not less than about 200 ng·hr/mL, not less than about 250 ng·hr/mL, not less than about 300 ng·hr/mL, not less than about 350 ng·hr/mL, not less than about 400 ng·hr/mL, not less than about 450 ng·hr/mL, not less than about 500 ng·hr/mL, not less than about 600 ng·hr/mL, not less than about 700 ng·hr/mL, not less than about 800 ng·hr/mL, not less than about 900 ng·hr/mL, not less than about 1000 ng·hr/mL, not less than about 1250 ng·hr/mL, not less than about 1500 ng·hr/mL, not less than about 1750 ng·hr/mL, not less than about 2000 ng·hr/mL, not less than about 2500 ng·hr/mL, not less than about 3000 ng·hr/mL, not less than about 3500 ng·hr/mL, not less than about 4000 ng·hr/mL, not less than about 5000 ng·hr/mL, not less than about 6000 ng·hr/mL, not less than about 7000 ng·hr/mL, not less than about 8000 ng·hr/mL, not less than about 9000 ng·hr/mL, not less than about 10,000 ng·hr/mL, not less than about 11,000 ng·hr/mL, not less than about 12,000 ng·hr/mL, not less than about 13,000 ng·hr/mL, not less than about 14,000 ng·hr/mL, not less than about 15,000 ng·hr/mL, not less than about 16,000 ng·hr/mL, not less than about 17,000 ng·hr/mL, not less than about 18,000 ng·hr/mL, not less than about 19,000 ng·hr/mL, not less than about 20,000 ng·hr/mL, or any other $AUC_{(0-inf)}$ appropriate for describing a pharmacokinetic profile of a compound described herein. The $AUC_{(0-inf)}$ of a compound can be, for example, about 1 ng·hr/mL to about 10,000 ng·hr/mL; about 1 ng·hr/mL to about 10 ng·hr/mL; about 10 ng·hr/mL to about 25 ng·hr/mL; about 25 ng·hr/mL to about 50 ng·hr/mL; about 50 ng·hr/mL to about 100 ng·hr/mL; about 100 ng·hr/mL to about 200 ng·hr/mL; about 200 ng·hr/mL to about 300 ng·hr/mL; about 300 ng·hr/mL to about 400 ng·hr/mL; about 400 ng·hr/mL to about 500 ng·hr/mL; about 500 ng·hr/mL to about 600 ng·hr/mL; about 600 ng·hr/mL to about 700 ng·hr/mL; about 700 ng·hr/mL to about 800 ng·hr/mL; about 800 ng·hr/mL to about 900 ng·hr/mL; about 900 ng·hr/mL to about 1,000 ng·hr/mL; about 1,000 ng·hr/mL to about 1,250 ng·hr/mL; about 1,250 ng·hr/mL to about 1,500 ng·hr/mL; about 1,500 ng·hr/mL to about 1,750 ng·hr/mL; about 1,750 ng·hr/mL to about 2,000 ng·hr/mL; about 2,000 ng·hr/mL to about 2,500 ng·hr/mL; about 2,500 ng·hr/mL to about 3,000 ng·hr/mL; about 3,000 ng·hr/mL to about 3,500 ng·hr/mL; about 3,500 ng·hr/mL to about 4,000 ng·hr/mL; about 4,000 ng·hr/mL to about 4,500 ng·hr/mL; about 4,500 ng·hr/mL to about 5,000 ng·hr/mL; about 5,000 ng·hr/mL to about 5,500 ng·hr/mL; about 5,500 ng·hr/mL to about 6,000 ng·hr/mL; about 6,000 ng·hr/mL to about 6,500 ng·hr/mL; about 6,500 ng·hr/mL to about 7,000 ng·hr/mL; about 7,000 ng·hr/mL to about 7,500 ng·hr/mL; about 7,500 ng·hr/mL to about 8,000 ng·hr/mL; about 8,000 ng·hr/mL to about 8,500 ng·hr/mL; about 8,500 ng·hr/mL to about 9,000 ng·hr/mL; about 9,000 ng·hr/mL to about 9,500 ng·hr/mL; about 9,500 ng·hr/mL to about 10,000 ng·hr/mL; about 10,000 ng·hr/mL to about 10,500 ng·hr/mL; about 10,500 ng·hr/mL to about 11,000 ng·hr/mL; about 11,000 ng·hr/mL to about 11,500 ng·hr/mL; about 11,500 ng·hr/mL to about 12,000 ng·hr/mL; about 12,000 ng·hr/mL to about 12,500 ng·hr/mL; about 12,500 ng·hr/mL to about 13,000 ng·hr/mL; about 13,000 ng·hr/mL to about 13,500 ng·hr/mL; about 13,500 ng·hr/mL to about 14,000 ng·hr/mL; about 14,000 ng·hr/mL to about 14,500 ng·hr/mL; about 14,500 ng·hr/mL to about 15,000 ng·hr/mL; about 15,000 ng·hr/mL to about 15,500 ng·hr/mL; about 15,500 ng·hr/mL to about 16,000 ng·hr/mL; about 16,000 ng·hr/mL to about 16,500 ng·hr/mL; about 16,500 ng·hr/mL to about 17,000 ng·hr/mL; about 17,000 ng·hr/mL to about 17,500 ng·hr/mL; about 17,500 ng·hr/mL to about 18,000 ng·hr/mL; about 18,000 ng·hr/mL to about 18,500 ng·hr/mL; about 18,500 ng·hr/mL to about 19,000 ng·hr/mL; about 19,000 ng·hr/mL to about 19,500 ng·hr/mL; or about 19,500 ng·hr/mL to about 20,000 ng·hr/mL. For example, the $AUC_{(0\text{-}inf)}$ of a compound can be about 8500 ng·hr/mL when administered intravenously at 50 μg/kg or about 4000 ng·hr/mL when administered subcutaneously at 50 μg/kg.

The plasma concentration of a compound described herein can be, for example, not less than about 1 ng/mL, not less than about 5 ng/mL, not less than about 10 ng/mL, not less than about 15 ng/mL, not less than about 20 ng/mL, not less than about 25 ng/mL, not less than about 50 ng/mL, not less than about 75 ng/mL, not less than about 100 ng/mL, not less than about 150 ng/mL, not less than about 200 ng/mL, not less than about 300 ng/mL, not less than about 400 ng/mL, not less than about 500 ng/mL, not less than about 600 ng/mL, not less than about 700 ng/mL, not less than about 800 ng/mL, not less than about 900 ng/mL, not less than about 1000 ng/mL, not less than about 1200 ng/mL, or any other plasma concentration of a compound described herein. The plasma concentration can be, for example, about 1 ng/mL to about 2,000 ng/mL; about 1 ng/mL to about 5 ng/mL; about 5 ng/mL to about 10 ng/mL; about 10 ng/mL to about 25 ng/mL; about 25 ng/mL to about 50 ng/mL; about 50 ng/mL to about 75 ng/mL; about 75 ng/mL to about 100 ng/mL; about 100 ng/mL to about 150 ng/mL; about 150 ng/mL to about 200 ng/mL; about 200 ng/mL to about 250 ng/mL; about 250 ng/mL to about 300 ng/mL; about 300 ng/mL to about 350 ng/mL; about 350 ng/mL to about 400 ng/mL; about 400 ng/mL to about 450 ng/mL; about 450 ng/mL to about 500 ng/mL; about 500 ng/mL to about 600 ng/mL; about 600 ng/mL to about 700 ng/mL; about 700 ng/mL to about 800 ng/mL; about 800 ng/mL to about 900 ng/mL; about 900 ng/mL to about 1,000 ng/mL; about 1,000 ng/mL to about 1,100 ng/mL; about 1,100 ng/mL to about 1,200 ng/mL; about 1,200 ng/mL to about 1,300 ng/mL; about 1,300 ng/mL to about 1,400 ng/mL; about 1,400 ng/mL to about 1,500 ng/mL; about 1,500 ng/mL to about 1,600 ng/mL; about 1,600 ng/mL to about 1,700 ng/mL; about 1,700 ng/mL to about 1,800 ng/mL; about 1,800 ng/mL to about 1,900 ng/mL; or about 1,900 ng/mL to about 2,000 ng/mL.

The pharmacodynamic parameters can be any parameters suitable for describing compositions of the disclosure. For example, the pharmacodynamic profile can exhibit increased Treg cell counts for, for example, about 24 hours, about 48 hours, about 72 hours, or 1 week.

Non-limiting examples of pharmacodynamic and pharmacokinetic parameters that can be calculated for a compound that is administered with the methods of the invention include: a) the amount of drug administered, which can be represented as a dose D; b) the dosing interval, which can be represented as τ; c) the apparent volume in which a drug is distributed, which can be represented as a volume of distribution $V_d$, where $V_d = D/C_0$; d) the amount of drug in a given volume of plasma, which can be represented as concentration $C_0$ or $C_{ss}$, where $C_0$ or $C_{ss} = D/Vd$ and can be represented as a mean plasma concentration over a plurality of samples; e) the half-life of a drug $t_{1/2}$, where $t_{1/2} = \ln(2)/k_e$; f) the rate at which a drug is removed from the body $k_e$, where $k_e = \ln(2)/t_{1/2} = CL/V_d$; g) the rate of infusion required to balance the equation $K_{in}$, where $K_{in} = C_{ss} \cdot CL$; h) the integral of the concentration-time curve after administration of a single dose, which can be represented as $AUC_{0-\infty}$, wherein $$\int_0^\infty C dt,$$

or in steady-state, which can be represented as $AUC\tau,_{ss}$, wherein $$\int_t^{t+\tau} C dt;$$

i) the volume of plasma cleared of the drug per unit time, which can be represented as CL (clearance), wherein $CL = V_d \cdot k_e = D/AUC$; j) the systemically available fraction of a drug, which can be represented as f, where $$f = \frac{AUCpo \cdot Div}{AUCiv \cdot Dpo};$$

k) the peak plasma concentration of a drug after administration $C_{max}$; l) the time taken by a drug to reach $C_{max}$, $t_{max}$; m) the lowest concentration that a drug reaches before the next dose is administered $C_{min}$; and n) the peak trough fluctuation within one dosing interval at steady state, which can be represented as $$\% \, PTF = 100 \cdot \frac{(C\max, ss - C\min, ss)}{Cav, ss} \text{ where } C_{av,ss} = \frac{AUC\tau, ss}{\tau}.$$

The compounds of the present disclosure can have high stability when administered to a subject. The administered compound can have a physiological half-life of greater than about 6 hrs, greater than about 7 hrs, greater than about 8 hrs, greater than about 9 hrs, greater than about 10 hrs, greater than about 11 hrs, greater than about 12 hrs, greater than about 13 hrs, greater than about 14 hrs, greater than about 15 hrs, greater than about 16 hrs, greater than about 17 hrs, greater than about 18 hrs, greater than about 19 hrs, greater than about 20 hrs, greater than about 21 hrs, greater than about 22 hrs, greater than about 23 hrs, greater than about 24 hrs, greater than about 25 hrs, greater than about 26 hrs, greater than about 27 hrs, greater than about 28 hrs, greater than about 29 hrs, greater than about 30 hrs, greater than about 31 hrs, greater than about 32 hrs, greater than about 33 hrs, greater than about 34 hrs, greater than about 35 hrs, greater than about 36 hrs, greater than about 37 hrs, greater than about 38 hrs, greater than about 39 hrs, greater than about 40 hrs, greater than about 41 hrs, greater than about 42 hrs, greater than about 43 hrs, greater than about 44 hrs, greater than about 45 hrs, greater than about 46 hrs, greater than about 47 hrs, greater than about 48 hrs, greater than about 49 hrs, greater than about 50 hrs, greater than about 51 hrs, greater than about 52 hrs, greater than about 53 hrs, greater than about 54 hrs, greater than about 55 hrs, greater than about 56 hrs, greater than about 57 hrs, greater than about 58 hrs, greater than about 59 hrs, greater than about 60 hrs, greater than about 61 hrs, greater than about 62 hrs, greater than about 63 hrs, or greater than about 64 hrs.

Figure 9:
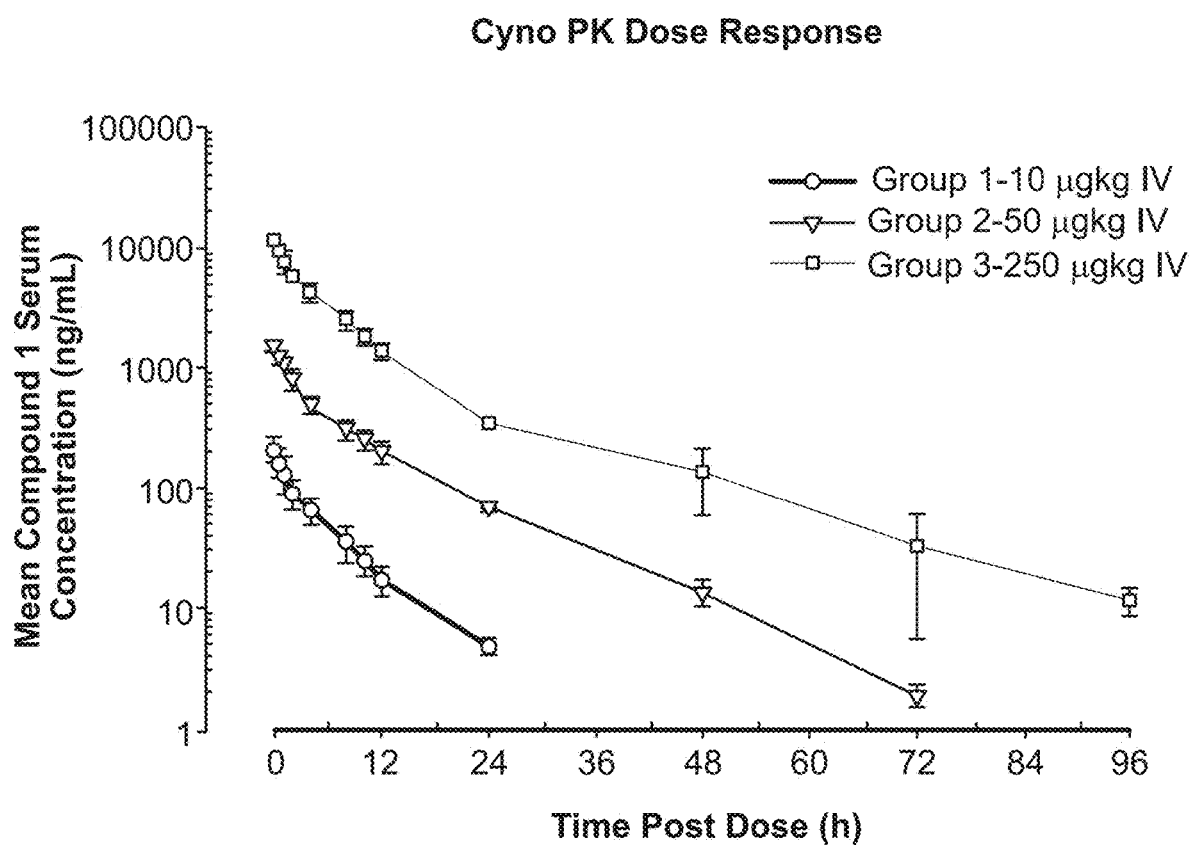
FIG. 9 shows cynomolgus serum concentrations of Compound 1 over time
Figure 10:
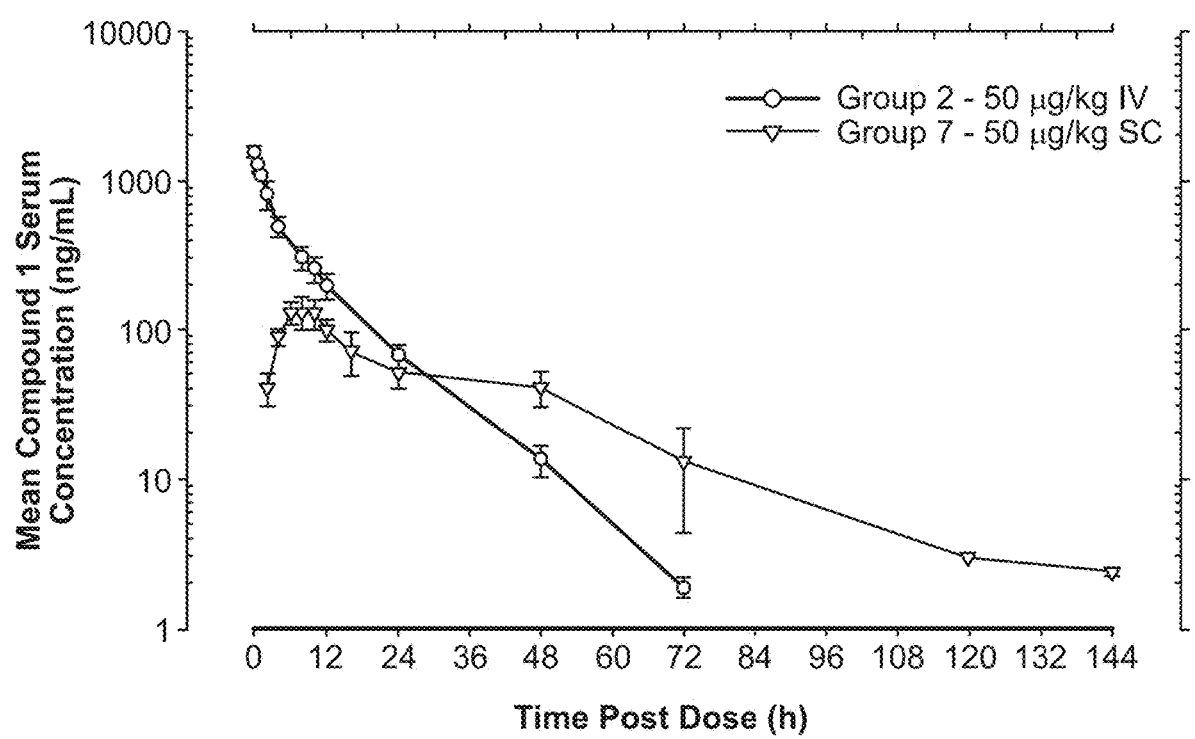
FIG. 10 shows cynomolgus serum concentration of Compound 1 over time with intravenous or subcutaneous dosing.

The half-life of a compound of the present disclosure can vary based on the dose administered. For example, the half-life of the compound when administered in a dose of 50 μg/kg may be shorter than the half-life of the same compound when administered at a dose of 100 μg/kg or 250 μg/kg (see, for example, FIG. 9). The half-life of the compound can vary based on the administration route used. The half-life of the compound can be longer if the compound is administered subcutaneously rather than intravenously. For example the half-life of a compound delivered subcutaneously may be between about 15 hrs and about 25 hrs, while the half-life of the compound delivered intravenously may be between about 5 and about 15 hrs. In some embodiments, the half-life of a compound when administered intravenously at 50 μg/kg is about 6 hrs to about 14 hrs, about 7 hrs to about 13 hours, about 8 hrs to about 12 hrs, or about 9 hrs to about 11 hrs. In some embodiments, the half-life of a compound when administered intravenously at 50 μg/kg is about 5 hrs, about 6 hrs, about 7 hrs, about 8 hrs, about 9 hrs, about 10 hrs, about 11 hrs, about 12 hrs, about 13 hrs, about 14 hrs, or about 15 hrs. In some embodiments, the half-life of a compound when administered subcutaneously at 50 μg/kg is about 15 hrs to about 27 hrs, about 16 hrs to about 26 hours, about 17 hrs to about 25 hrs, about 18 hrs to about 24 hrs, about 19 hrs to about 23 hrs, or about 20 hrs to about 22 hrs. In some embodiments, the half-life of a compound when administered subcutaneously at 50 μg/kg is about 10 hrs, about 11 hrs, about 12 hrs, about 13 hrs, about 14 hrs, about 15 hrs, about 16 hrs, about 17 hrs, about 18 hrs, about 19 hrs, about 21 hrs, about 22 hrs, about 23 hrs, about 24 hrs, about 25 hrs, about 26 hrs, about 27 hrs, about 28 hrs, about 29 hrs, or about 30 hrs. The clearance of the compound from the blood may be faster for a compound delivered intravenously than for a compound delivered subcutaneously. As seen in FIGS. 10A and 10B, Compound 1 had a longer half-life and slower clearance from the blood when injected subcutaneously at 50 μg/kg rather than intravenously at 50 μg/kg.

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

List of Sequences

| SEQ ID NO: | Description |
|---|---|
| 1 | N88R/C125S IL2 (IL2 variant of Compound 1) |
| 2 | Wildtype human IL-2 |
| 3 | T3A/N88R/C125S IL2 (IL2 variant of Compound 2) |
| 4 | N88R/C125S IL2- peptide linker (SEQ ID NO: 6) - Fc (SEQ ID NO: 7)(Compound 1) |
| 5 | T3A/N88R/C125S IL2- peptide linker (SEQ ID NO: 6) - Fc (SEQ ID NO: 7)(Compound 2) |
| 6 | 15 amino acid peptide linker (GGGGSGGGGSGGGGS) |
| 7 | IgG1 Fc region with N297A mutation |

EXAMPLES

Example 1—Evaluation of IL-2 Based Molecules in Cynomolgus Monkeys: Single or Daily Dosing Male cynomolgus monkeys between 3 and 8 years of age were used for this study. The animals were sourced from SNBL USA stock and originated from Cambodia. Animals were identified by unique skin tattoos. At initiation of the experiment, the monkeys had a weight range of 2.5 to 4 kg. Animals were housed in a temperature- and humidity-controlled environment. The targeted range of temperature and relative humidity was between 18 and 29° C. and 30 and 70%, respectively. An automatic lighting system was set to provide a 12-hour light/dark cycle.

Animals were offered PMI LabDiet® Fiber-Plus® Monkey Diet 5049 biscuits twice daily. Animals were fasted as required by specific procedures (e.g., prior to blood draws for serum chemistry, urine collection). The diet was routinely analyzed for contaminants and found to be within manufacturer's specifications. No contaminants were believed to be present at levels that would interfere with the outcome of the study. Fresh drinking water was provided ad libitum to all animals. The water was routinely analyzed for contaminants. Animals were given fruits, vegetables, other dietary supplements, and cage enrichment devices throughout the course of the study per standard operating procedures.

The compounds utilized in this study are listed in Table 1D. Compound 1, Compound 2, REF205, and REF210 were expressed in HEK-293 cells, purified by Protein A chromatography, and further purified by Size Exclusion Chromatography (SEC) by Lakepharma, Inc (Belmont, Calif.). IL-2(C125S) was manufactured by Prometheus, Inc. (San Diego, Calif.).

TABLE 1D

Test compounds

| Test Article | Description |
|---|---|
| Compound 1 | IL2(N88R, C125S)-15 amino acid peptide linker-Fc |
| Compound 2 | IL2(T3A, N88R, C125S)-15 amino acid peptide linker-Fc |
| REF205 | IL2(C125S)-15 amino acid peptide linker-Fc |
| REF210 | Fc-5 amino acid peptide linker-IL2(V91K) |
| IL-2(C125S) | IL-2 control |

Stock solutions of all Fc fusion proteins were determined to have endotoxin levels <1 EU/mg.

It was originally intended that REF205 be tested at the same middle dose level (50 µg/kg) as Compound 1, Compound 2, and REF210. However, after production scale-up, the REF205 protein was determined to be highly aggregated (25.6% monomer) as assessed by SEC, and was not obtained in a yield sufficient to dose at the 50 µg/kg dose level. Therefore, REF205 was instead administered at a dose level of 10 µg/kg.

Because several of the dose levels were administered at relatively low test article protein concentrations, the Fc fusion proteins were all formulated in a buffer containing carrier protein to prevent absorption to surfaces and administration devices. Compound 1, Compound 2, REF205, and REF210 were all formulated in 30 mM HEPES/150 mM NaCl/0.5% vol/vol sterile cynomolgus monkey serum (Bioreclamation Inc., Baltimore, Md.) and stored at −80° C. until administration. Vials of IL-2(C125S) from the manufacturer were reconstituted with 1.2 ml of sterile water for injection to produce a 1.2 ml solution containing 18 MIU (1.1 mg) rhIL-2, 50 mg mannitol and ~180 mcg sodium dodecyl sulphate, buffered with ~170 mcg sodium phosphate monobasic and 890 mcg sodium phosphate dibasic to a pH of 7.5 (range: 7.2-7.8). IL-2(C125S) was further diluted with 5% dextrose in water to the target concentration for injection.

Cynomolgus monkeys were administered single doses or 5 daily doses of the test compounds as illustrated in Table 2. Blood was collected at days 0, 1, 3, 5, 7, 9, 11, and 13, as shown in FIG. 1. Specimens from each subject were drawn into K2 EDTA collection tubes, approximately 0.5 mL each. Specimens were stored at room temperature until processed in the laboratory.

Immuno Staining Procedure for the Identification of Cell Populations in NHP Whole Blood Whole blood (100 µL) was added to fluorochrome-conjugated monoclonal antibodies (Table 3). Samples were mixed and incubated (25-30 minutes) in the dark at 2-8° C. After incubation, leukocytes were isolated by whole blood lysis with 1× BD FACS Lyse (8-12 minutes in the dark at ART) which lyses erythrocytes while preserving the leukocytes. Samples were centrifuged (1700 rpm, 5 minutes, ART with brake) and washed once with 1×DPBS CMF (1 mL). Samples were decanted, mixed and added to 200 µL of Fix/Perm Buffer, before vortexing and incubating for 30-35 minutes in the dark at 2-8° C. Samples were washed twice with 1 mL 1× Perm Buffer (centrifuged as previously described), and resuspended in 100 µL of 1× Perm Buffer with Isotype PECy7: 5 µL/Isotype PE: 5 µL for Tube 1 or Ki67 PECy7: 5 pL/FoxP3 PE: 5 µL for Tube 2 (Tube 1 contains isotype controls and was only be processed for the pretreatment control sample). Samples were mixed and incubated for 30-35 minutes in the dark at 2-8° C. Samples were washed twice with 1 mL 1× Perm Buffer (centrifuge as previously described). Samples were decanted and resuspended in 150 µL 1×DPBS CMF for acquisition on the flow cytometer. Total leukocyte cell numbers were counted with a Hematology Analyzer.

For the flow cytometer, routine fluidics and calibration checks were performed on each day of testing by running BD Cytometer Set-up and Tracking Beads and Spherotech Ultra Rainbow Beads per SOP. Fluorescence compensation to address potential spill-over of one fluorescence signal into another was also conducted at the time of initial instrument setup.

Flow cytometric data acquisition was performed using the FACSCantoII™ which evaluates two scatter parameters and up to eight color fluorescence channels. Data was acquired using BD FACSDiva™ software. Leukocytes were distinguished from other cell types in the peripheral blood by electronic gating on the basis of forward versus side scatter. The instrument was set to collect 100,000 leukocyte events (Tube 1) and 400,000 leukocyte events (Tube 2). Dual combination cytograms were generated to illustrate the P (parameter), LL (−/−), LR (+/−), UL (−/+), and/or UR (+/+) gates.

TABLE 2

Treatment groups and doses

| Group | Test Article | Route | Dose Level (µg/kg) | Concentration (mg/mL) | Volume[a] (mL/kg) | Dose Frequency | Number of Males |
|---|---|---|---|---|---|---|---|
| 1 | Compound 1 | IV | 10 | 0.02 | 0.5 | Day1 | 3 |
| 2 | Compound 1 | IV | 50 | 0.1 | 0.5 | Day1 | 3 |
| 3 | Compound 1 | IV | 250 | 0.5 | 0.5 | Day1 | 3 |
| 4 | Compound 2 | IV | 10 | 0.02 | 0.5 | Day1 | 3 |
| 5 | Compound 2 | IV | 50 | 0.1 | 0.5 | Day1 | 3 |
| 6 | Compound 2 | IV | 250 | 0.5 | 0.5 | Day1 | 3 |
| 7 | Compound 1 | SC | 50 | 0.1 | 0.5 | Day1 | 3 |
| 8 | Compound 2 | SC | 50 | 0.1 | 0.5 | Day1 | 3 |
| 9 | REF205 | IV | 50 | 0.1 | 0.5 | Day1 | 3 |
| 10 | REF210 | IV | 50 | 0.1 | 0.5 | Day1 | 3 |
| 11 | IL-2(C125S) | SC | 50 | 0.2 | 0.5 | Day1 | 3 |
| 12 | IL-2(C125S) | SC | 50 | 0.2 | 0.5 | Days 1 through 5 | 3 |

[a]Total dose volume (mL) was calculated based on animal body weight on Day −1.

TABLE 3

Antibodies used for Flow Cytometry

| Marker | Color | Vendor | Clone |
|---|---|---|---|
| CD127 | FITC | BioLegend | A019D5 |
| FOXP3 | PE | BioLegend | 206D |
| CD25 | APC | eBioscience | CD25-4E3 |
| CD16 | PerCPCy5.5 | BioLegend | 3G8 |
| Ki67 | PECy7 | BD | B56 |
| CD4 | APCH7 | BD | L200 |
| CD8 | V510 | BioLegend | SK1 |
| CD20 | V421 | BioLegend | 2H7 |

The different populations of cells in the blood were identified by expression of known markers, as shown in Table 4.

TABLE 4

Cell Populations measured by flow cytometry

| Subset | Population | Gate | Reported Parameter |
|---|---|---|---|
| Treg | Proportion Treg | CD4+/FOXP3+/CD127− | % of CD4+ |
| Treg | Proliferating Treg | CD4+/FOXP3+/CD127−/Ki67+ | % Ki67+ Treg |
| Treg | Activated Treg | CD4+/FOXP3+/CD127− | FOXP3 MFI |
| Treg | Activated Treg | CD4+/FOXP3+/CD127−/CD25 | CD25 MFI |
| Treg | Absolute cell number | CD4+/FOXP3+/CD127− | Treg/μl blood |
| Tconv | Proportion Tconv | CD4+/FOXP3−/CD127+ | % of CD4+ |
| Tconv | Proliferating Tconv | CD4+/FOXP3−/CD127+/Ki67+ | % Ki67+ Tconv |
| Tconv | Absolute cell number | CD4+/FOXP3−/CD127+ | Tconv/μl blood |
| CD8 | Proportion CD8 | CD8+ | % of lymphocytes |
| CD8 | Proliferating CD8 | CD8+ | % CD8+ Ki67+ |
| CD8 | Absolute cell number | CD8+ | CD8/μl blood |
| B | Proportion B | CD4−/CD8−/CD20+ | % of lymphocytes |
| B | Proliferating B | CD4−/CD8−/CD20+/Ki67+ | % Ki67+ B cells |

The absolute counts of the individual cell subsets were calculated from the relative proportions of the cells (% of lymphocyte subset) X the cellular subset absolute count from the hematology analyzer data.

Figure 2B:
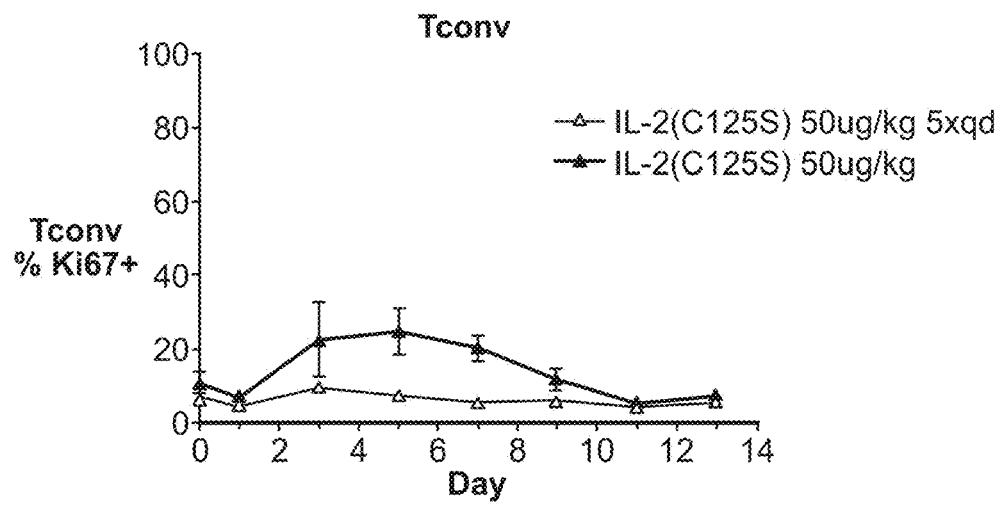
FIG. 2B shows IL2(C125S)'s effect on conventional T cells as determined by FACS measurements of the percent of Treg cells expressing Ki67.
Figure 2C:
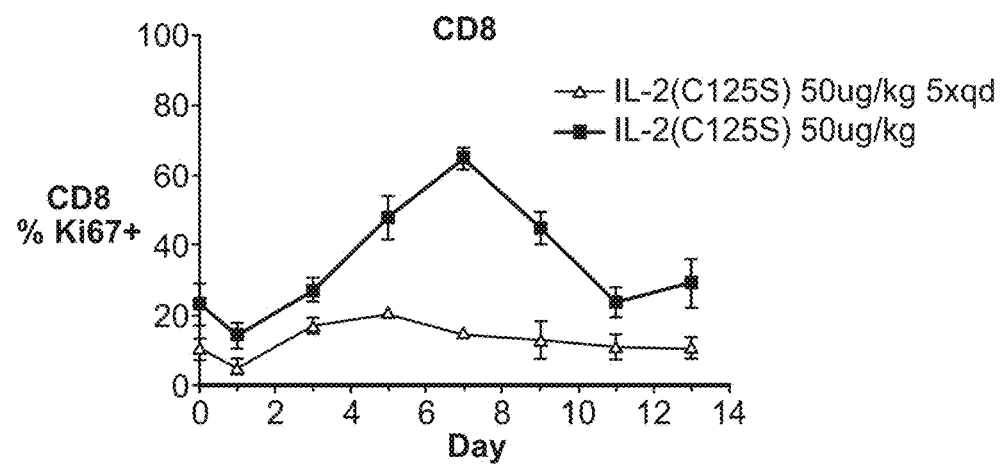
FIG. 2C shows IL2(C125S)'s effect on CD8 cells as determined by FACS measurements of the percent of Treg cells expressing Ki67.

To determine the effect of IL2(C125S) on different cell populations the fraction of each cell type expressing Ki67 (a proliferation marker) was calculated. As shown in FIG. 2A, the single dose of IL-2 only weakly stimulated proliferation of Tregs. The animals receiving the 5 daily doses of IL2 (C125S) showed also increased proliferation of Tregs, but also exhibited significant toxicities. The repeated doses also elicited proliferation in conventional T cells (Tconv cells) (FIG. 2B) and CD8+ cells (FIG. 2C), while the single dose had only a modest effect. By contrast, single dose intravenous treatments with two different compounds of the present disclosure, Compound 1 and Compound 2, caused proliferation of Tregs (FIG. 3A), without activating Tconv (FIG. 3B) or CD8+ cells, (FIG. 3C). Single treatments with 10 μg/kg, 50 μg/kg and 250 μg/kg of Compound 1 and Compound 2 showed dose-dependent increases in proliferation of Tregs.

The total number of Treg cells per μl plasma in the Compound 1 treated monkeys was calculated by multiplying the fraction of cells which are Tregs (as determined by flow cytometry gating by CD4+/FOXP3+/CD127−) by the total number of cells as determined by hematology analysis. As shown in FIG. 4A, the single dose treatment with 250 μg/kg of Compound 1 resulted a 14.9-fold increase in the total number of circulating Treg cells. Lower doses of Compound 1 showed reduced effects on Treg numbers. Treatment with Compound 1 did not result in an increase in Tconv (FIG. 4B, gated by CD4+/FOXP3−/CD127+) or CD8+(FIG. 4C) cells at any dose used.

Treatment with the single dose treatment of 250 μg/kg of Compound 1 also stimulated expression of activation markers FOXP3 (FIG. 5A) and CD25 (FIG. 5B), as seen by an increase in mean fluorescent intensity in FIGS. 5A and 5B, and the percent of Ki67+ cells (FIG. 5C). FOXP3 is a transcription factor required for Treg development and function, CD25 is the IL2Rα receptor subunit, and Ki67 is a cellular marker found exclusively in proliferating cells. The magnitude of all three activation responses were dose-proportional for both Compound 1 and Compound 2. The kinetics for all three activation responses were similar, with activation signals returning close to baseline levels by day 7.

Compound 1 showed enhanced efficacy compared to low dose IL2(C125S). A single dose of the highest doses of Compound 1 or Compound 2 (250 μg/kg) was approximately equivalent on a molar basis to a single dose of IL2(C125S). A single dose of 50 pig/kg of IL2(C125S) is equivalent to 3.3 mol/kg, while a single dose of Compound 1 or Compound 2 is equivalent to 3.0 mol/kg. Six cynomolgus monkeys, three per group, were treated with a single intravenous dose of 250 μg/kg Compound 1 or with five daily subcutaneous doses of 50 μg/kg IL2(C125S). Animals receiving Compound 1 showed a greater peak induction of Treg cells compared to animals receiving IL2(C125S) (see FIG. 6). Although Compound 1 was only administered once compared to the 5 daily injections of IL2(C125S), the duration of the induction of Treg cells was equivalent for the two treatments, both treatments resulted in similar numbers of Tregs at days 7 and 9 of treatment. By way of comparison, Compound 1 exhibited improved therapeutic potency over IL2(C125S), as evidenced by the number of Treg cells per μl of plasma. It is notable that all three animals treated with 5×QD IL2(C125S) were observed to have liquid or soft feces from days 5-7. These findings were considered to be related to the treatment with IL2(C125S) due to the occurrence in all three animals in the treatment group and because the findings occurred after repeated doses of the compound. Diarrhea is the second most common IL2(C125S) adverse events in humans.

Compound 1 resulted in greater Treg activation and more selective Treg activation than did IL2(C125S). The top row of panels of FIG. 7 shows flow cytometry of immune cells from representative animals for the treated groups. Treg cells and Tconv cells can be distinguished by Foxp3 and CD127 expression. In the untreated animal, the ratio of Treg cells to Tconv cells is 0.04. When the immune cells are further analyzed, 17% of the Treg cells express high Ki67 and CD25, indicating activation. 10% of the Tconv cells and 24% of the CD8 cells expressed high Ki67. The second and third panels of FIG. 7 show flow cytometry analysis of immune cells extracted at day 5 from animals treated with either a single dose treatment with 250 µg/kg of Compound 1 or five daily doses of 50 µg/kg IL2(C125S). In the Compound 1-treated animals, the ratio of Treg cells to Tconv cells was 0.7 at day 5, while in the IL2(C125S)-treated animals the ratio was only 0.3. The data corresponded to activation of 85% of Treg cells in Compound 1-treated animals and activation of only 55% of Treg cells in IL2 (C125S)-treated animals. Further activation of Tconv cells and CD8 cells in Compound 1-treated animals was equivalent to activation levels in untreated animals. By contrast, IL2(C125S) caused activation of these cells types. Activation of Tconv cells was up 34% compared to 10% in untreated animals, and activation of CD8 cells was 62% compared with 24% in untreated animals.

The improved Treg activation and selectivity is further demonstrated in FIGS. 8A-8B. FIG. 8A shows Treg activation (Ki67 positive) in blood of animals treated with Compound 1 (50 µg/kg or 250 µg/kg), Fc-V91K, or IL2(C125S). Compound 1 at 250 µg/kg and Fc-V91K at 50 µg/kg showed similar induction of Treg activation. However, as shown in FIGS. 8B and 8C, Fc-V91K resulted in activation of Tconv and CD8 cells. The data suggest that Fc-V91K lacks the selectivity of Compound 1.

Pharmacokinetic Analysis

Test article (Compound 1, Compound 2, IL-2(C125S), REF205, and REF210) concentrations in cynomolgus monkey serum samples were determined using an enzyme-linked immunosorbent assay (ELISA) kit from R&D Systems (Minneapolis, Minn.). The assay kit was designed to quantify Hu-IL-2 in serum sample but worked well with the IL-2 variant molecules tested in this study.

Test article standards, QC controls, and study samples were diluted to the minimum required dilution of 1:5 with assay buffer and incubated with mouse anti-Hu-IL-2 antibodies that had been immobilized onto a 96-well microtiter plate provided by the vendor. After a 2-hour incubation, the plate was washed to remove any unbound substances and an enzyme linked polyclonal antibody specific for Hu-IL-2 was added to the wells. Following another 2-hr incubation and washing, a substrate solution was added and color developed in proportion to the amount of TA bound in the initial step. The color development was stopped 20 minutes after substrate addition and the intensity of the color was measured at 450 nm.

The assay range for Compound 1, Compound 2, and REF205 was 1.25 ng/mL (LLOQ) to 350 ng/mL (ULOQ) in 100% serum. The assay range for REF210 was 0.78 ng/mL (LLOQ) to 200 ng/mL (ULOQ) in 100% serum. The assay range for IL-2 was 0.63 ng/mL (LLOQ) to 40 ng/mL (ULOQ) in 100% monkey serum.

Noncompartmental pharmacokinetic analysis was performed using Phoenix WinNonlin (version 6.3, Certara, L.P., St. Louis, Mo.), in accordance with Dynamikos' Standard Operation Procedures (DCS_SOP-PK-001r1, "PK Analysis of Plasma (Serum) Concentration Time Data" and DCS_SOP-PK-002r1, "Pharmacokinetic/Toxicokinetic Data Analysis by Non-Compartmental Method"). Figures presented in this report were created using SigmaPlot for Windows (13.0, Systat Software Inc., Chicago, Ill.). All toxicokinetic parameters are reported to 3 significant figures, except for Tmax. Dosing on the first day (initiation of treatment) was designated as time 0 for data summary statistics, figures, and pharmacokinetic analysis. Nominal PK sample collection times were used in calculation of summary statistics, and for presentation in figures. Nominal PK sample collection times were used in noncompartmental analysis except when the sample collection time was outside the acceptable deviation range.

Test article serum concentrations that are below the assay's lower limit of quantitation (BLQ) were handled as follows:

BLQ for predose samples were set to zero.

BLQ were set to zero prior to calculation of descriptive statistics. Mean concentrations that are less than LLOQ were not reported.

BLQ were set to 0.00 ng/mL for graphic presentations of individual and mean concentrations.

The following toxicokinetic parameters were estimated:

The maximum observed serum concentration, Cmax, and time of maximum concentration, Tmax, were direct observations from the serum concentration vs time data.

The area under the serum concentration-time curve from time of dosing to the last PK timepoint with quantifiable concentration (AUC0-last) was estimated using the Trapezoidal Method.

The area under the serum concentration-time curve from time of dosing with extrapolation to infinite time (AUC0-∞) was estimated using the Linear Log Trapezoidal Method.

Terminal half-life (t½ λz) was calculated from the first order rate constant associated with the terminal (log-linear) portion of the PK curve (λz). λz was estimated by linear regression of time vs. log concentration.

$$t_{1/2\lambda_z} = \frac{\ln 2}{\lambda_z}$$

Serum clearance (CL) for IV dose was estimated using the first dose administered on Day 1 divided by the resulting AUC0-∞

$$CL = \frac{Dose_{(IV)}}{AUC_{0-\infty}}$$

Serum clearance for SC dose (CL/F) was estimated using the first dose administered on Day 1 or the fifth dose administered on Day 5 divided by the resulting AUC0-∞

$$\frac{CL}{F} = \frac{Dose_{(SC)}}{AUC_{0-\infty}}$$

Volume of distribution based on the terminal phase for IV and SC dose (Vz and Vz/F, respectively) was estimated using λz and AUC(0-∞) of the first and fifth dose $$Vz = \frac{Dose_{(IV)}}{\lambda_z * AUC_{0-\infty}}$$

$$\frac{Vz}{F} = \frac{Dose_{(SC)}}{\lambda_z * AUC_{0-\infty}}$$

Mean residence time (MRT) was estimated using the area under the concentration-time curve and the area under the moment curve $$MRT = \frac{AUMC}{AUC}$$

Subcutaneous (SC) bioavailability (F %) was estimated by comparing AUC(0-∞) from a SC dose to that of the same dose given intravenously $$F(\%) = \frac{AUC_{0-\infty,SC}}{AUC_{0-\infty,IV}} \times 100$$

Pharmacokinetic parameters for Compounds 1 and 2, REF205, REF210 and IL-2(C125S) are shown in Table 5, and a comparison of the pharmacokinetic parameters for Compound 1 and Compound 2 are shown in Table 6.

TABLE 5

Pharmacokinetic parameters for Compound 1

| | Group | | | |
|---|---|---|---|---|
| | 1 | 2 | 3 | 7 |
| | Dose (μg/kg) | | | |
| | 10 | 50 | 250 | 50 |
| | Route | | | |
| PK Parameter | IV | IV | IV | SC |
| | Mean ± Std Dev (n = 3) | | | |
| $AUC_{(0-\infty)}$ (ng·h/mL) | 880 ± 214 | 8520 ± 1040 | 64000 ± 7130 | 4110 ± 745 |
| $C_{max}$ (ng/mL) | 211 ± 48.4 | 1530 ± 130 | 11200 ± 699 | 142 ± 23.2 |
| $T_{max}$ (h) a | 0.033 | 0.033 | 0.033 | 8 |
| CL or CL/F (mL/h-kg) | 11.9 ± 3.23 | 5.93 ± 0.739 | 3.94 ± 0.415 | 12.5 ± 2.37 |
| $t_{1/2}\,\lambda_z$ (h) | 6.25 ± 0.868 | 9.77 ± 0.423 | 15.1 ± 0.526 | 21.1 ± 6.05 |
| F(%) b | NA | NA | NA | 48.2 |

$T_{max}$ for all test articles given via IV injections were at 2 minutes post dose, the first PK blood collection timepoint. For Compound 1, $C_{max}$ increased with IV dose over the dose range of 10 to 250 μg/kg, and the increase was approximately proportional to dose (Table 5). Compound 1 $AUC_{(0-\infty)}$ increased proportional to dose, with a concomitant decrease in mean serum clearance from 11.9±3.23 to 3.94±0.415 mL/h-kg over the dose range of 10 to 250 μg/kg.

The increase for Compound 2 $AUC_{(0-\infty)}$ was approximately proportional to dose similar mean IV clearance values of 10.4±4.73, 6.11±2.33, and 5.50±1.06 ml/h-kg for the 10, 50, and 250 μg/kg doses, respectively (Table 6).

Subcutaneous injection of Compound 1 showed 48% bioavailability and increased half-life compared to intravenous injection (see FIG. 10A and Table 5). A summary of the $AUC_{(0-\infty)}$, Cmax, Tmax, clearance and half-life values for intravenous injection (IV) and subcutaneous injection (SC) of Compounds 1 and 2 is shown in Table 9. $AUC_{(0-\infty)}$ (systemic exposure) were comparable among the 50 μg/kg IV dose for Compound 1, Compound 2, and REF210 with mean values of 8520±1040, 9150±3840, and 11300±2270 ng-h/mL, respectively. Corresponding serum clearance were 5.93±0.739 mL/h-kg for Compound 1, 6.11±2.33 mL/h-kg for Compound 2, and 4.56±0.972 mL/h-kg for REF210.

When given intravenously at a dose of 10 m/kg, the Fc-fusion protein for wild type IL-2(C125S) (REF205) gave similar systemic exposure in comparison to a 10 m/kg IV dose of Compound 1 and Compound 2. Mean $AUC_{(0-\infty)}$ were 669±199, 880±214, and 1180±718 mL/h-kg for REF205, Compound 1, and Compound 2, respectively; and mean serum clearance were 15.9±4.99, 11.9±3.23, and 10.4±4.73 mL/kg, respectively.

When given subcutaneously, Tmax for Compound 1 and Compound 2 was obtained between 6 to 10 hours post dose (Table 5 and Table 9). Mean $AUC_{(0-\infty)}$ obtained for a 50 m/kg given IV and SC gave an estimated bioavailability of 48.2% and 33.0% for Compound 1 and Compound 2, respectively. $T_{1/2\,\lambda_z}$ for the 50 m/kg Compound 1 IV and SC doses were 6.25±0.868 and 21.1±6.05 h, respectively. $T_{1/2\,\lambda_z}$ for the 50 m/kg Compound 2 IV and SC doses were 14.9±3.79 and 24.9±1.94 h, respectively.

Contrasting the SC PK characteristics of Compound 1 and Compound 2 to that of IL-2(C125S) at the same protein dose levels (μg/kg) showed that the former proteins exhibited a lower serum clearance with extension of in vivo circulating half-lives. The mean clearance of Compound 1 and Compound 2 (12.5±2.37 and 22.2±11.4 mL/h-kg, respectively) was 7 to 12 fold higher than that of IL-2(C125S) (151±39.3 mL/h-kg).

Comparing the PK results from subcutaneous administration of Compound 1, Compound 2, and IL2(C125S) clearly showed that Compound 1 and Compound 2 had longer circulating half-lives than IL2(C125S) (Table 8).

TABLE 6

Summary of PK Parameters For Compound 1 and Compound 2 (IV administration)

| | Compound 1 | | | Compound 2 | | |
|---|---|---|---|---|---|---|
| | Dose (µg/kg) | | | | | |
| | 10 | 50 | 250 | 10 | 50 | 250 |
| $AUC_{(0-\infty)}$ (ng-h/mL) | 880 ± 214 | 8520 ± 1040 | 64000 ± 7130 | 1180 ± 718 | 9150 ± 3840 | 46700 ± 9220 |
| $C_{max}$ (ng/mL) | 211 ± 48.4 | 1530 ± 130 | 11200 ± 699 | 190 ± 35.5 | 1440 ± 93.4 | 12600 ± 2150 |
| $T_{max}$ (h) | 0.033 | 0.033 | 0.033 | 0.033 | 0.033 | 0.033 |
| CL or CL/F (mL/h-kg) | 11.9 ± 3.23 | 5.93 ± 0.739 | 3.94 ± 0.415 | 10.4 ± 4.73 | 6.11 ± 2.33 | 5.50 ± 1.06 |
| $t_{1/2} \lambda_z$ (h) | 6.25 ± 0.868 | 9.77 ± 0.423 | 15.1 ± 0.526 | 9.55 ± 8.89 | 14.9 ± 3.79 | 17.0 ± 0.734 |

Compounds 1 and 2 both showed longer half-life, higher Cmax, and greater $AUC_{(0-\infty)}$ than IL-2(C125S), as summarized in Table 8.

TABLE 7

REF205 and REF210 PK parameters

| | Test Article | |
|---|---|---|
| | REF205 | REF210 |
| | Dose (µg/kg) | |
| | 10 | 50 |
| | Route | |
| | IV | IV |
| PK Parameter | Mean ± Std Dev (n = 3) | |
| $AUC_{(0-\infty)}$ (ng-h/mL) | 669 ± 199 | 11300 ± 2270 |
| $C_{max}$ (ng/mL) | 237 ± 34.4 | 966 ± 29.4 |
| $T_{max}$ (h) a | 0.033 | 0.033 |
| CL (mL/h-kg) | 15.9 ± 4.99 | 4.56 ± 0.972 |
| $t_{1/2} \lambda_z$ (h) | 5.35 ± 2.16 | 7.91 ± 0.715 |

TABLE 8

PK parameters for Compound 1, Compound 2 and IL-2(C125S)

| | Test Article | | |
|---|---|---|---|
| | Compound 1 | Compound 2 | IL-2(C125S) |
| | Group | | |
| | 7 | 8 | 11 and 12 |
| | Dose (µg/kg) | | |
| | 50 | 50 | 50 |
| | Route | | |
| | SC | SC | SC |
| PK Parameter | Mean ± SD (n = 3) | | Mean ± SD (n) |
| $AUC_{(0-last)}$ (ng-h/mL) | 4020 ± 759 | 2660 ± 2390 | 224 ± 43.4 (6) |
| $AUC_{(0-\infty)}$ (ng-h/mL) | 4110 ± 745 | 3020 ± 2220 | 355 ± 108 (6) |
| $C_{max}$ (ng/mL) | 142 ± 23.2 | 73 ± 33 | 46.7 ± 10.5 (6) |
| $T_{max}$ (h) a | 8 | 6 | 2 |
| CL/F (mL/h-kg) | 12.5 ± 2.37 | 22.2 ± 11.4 | 151 ± 39.3 (6) |
| $t_{1/2} \lambda_z$ (h) | 21.1 ± 6.05 | 24.9 ± 1.94 | 4.32 ± 2.22 (6) |
| Vz/F (mL/kg) | 368 ± 71.8 | 775 ± 369 | 859 ± 265 (6) |
| MRT (h) | 33.6 ± 8.88 | 38.2 ± 3.75 | 6.98 ± 3.08 (6) |
| F(%) b | 48.2 | 33.0 | ND |

TABLE 9

Intravenous and subcutaneous dosing of Compound 1.

| | Compound 1 | | Compound 2 | |
|---|---|---|---|---|
| | Route | | | |
| | IV | SC | IV | SC |
| $AUC_{(0-\infty)}$ (ng-h/mL) | 8520 ± 1040 | 4110 ± 745 | 1180 ± 718 | 3020 ± 2220 |
| $C_{max}$ (ng/mL) | 1530 ± 130 | 142 ± 23.2 | 190 ± 35.5 | 73.0 ± 33.0 |
| $T_{max}$ (h) | 0.033 | 8 | 0.033 | 6 |
| CL or CL/F (mL/h-kg) | 5.93 ± 0.739 | 12.5 ± 2.37 | 10.4 ± 4.73 | 22.2 ± 11.4 |
| $t_{1/2} \lambda_z$ (h) | 9.77 ± 0.423 | 21.1 ± 6.05 | 9.55 ± 8.89 | 24.9 ± 1.94 |
| F(%) | NA | 48.2 | NA | 33.0 |

Figure 11A:
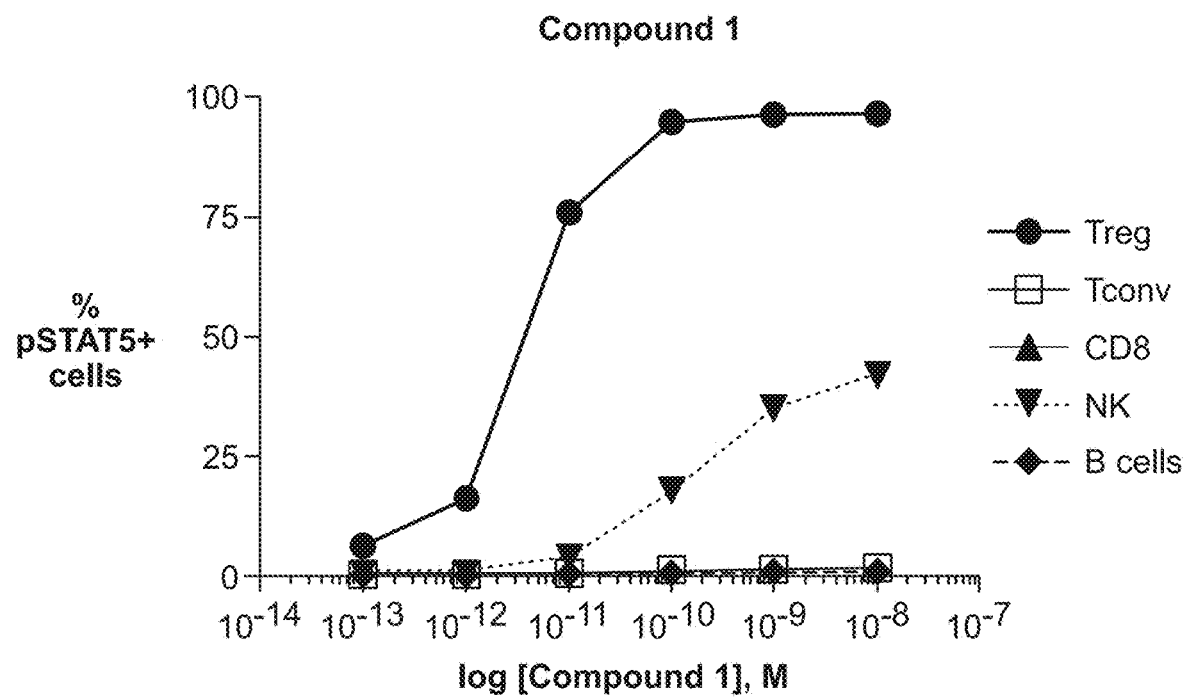
FIG. 11A shows percentage of different cells types expressing pSTAT-5 after treatment with Compound 1.
Figure 11B:
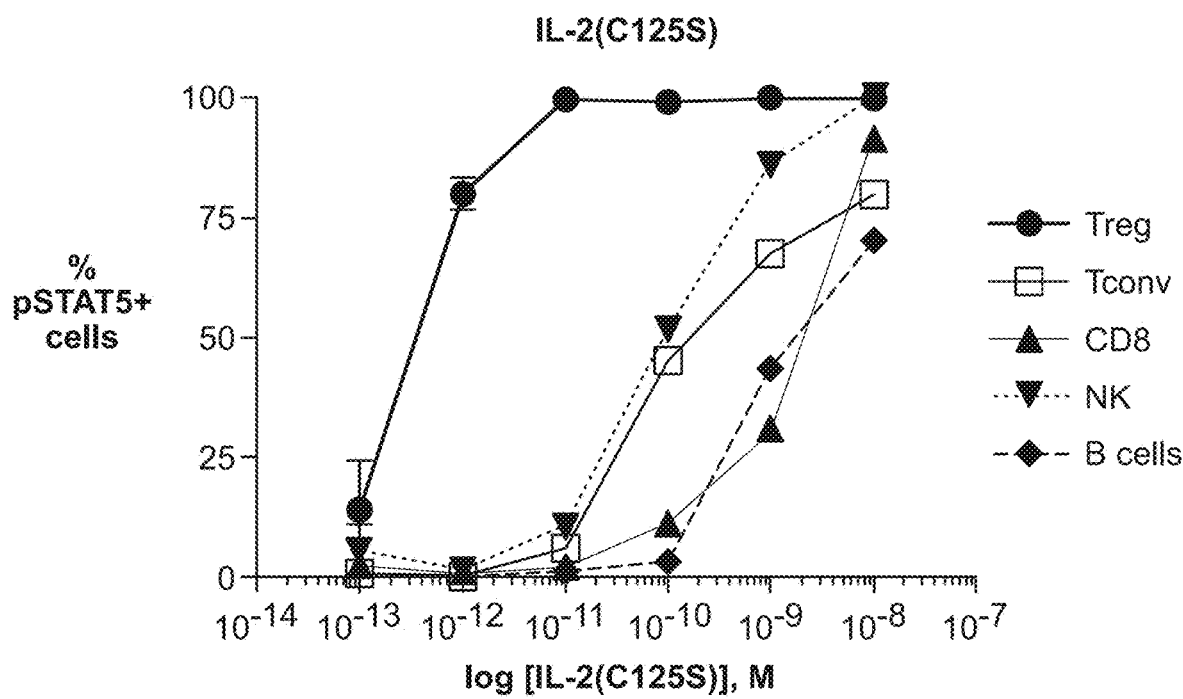
FIG. 11B shows percentage of different cells types expressing pSTAT-5 after treatment with during treatment with IL2(C125S).

A marker for activated immune cells is phosphorylated STAT5 (pSTAT5). Phosphorylation of STAT5 is an essential step in the IL-2 signal transduction pathway, and can be measured by flow cytometry with an antibody specific for pSTAT5. As shown in FIGS. 11A and 11B, Compound 1 showed much greater selectivity for Tregs than for other cells types across a range of doses. Compound 1 demonstrated over 1,000-fold-greater selectivity for Tregs over Tconv and other immune cells. A residual fraction of natural killer (NK) cells responding to Compound 1 are enriched for $CD56^{bright}$ NK cells. Although the Treg EC50 was somewhat higher for Compound 1 (4.1 pmol) than IL2(C125S) (0.7 pmol), IL2(C125S) was selective for Treg cells over a narrow dose range and caused strong activation of other cell types as doses where Compound 1 exhibited selective activation of Treg cells.

Example 2: Compound 1 Activation of Human Immune Cells

Figure 12:
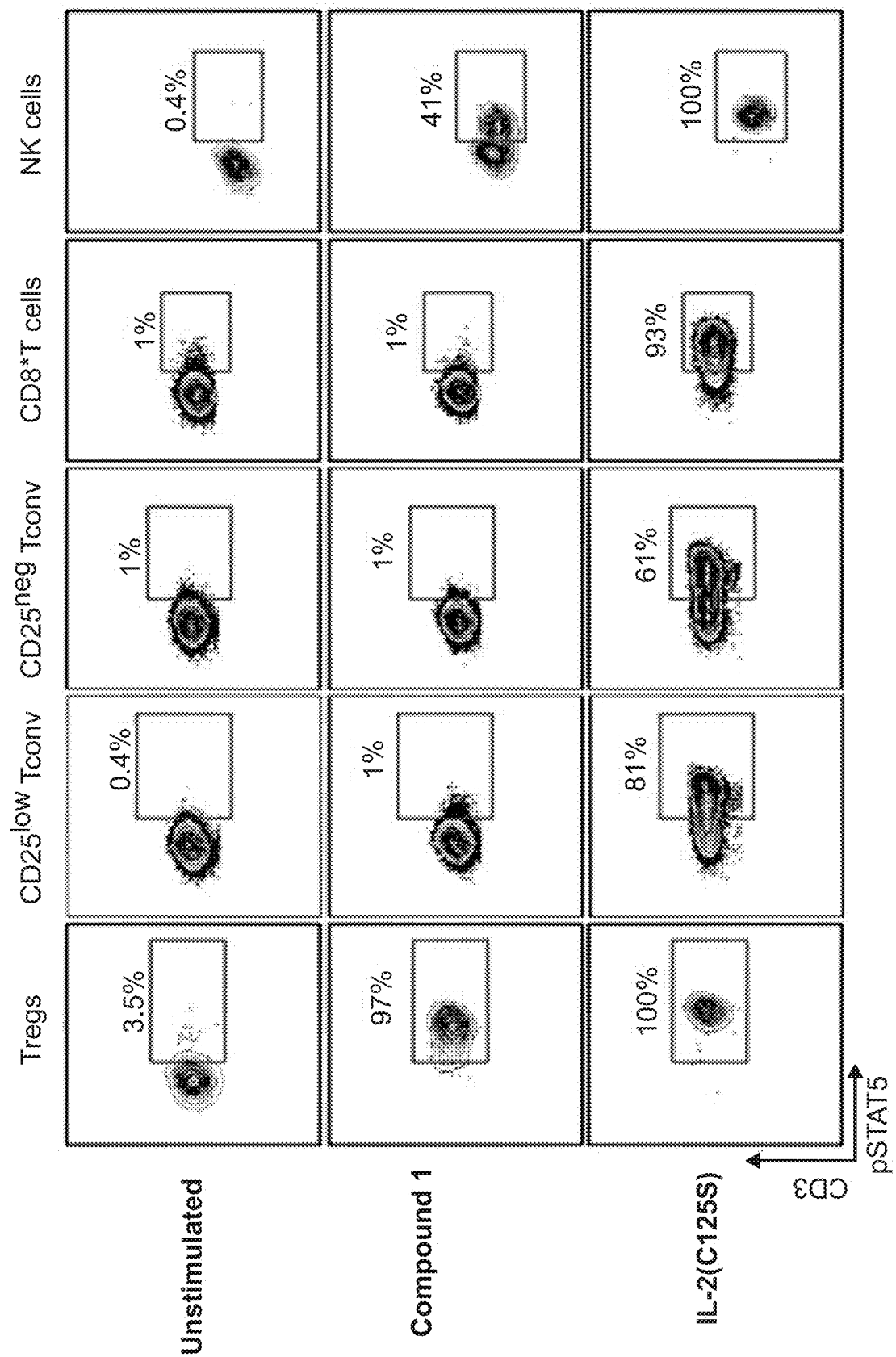
FIG. 12 shows percentages of different human cell types activated by treatment with Compound 1 or IL2(C125S).
Figure 13:
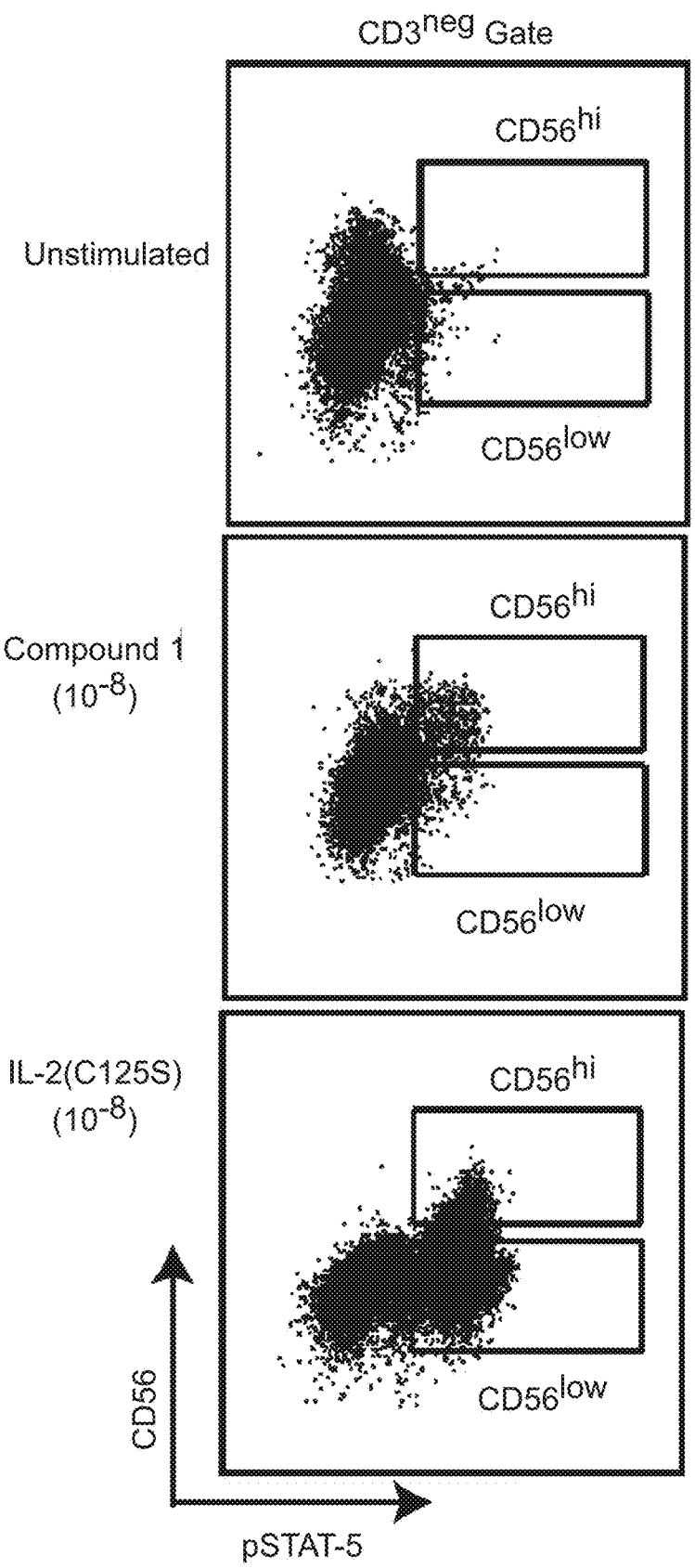
FIG. 13 shows pSTAT-5 and CD56 expression cells treated with Compound 1 or IL2(C125S).
Figure 14A:
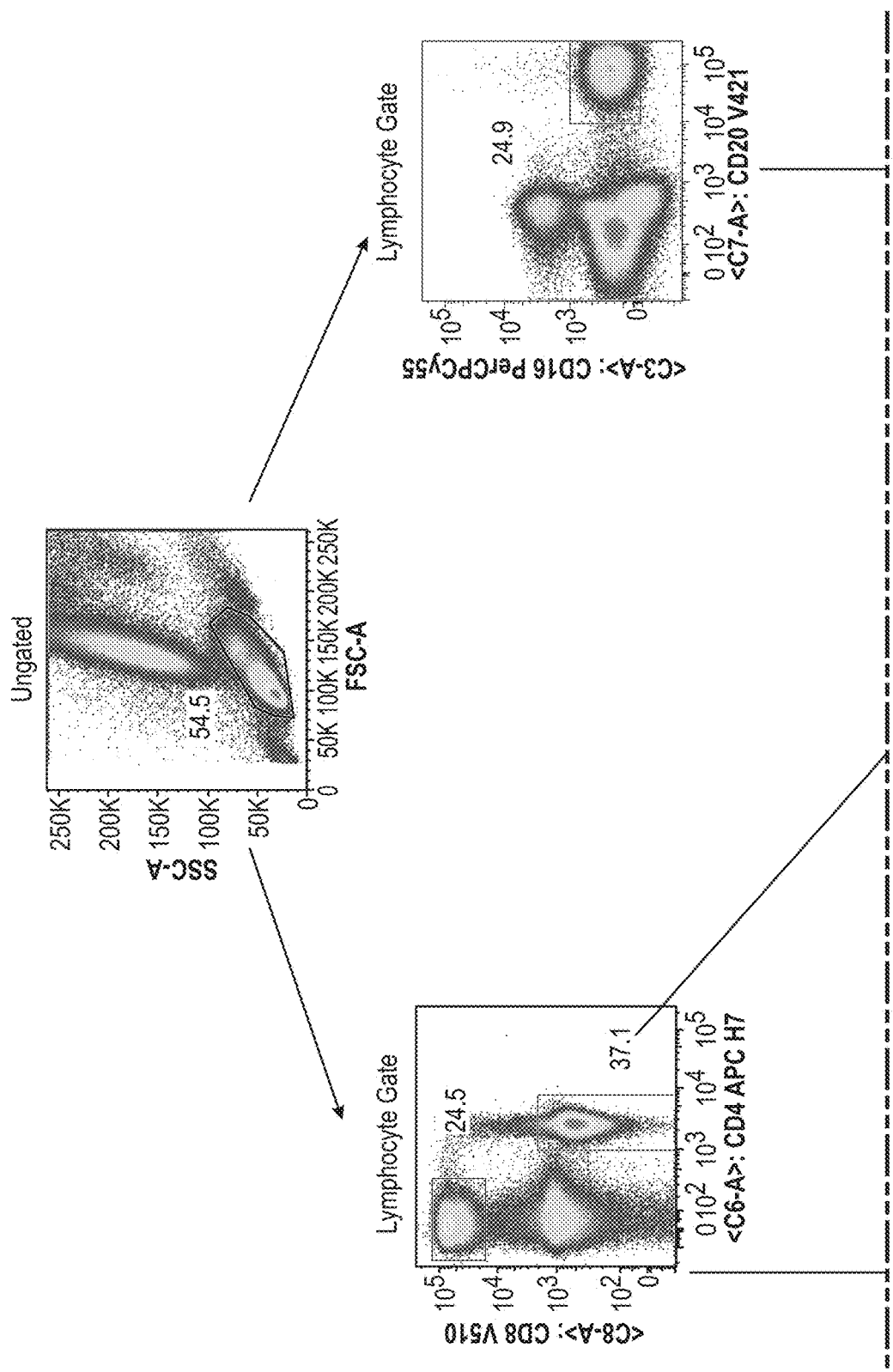
FIGS. 14A, 14B and 14C show a flow cytometry gating strategy to identify different cell types.
Figure 14B:
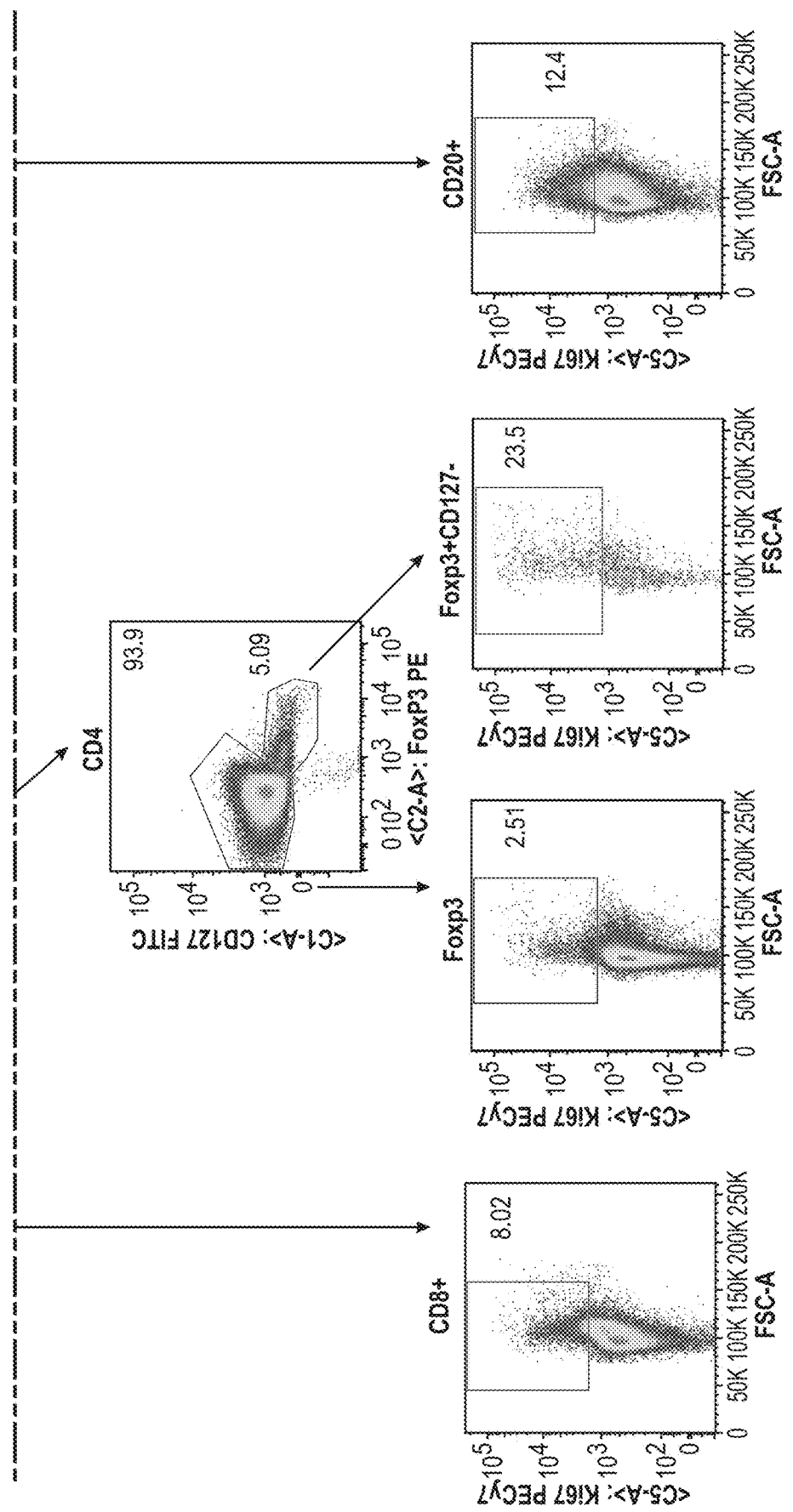
Figure 14C:
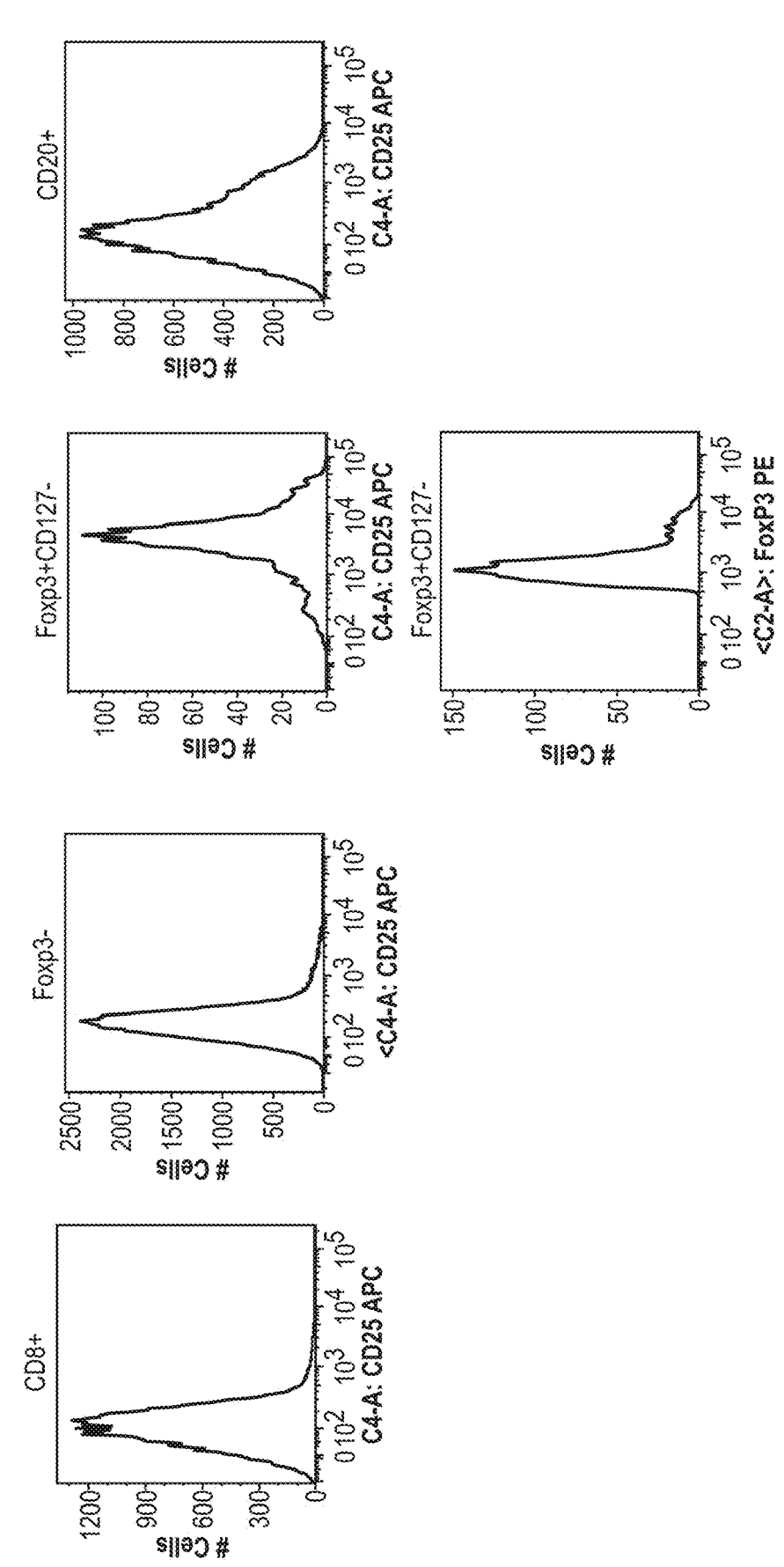
Figure 15:
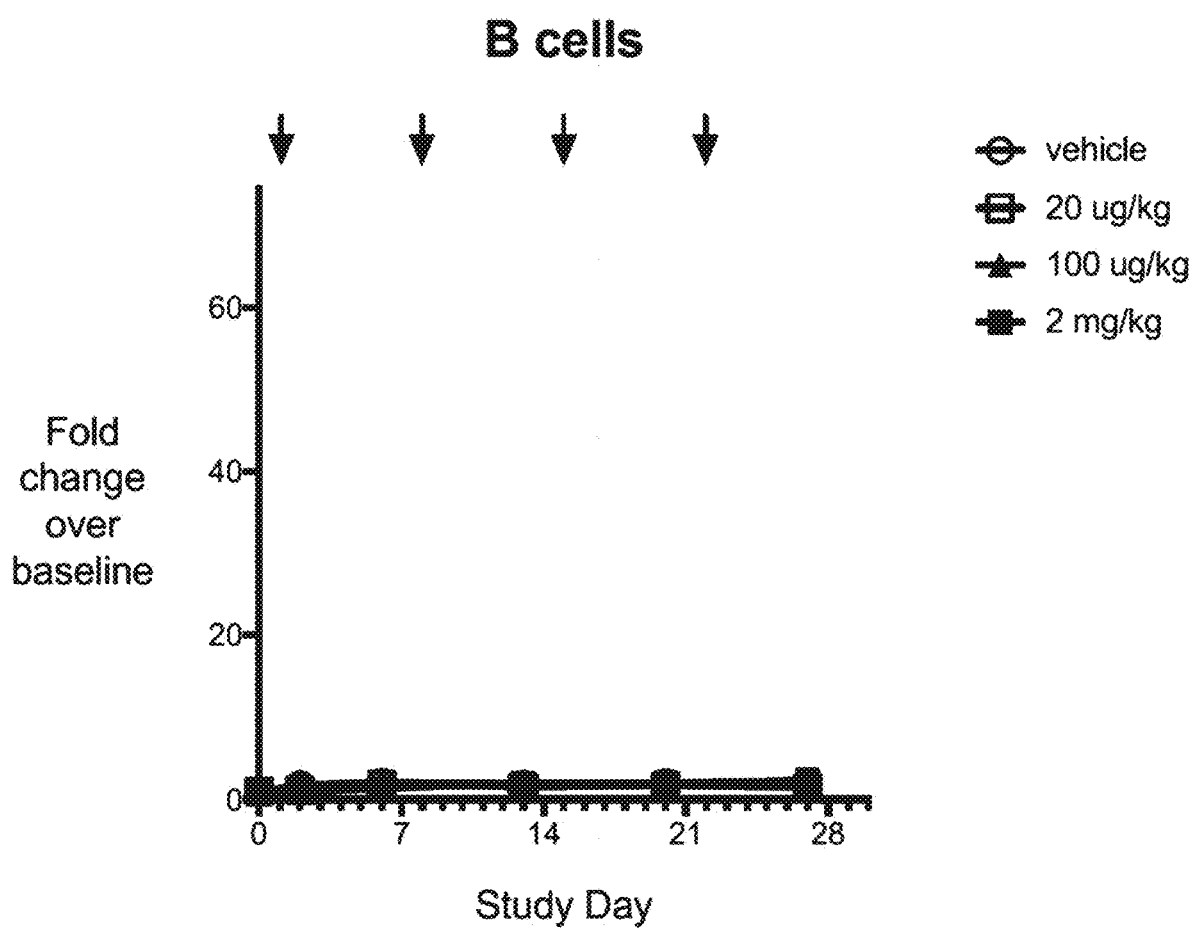
FIG. 15 shows the fold change over baseline of B cell levels in cynomolgus monkeys treated with vehicle or compound 2 (IL2 (T3A, N88R)-15 amino acid peptide linker-Fc) by subcutaneous dosing on days 1, 7, 14, 21, and 28. B cell levels were quantified 5 days after each dose. Compound 2 was administered at doses of 20 µg/kg, 100 µg/kg, or 2 mg/kg.
Figure 16:
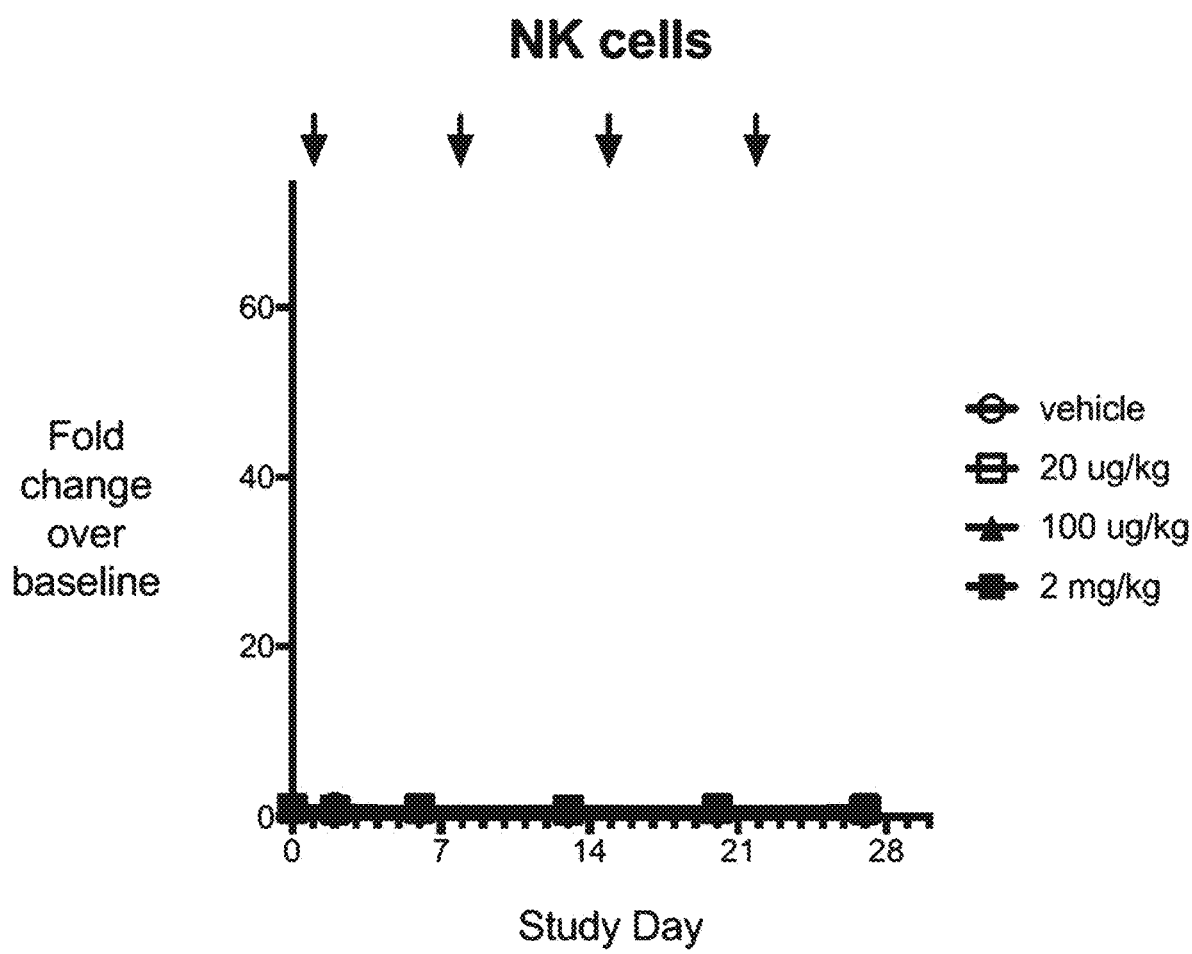
FIG. 16 shows the fold change over baseline of Natural Killer (NK) cell levels in cynomolgus monkeys treated with vehicle or compound 2 (IL2 (T3A, N88R)-15 amino acid peptide linker-Fc) by subcutaneous dosing on days 1, 7, 14, 21, and 28. NK cell levels were quantified 5 days after each dose. Compound 2 was administered at doses of 20 mg/kg, 100 µg/kg, or 2 mg/kg.
Figure 17:
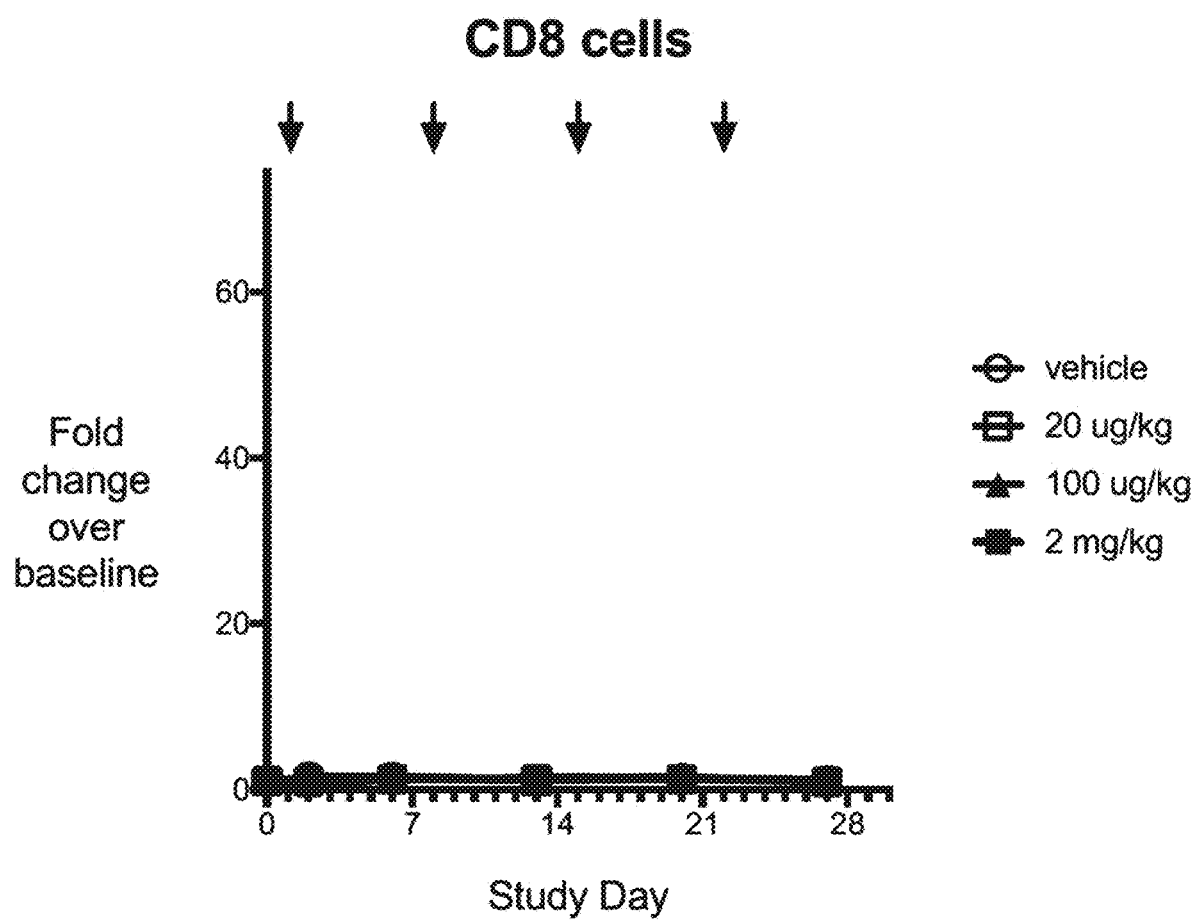
FIG. 17 shows the fold change over baseline of CD8 T cell levels in cynomolgus monkeys treated with vehicle or compound 2 (IL2 (T3A, N88R)-15 amino acid peptide linker-Fc) by subcutaneous dosing on days 1, 7, 14, 21, and 28. CD8 T cell levels were quantified 5 days after each dose. Compound 2 was administered at doses of 20 µg/kg, 100 µg/kg, or 2 mg/kg.
Figure 18:
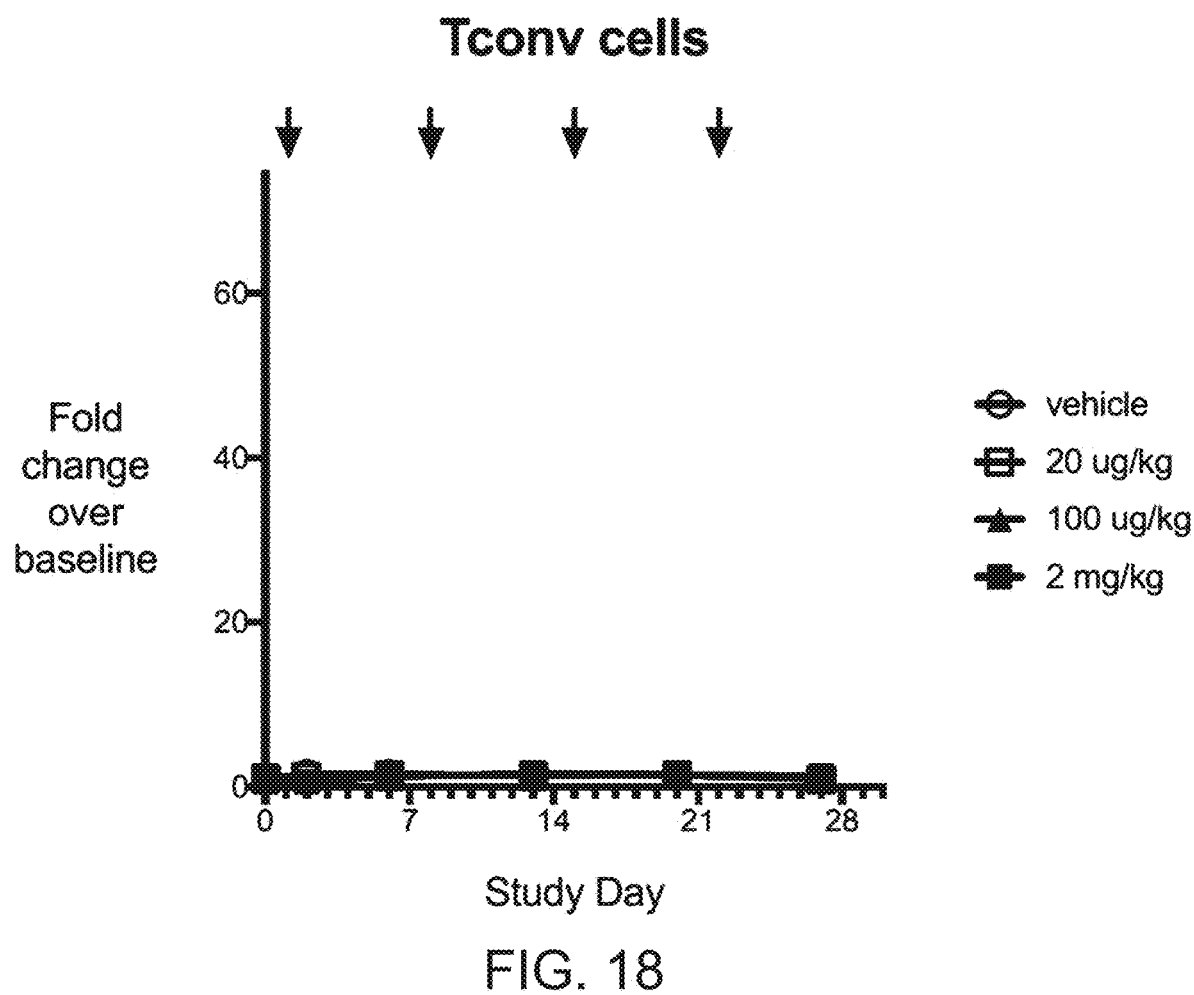
FIG. 18 shows the fold change over baseline of conventional T cell levels in cynomolgus monkeys treated with vehicle or compound 2 (IL2 (T3A, N88R)-15 amino acid peptide linker-Fc) by subcutaneous dosing on days 1, 7, 14, 21, and 28. Conventional T cell levels were quantified 5 days after each dose. Compound 2 was administered at doses of 20 µg/kg, 100 µg/kg, or 2 mg/kg.

Human peripheral blood mononuclear cells were treated with $10^{-8}$ M of Compound 1 or IL2(C125S) to assess pSTAT5+ activation. The percentage of pSTAT5+ activated cells was compared to unstimulated controls. Compound 1 induced proliferation in 97% of Treg cells, and 41% of NK cells (see FIG. 12). The percentages of proliferating $CD25^{low}$ Tconv cells, $CD25^{neg}$ Tconv cells, and CD8+ T cells were similar to those of unstimulated cells. By contrast, IL2(C125S) caused strong activation of all cell types assayed. Further analysis of the activated NK cells from FIG. 12 showed that Compound 1 selectively stimulated $CD56^{bright}$ NK cells, while IL2(C125S) stimulated NK cells with both high and low CD56 expression (see FIG. 13). These data underscore the ability of Compound 1 to selectively activate and expand Treg populations.

Example 3—Evaluation of Compound 1 (IL-2 N88R/C125S—15 Amino Acid Peptide Linker—Fc) in Cynomolgus Monkeys: Weekly Dosing The effects of Compound 1 (IL-2 N88R/C125S—15 amino acid peptide linker—Fc) on immune cell levels were evaluated in cynomolgus monkeys. Sourcing, housing and feeding of the monkeys and preparation and formulation of Compound 1 was essentially as described in Example 1. The monkeys were administered Compound 1 by subcutaneous dosing on Days 1, 8, 15 and 22 of the study. The treatment groups are shown below in Table 10.

TABLE 10

Treatment Groups and Doses

| Treatment Group | Test Article | Dose |
|---|---|---|
| 1 | vehicle | — |
| 2 | Compound 1 | 20 µg/kg |
| 3 | Compound 1 | 100 µg/kg |
| 4 | Compound 1 | 2 mg/kg |

Each treatment group contained 5 male monkeys and 5 female monkeys.

Changes in the levels of circulating immune cells were quantified by flow cytometry. Blood samples were taken for quantitation of immune cell levels 1 day after the first dose and 5 days after each dose, i.e. on Days 2, 6, 13, 20 and 27. Levels of B cells, Natural Killer (NK) cells, CD8+ T cells, conventional T cells (Tconv), and regulatory T cells (Tregs) were determined. The cells were immunophenotyped in a manner similar to that described in Example 1, with three changes: (1) the designation of Tregs as cells that were CD3+CD4+CD127-CD25+; (2) the designation of CD4 Tconv cells as CD3+CD4+CD127-CD25+; and (3) the designation of NK cells as CD3-CD20-CD8+ cells.

Figure 19:
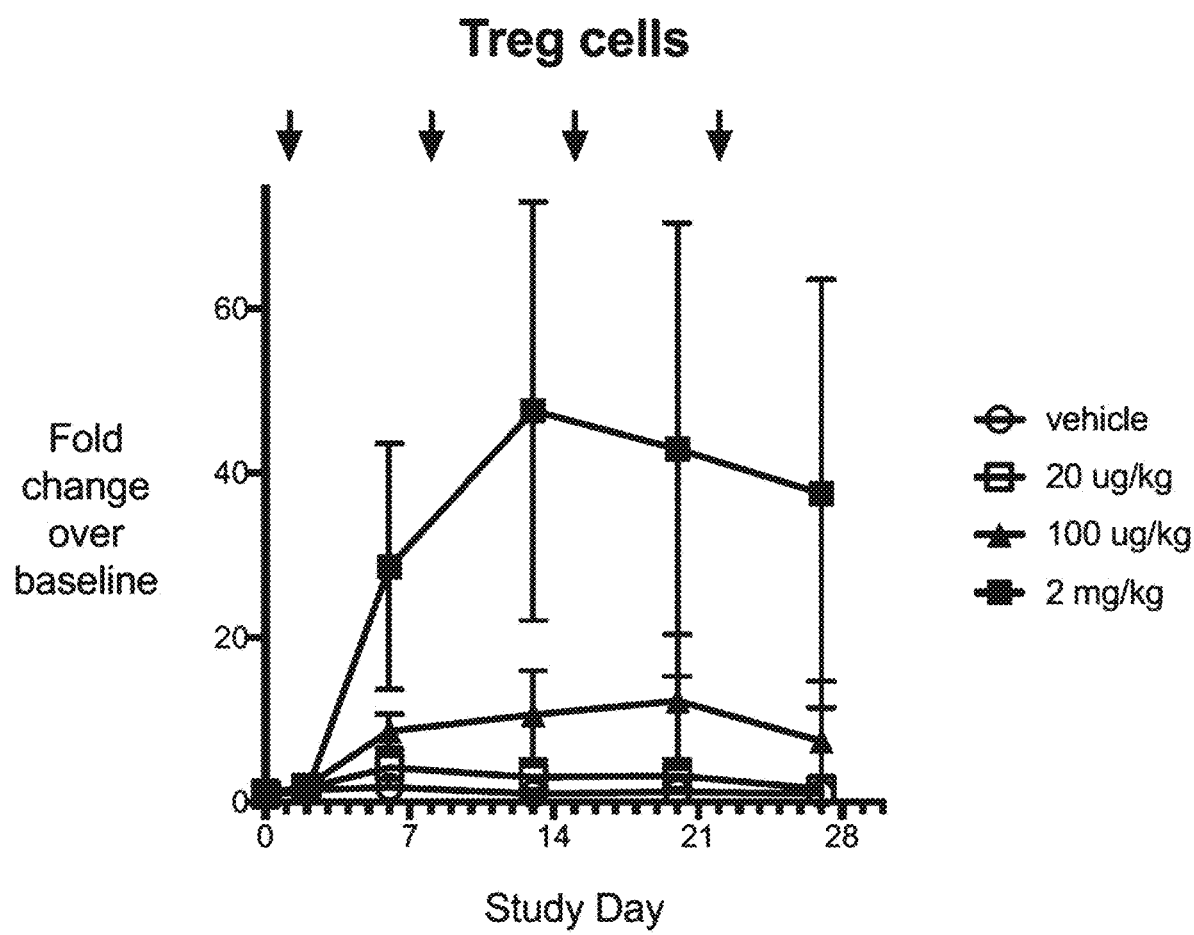
FIG. 19 shows the fold change over baseline of regulatory T cell levels in cynomolgus monkeys treated with vehicle or compound 2 (IL2 (T3A, N88R)-15 amino acid peptide linker-Fc) by subcutaneous dosing on days 1, 7, 14, 21, and 28. Regulatory T cell levels were quantified 5 days after each dose. Compound 2 was administered at doses of 20 mg/kg, 100 µg/kg, or 2 mg/kg. Compound 2 was administered at doses of 20 µg/kg, 100 µg/kg, or 2 mg/kg.
Figure 20:
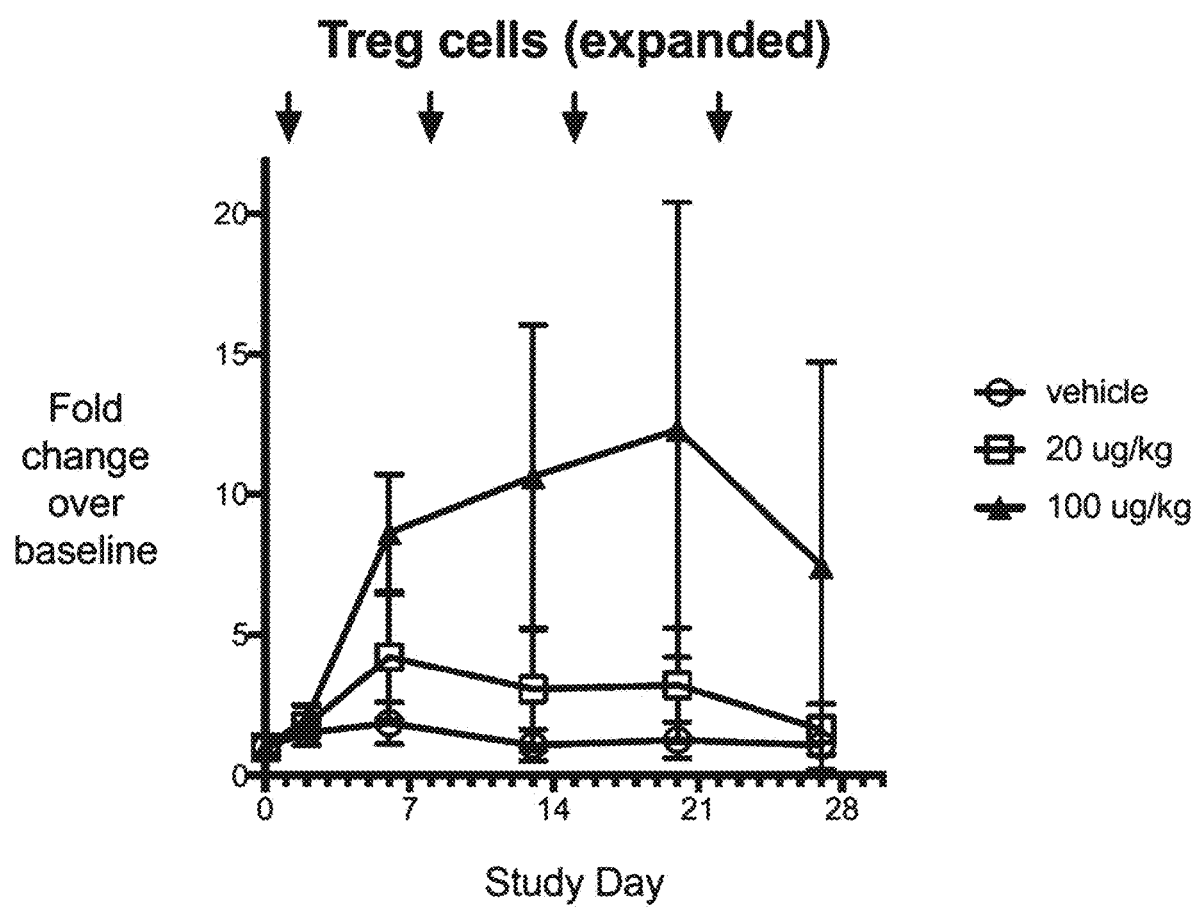
FIG. 20 is an expanded version of FIG. 19 showing the differences among the vehicle, 20 mg/kg Compound 2, and 100 mg/kg Compound 2 treatment groups with greater clarity.

As shown in FIGS. 15, 16, 17 and 18, Compound 1 had only small, insignificant effects on the levels of B cells, NK cells, CD8+ T cells, or conventional T cells, respectively. In contrast, Compound 1 treatment resulted in large increases in regulatory T cell levels that were sustained over several doses. See FIGS. 19 and 20. For example, the 2 mg/kg dose of Compound 1 resulted in an approximately 40-fold increase in regulatory T cell levels over baseline that was sustained over several doses. See FIG. 19. The results from these pharmacodynamics analyses demonstrated that there was a dose-dependent increase in the level of Tregs at 5 days post-dose. Specifically, 5 days post-dose, Tregs increased to 1.76 fold, 8.65 fold, and 28.6 fold over the baseline levels in the animals dosed at 20 ug/kg, 100 ug/kg, and 2 mg/kg, respectively. These Treg levels remained relatively stable over the remainder of the study for each of the three dose levels. These results are shown in FIG. 19 as the fold increase in Tregs over the baseline, where the absolute level for each animal is normalized to the pretest levels (taken 10 days prior to the first dose). The Y axes on FIGS. 15, 16, 17, 18, and 19 are on the same scale to directly compare the fold change to these cell populations.

Taken together, these data demonstrate the remarkable selectivity of Compound 1 for regulatory T cells.

Figure 21:
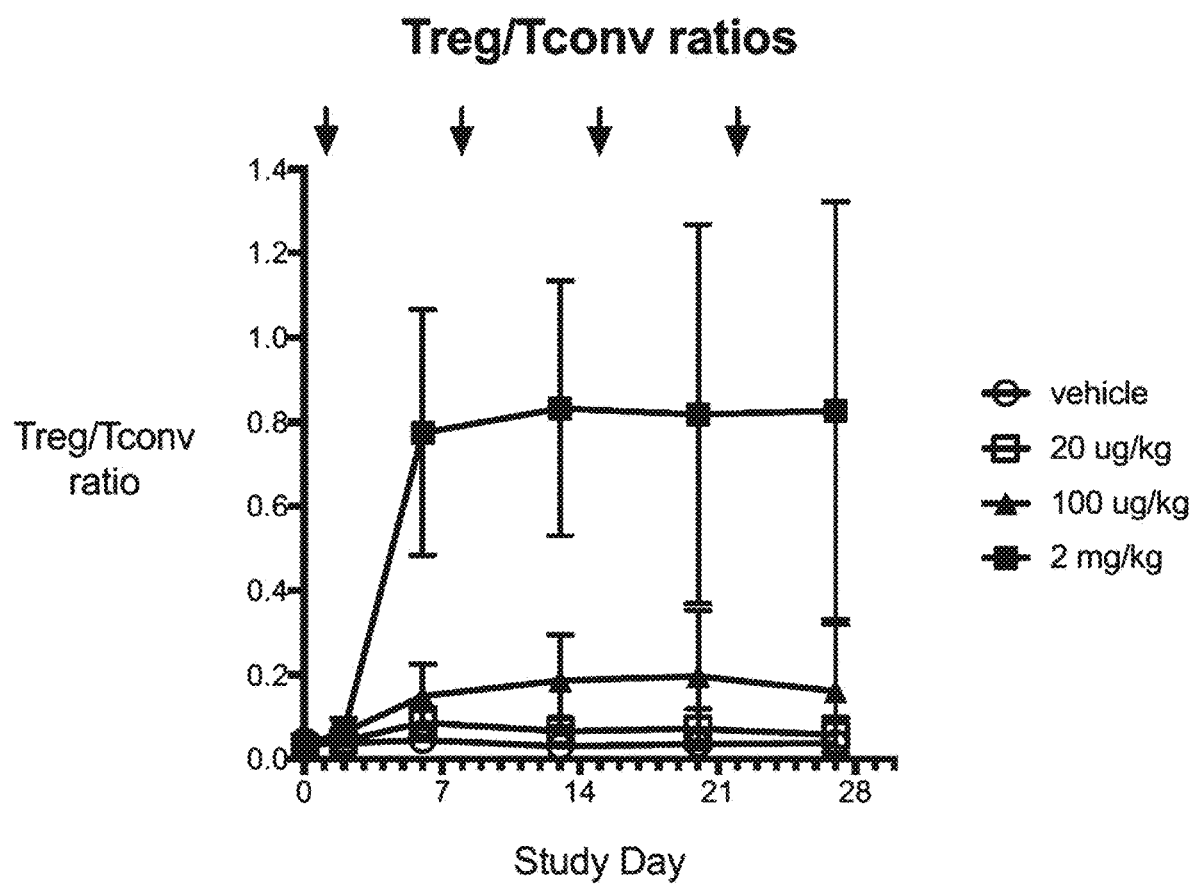
FIG. 21 shows the ratio of regulatory T cells to conventional T cells in cynomolgus monkeys treated with vehicle or compound 2 (IL2 (T3A, N88R)-15 amino acid peptide linker-Fc) by subcutaneous dosing on days 1, 7, 14, 21, and 28. T cell levels were quantified 5 days after each dose. Compound 2 was administered at doses of 20 µg/kg, 100 µg/kg, or 2 mg/kg.

In addition, Compound 1 treatment resulted in large increases in the ratio of regulatory T cells to conventional T cells (Treg/Tconv). For example, the 2 mg/kg dose of Compound 1 resulted in a Treg/Tconv ratio of approximately 0.8 which was sustained over several doses, and the 100 µg/kg dose of Compound 1 resulted in a Treg/Tconv cell ratio of approximately 0.2 which was also sustained over several doses. See FIG. 21. Specifically, on day 6 of the study, the Treg/Tconv ratios were found to be 0.09 (2.9 fold increase), 0.15 (6 fold increase), and 0.77 (23 fold increase) for the 20 ug/kg, 100 ug/kg, and 2 mg/kg doses, respectively.

No adverse effects were noted in any of the treated animals during the course of this study.

These results are particularly significant considering that graft versus host disease (GVHD) patients treated with IL2 that achieve a Treg/Tconv cell ratio of 0.2 have a high probability of disease improvement. For example, in humans, daily low dose IL-2 has been used to treat patients with chronic GVHD by augmenting the levels of Tregs (2016, Koreth J, et al., Blood, July 7; 128(1):130-7; 2011, Koreth, J., N Engl J Med., December 1; 365(22):2055-66). In the latter trial, IL-2 (aldesleukin) was given by daily subcutaneous injection for 12 weeks. Patients treated in this manner attained a greater than 5 fold increase of Tregs over baseline (Treg levels prior to treatment) and a greater than 5 fold increase in their Treg/Tconv ratios, and a 61% clinical response rate. Clinical responses were strongly associated with a Treg/Tconv ratio greater than 0.2 at the end of the first week of treatment.

Taken together, the data provided herein show that, in cynomolgus monkeys, single weekly doses of Compound 1 stimulate Treg levels in a highly selective manner to levels greatly exceeding levels that are predicted to be therapeutic in humans.

The invention claimed is:

1. A method for treating an autoimmune disease in a subject in need thereof, the method comprising administering to the subject at least two doses of a pharmaceutical composition comprising a therapeutically-effective amount of a fusion protein comprising:
   a. a human IL-2 variant protein domain comprising a substitution selected from the group consisting of T3A and C125S relative to the amino acid sequence of SEQ ID NO: 2, and a substitution selected from the group consisting of D20H, N88I, N88G, N88R, Q126L, and Q126F relative to the amino acid sequence of SEQ ID NO: 2;
   b. a peptide linker domain comprising the amino acid sequence (GGGGS)n (SEQ ID NO: 8), wherein n is 1, 2, 3 or 4; and
   c. an IgG Fc protein domain,
   wherein each domain has an amino-terminus (N-terminus) and a carboxy terminus (C-terminus);
   and wherein the fusion protein is configured so that the C-terminus of the human IL-2 variant protein domain is fused through a peptide bond to the N-terminus of the peptide linker domain, and the N-terminus of the IgG Fc protein domain is fused through a peptide bond to the C-terminus of the peptide linker domain,
   wherein the composition is administered to the subject at a dosing frequency from once every week to once every month and at a dose of 20 µg/kg to 2 mg/kg,
   wherein administration of the pharmaceutical composition to the subject increases the ratio of regulatory T cells to conventional T cells (Treg/Tconv) by at least 2.9-fold six days after administration relative to the Treg/Tconv ratio in the subject before treatment with the pharmaceutical composition,
   and wherein the autoimmune disease is selected from the group consisting of psoriasis, ulcerative colitis, and Crohn's disease.

2. The method of claim 1, wherein administration of the pharmaceutical composition to the subject increases the ratio of regulatory T cells (Treg) to conventional T cells (Tconv) to at least 0.2.

3. The method of claim 1, wherein the dosing frequency ranges from once every week to once every 2 weeks.

4. The method of claim 1, wherein the human IL-2 variant protein domain comprises the N88R substitution relative to the amino acid sequence of SEQ ID NO: 2.

5. The method of claim 1, wherein the human IL-2 variant protein domain comprises the amino acid sequence of SEQ ID NO: 1 or SEQ ID NO: 3.

6. The method of claim 1, wherein the peptide linker domain comprises the amino acid sequence of SEQ ID NO: 6.

7. The method of claim 1, wherein the IgG Fc protein domain comprises the amino acid sequence of SEQ ID NO: 7.

8. The method of claim 1, wherein the fusion protein comprises the amino acid sequence of SEQ ID NO: 4 or SEQ ID NO: 5.

9. The method of claim 1, wherein the pharmaceutical composition is administered to the subject by subcutaneous administration.

10. A method for increasing proliferation of regulatory T cells in a subject in need thereof, the method comprising administering to the subject at least two doses of a pharmaceutical composition comprising a therapeutically effective amount of a fusion protein comprising:
   a. a human IL-2 variant protein domain comprising a substitution selected from the group consisting of T3A and C125S relative to the amino acid sequence of SEQ ID NO: 2, and a substitution selected from the group consisting of D20H, N88I, N88G, N88R, Q126L, and Q126F relative to the amino acid sequence of SEQ ID NO: 2;
   b. a peptide linker domain comprising the amino acid sequence (GGGGS)n (SEQ ID NO: 8), wherein n is 1, 2, 3 or 4; and
   c. an IgG Fc protein domain,
   wherein each domain has an amino-terminus (N-terminus) and a carboxy terminus (C-terminus);
   and wherein the fusion protein is configured so that the C-terminus of the human IL-2 variant protein domain is fused through a peptide bond to the N-terminus of the peptide linker domain, and the N-terminus of the IgG Fc protein domain is fused through a peptide bond to the C-terminus of the peptide linker domain,
   wherein the composition is administered to the subject at a dosing frequency from once every week to once every month and at a dose of 20 µg/kg to 2 mg/kg, and wherein administration of the pharmaceutical composition to the subject increases the ratio of regulatory T cells to conventional T cells (Treg/Tconv) by at least 2.9-fold six days after administration relative to the Treg/Tconv ratio in the subject before treatment with the pharmaceutical composition.

11. The method of claim 10, wherein administration of the pharmaceutical composition to the subject does not increase the proliferation of conventional T cells or CD8+T cells.

12. A method for maintaining the ratio of regulatory T cells (Treg) to conventional T cells (Tconv) at a level of at least 0.2 in a subject, the method comprising administering to the subject at least two doses of a pharmaceutical composition comprising a therapeutically effective amount of a fusion protein comprising:
   a. a human IL-2 variant protein domain comprising a substitution selected from the group consisting of T3A and C125S relative to the amino acid sequence of SEQ ID NO: 2, and a substitution selected from the group consisting of D20H, N88I, N88G, N88R, Q126L, and Q126F relative to the amino acid sequence of SEQ ID NO: 2;
   b. a peptide linker domain comprising the amino acid sequence (GGGGS)n (SEQ ID NO: 8), wherein n is 1, 2, 3 or 4; and
   c. an IgG Fc protein domain,
   wherein each domain has an amino-terminus (N-terminus) and a carboxy terminus (C-terminus);
   and wherein the fusion protein is configured so that the C-terminus of the human IL-2 variant protein domain is fused through a peptide bond to the N-terminus of the peptide linker domain, and the N-terminus of the IgG Fc protein domain is fused through a peptide bond to the C-terminus of the peptide linker domain,
   wherein the composition is administered to the subject at a dosing frequency from once every week to once every month and at a dose of 20 µg/kg to 2 mg/kg,
   and wherein administration of the pharmaceutical composition to the subject increases the Treg/Tconv ratio by at least 2.9-fold six days after administration relative to the Treg/Tconv ratio in the subject before treatment with the pharmaceutical composition.

13. The method of claim 12, wherein five days after the pharmaceutical composition is administered to the subject the Treg/Tconv ratio is at least 0.2.

* * * * *

UNITED STATES PATENT AND TRADEMARK OFFICE
CERTIFICATE OF CORRECTION

Page 1 of 1

PATENT NO. : 11,077,172 B2
APPLICATION NO. : 15/806787
DATED : August 3, 2021
INVENTOR(S) : Jeffrey Greve It is certified that error appears in the above-identified patent and that said Letters Patent is hereby corrected as shown below:

On the Title Page

Item (54) and in the Specification, Column 1, Lines 1-2, change "IL-2 Variants for the Treatment of Psoriasis" to -- IL-2 Variants for the Treatment of Autoimmune Disease --.

Item (56), right column, under "OTHER PUBLICATIONS", change "Voetetal. Biochemistry John Wiley & Sons, Inc., (1990), pp. 126-" to -- Voet et al. Biochemistry John Wiley & Sons, Inc., (1990), pp. 126- --.

In the Claims

At Column 57, Line 10, change "consisting of D2OH, N88I, N88G, N88R, Q126L, and" to
-- consisting of D20H, N88I, N88G, N88R, Q126L, and --.

At Column 57, Line 37, change "the proliferation of conventional T cells or CD8+T cells." to
-- the proliferation of conventional T cells or CD8+ T cells." --.

At Column 58, Line 11, change "consisting of D2OH, N88I, N88G, N88R, Q126L, and" to
-- consisting of D20H, N88I, N88G, N88R, Q126L, and --.

Signed and Sealed this
First Day of November, 2022

Katherine Kelly Vidal
*Director of the United States Patent and Trademark Office*

SEQUENCE LISTING

<160> NUMBER OF SEQ ID NOS: 8

<210> SEQ ID NO 1
<211> LENGTH: 133
<212> TYPE: PRT
<213> ORGANISM: Artificial Sequence
<220> FEATURE:
<223> OTHER INFORMATION: N88R C125S Mutant IL2

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 3
<211> LENGTH: 133
<212> TYPE: PRT
<213> ORGANISM: Artificial Sequence

```
<220> FEATURE:
<223> OTHER INFORMATION: T3A, N88R, C125S IL2 mutant

<400> SEQUENCE: 3

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 4
<211> LENGTH: 374
<212> TYPE: PRT
<213> ORGANISM: Artificial Sequence
<220> FEATURE:
<223> OTHER INFORMATION: IL2 Fc fusion protein, Compound 1

<400> SEQUENCE: 4

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Gly Ser Gly Gly Gly Gly Ser Gly
        130                 135                 140

Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
        180                 185                 190

Asp Val Ser His Glu Asp Pro Glu Val Lys Phe Asn Trp Tyr Val Asp
```

```
            195                 200                 205
Gly Val Glu Val His Asn Ala Lys Thr Lys Pro Arg Glu Glu Gln Tyr
210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
        275                 280                 285

Asn Gln Val Ser Leu Thr Cys Leu Val Lys Gly Phe Tyr Pro Ser Asp
290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly
    370

<210> SEQ ID NO 5
<211> LENGTH: 374
<212> TYPE: PRT
<213> ORGANISM: Artificial Sequence
<220> FEATURE:
<223> OTHER INFORMATION: IL2 Fc fusion protein, Compound 2

<400> SEQUENCE: 5

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr Gly Gly Gly Ser Gly Gly Gly Ser Gly
130                 135                 140

Gly Gly Gly Ser Asp Lys Thr His Thr Cys Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
```

```
                180              185              190
Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
        210                 215                 220

Ala Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly
        370

<210> SEQ ID NO 6
<211> LENGTH: 15
<212> TYPE: PRT
<213> ORGANISM: Artificial Sequence
<220> FEATURE:
<223> OTHER INFORMATION: Peptide linker

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 226
<212> TYPE: PRT
<213> ORGANISM: Artificial Sequence
<220> FEATURE:
<223> OTHER INFORMATION: IgG1 Fc region

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly
225

<210> SEQ ID NO 8
<211> LENGTH: 5
<212> TYPE: PRT
<213> ORGANISM: Artificial Sequence
<220> FEATURE:
<223> OTHER INFORMATION: Peptide linker

<400> SEQUENCE: 8

Gly Gly Gly Gly Ser
1               5
```